US012575805B2

(12) United States Patent
Adams et al.

(10) Patent No.: US 12,575,805 B2
(45) Date of Patent: Mar. 17, 2026

(54) ULTRASOUND PROBE WITH AN INTEGRATED NEEDLE ASSEMBLY AND A COMPUTER PROGRAM PRODUCT, A METHOD AND A SYSTEM FOR PROVIDING A PATH FOR INSERTING A NEEDLE OF THE ULTRASOUND PROBE

(71) Applicant: Dandelion Technologies LLC, Vero Beach, FL (US)

(72) Inventors: Paul Adams, Vero Beach, FL (US); Christopher Vetter, Dublin, OH (US); Michael Andrew Holtman, McLean, VA (US)

(73) Assignee: Dandelion Technologies, LLC, Vero Beach, FL (US)

( * ) Notice: Subject to any disclaimer, the term of this patent is extended or adjusted under 35 U.S.C. 154(b) by 0 days.

(21) Appl. No.: 18/673,836

(22) Filed: May 24, 2024

(65) Prior Publication Data

US 2024/0307023 A1 Sep. 19, 2024

Related U.S. Application Data

(63) Continuation of application No. 18/427,452, filed on Jan. 30, 2024, now Pat. No. 12,029,608, which is a
(Continued)

(51) Int. Cl.
*A61B 8/08* (2006.01)
*A61B 8/00* (2006.01)
(Continued)

(52) U.S. Cl.
CPC .......... *A61B 8/0841* (2013.01); *A61B 8/4254* (2013.01); *A61B 8/4444* (2013.01);
(Continued)

(58) Field of Classification Search
None
See application file for complete search history.

(56) References Cited

U.S. PATENT DOCUMENTS 7,129,389 B1 10/2006 Watson
7,846,103 B2 12/2010 Cannon, Jr. et al.
(Continued)

FOREIGN PATENT DOCUMENTS

JP      4627769 B2      2/2011
WO    WO-2022221913 A1    10/2022
WO    WO-2023101690 A1    6/2023

OTHER PUBLICATIONS

International Search Report and Written Opinion for Application No. PCT/US2024/012122, U.S. Patent mailed on Jul. 2, 2024, 24 pages.
(Continued)

*Primary Examiner* — Yi-Shan Yang
(74) *Attorney, Agent, or Firm* — WEAVER IP L.L.C.

(57) ABSTRACT

A device and system for and methods of using an ultrasound probe housing containing ultrasound probes configured to produce images inside the body of a patient for procedures requiring needle or probe insertion. The ultrasound probe housing can be configured with a guide channel cut-out or aperture between the ambient side and body side of a patient. A needle guide assembly may be pivotally connected internal to the guide channel cut-out or aperture of the ultrasound probe housing at a pivot point such that during use the needle enters the patient through the needle guide assembly within the ultrasound probe housing so that the needle can be visualized by the ultrasonic probes in real time. The ultrasound probe housing may also provide an adhesion or suction quality to the body side of the device to facilitate aspects of the invention.

30 Claims, 34 Drawing Sheets

Related U.S. Application Data continuation-in-part of application No. 18/322,394, filed on May 23, 2023, now Pat. No. 12,097,069, which is a continuation of application No. 17/461, 468, filed on Aug. 30, 2021, now Pat. No. 11,701,083, which is a continuation of application No. 16/445, 355, filed on Jun. 19, 2019, now Pat. No. 11,129,588.

(60) Provisional application No. 63/590,135, filed on Oct. 13, 2023.

(51) Int. Cl.
    *A61B 17/34*            (2006.01)
    *A61B 90/00*            (2016.01)

(52) U.S. Cl.
    CPC ............ *A61B 8/483* (2013.01); *A61B 8/5253* (2013.01); *A61B 2017/3413* (2013.01); *A61B 2017/347* (2013.01); *A61B 2090/067* (2016.02)

(56) References Cited

U.S. PATENT DOCUMENTS

| | | | |
|---|---|---|---|
| 10,851,829 | B2 | 12/2020 | Becker |
| 11,000,311 | B2 | 5/2021 | Moskowitz et al. |
| 11,129,588 | B2 | 9/2021 | Adams et al. |
| 11,696,738 | B2 | 7/2023 | Adams et al. |
| 11,696,739 | B2 | 7/2023 | Adams et al. |
| 11,701,082 | B2 | 7/2023 | Adams et al. |
| 11,701,083 | B2 | 7/2023 | Adams et al. |
| 11,701,084 | B2 | 7/2023 | Adams et al. |
| 11,701,085 | B2 | 7/2023 | Adams et al. |
| 11,877,888 | B2 | 1/2024 | Adams et al. |
| 12,029,608 | B2 | 7/2024 | Adams et al. |
| 12,097,069 | B2 | 9/2024 | Adams et al. |
| 2003/0179445 | A1 | 9/2003 | Maenle et al. |
| 2006/0241368 | A1 | 10/2006 | Fichtinger et al. |
| 2007/0129686 | A1 | 6/2007 | Daily et al. |
| 2009/0093761 | A1 | 4/2009 | Sliwa et al. |
| 2011/0125022 | A1 | 5/2011 | Lazebnik |
| 2012/0296213 | A1 | 11/2012 | Mauldin, Jr. et al. |
| 2013/0066192 | A1 | 3/2013 | Sarvestani et al. |
| 2013/0102891 | A1 | 4/2013 | Binnekamp et al. |
| 2013/0131501 | A1 | 5/2013 | Blaivas et al. |
| 2013/0178789 | A1 | 7/2013 | Mackool |
| 2013/0245375 | A1 | 9/2013 | DiMaio et al. |
| 2013/0289411 | A1 | 10/2013 | Barnard et al. |
| 2013/0345718 | A1 | 12/2013 | Crawford et al. |
| 2014/0276081 | A1 | 9/2014 | Tegels |
| 2014/0364730 | A1* | 12/2014 | Marteau .................. A61B 8/54 600/440 |
| 2015/0112200 | A1* | 4/2015 | Oberg .................. A61B 8/4455 600/461 |
| 2015/0223774 | A1 | 8/2015 | Ikeda et al. |
| 2016/0008057 | A1 | 1/2016 | Peppou |
| 2016/0022309 | A1 | 1/2016 | Allaway |
| 2016/0038119 | A1 | 2/2016 | Desjardins |
| 2016/0270760 | A1 | 9/2016 | Janicki et al. |
| 2016/0278869 | A1* | 9/2016 | Grunwald .............. A61B 34/20 |
| 2016/0374644 | A1* | 12/2016 | Mauldin, Jr. .......... A61B 8/085 600/424 |
| 2017/0020558 | A1 | 1/2017 | Xu et al. |
| 2017/0360415 | A1 | 12/2017 | Rothberg et al. |
| 2018/0000446 | A1 | 1/2018 | Lu et al. |
| 2018/0078240 | A1* | 3/2018 | Pelissier .............. A61B 8/4444 |
| 2018/0161502 | A1 | 6/2018 | Nanan et al. |
| 2018/0361705 | A1 | 12/2018 | Zeng |
| 2019/0059848 | A1 | 2/2019 | Owen et al. |
| 2019/0125470 | A1* | 5/2019 | Moskowitz ........ A61B 17/3403 |
| 2020/0016373 | A1 | 1/2020 | Hulvershorn et al. |
| 2020/0030044 | A1 | 1/2020 | Wang et al. |
| 2020/0155117 | A1 | 5/2020 | Acuna et al. |
| 2020/0187981 | A1* | 6/2020 | Tian ..................... A61B 8/0841 |
| 2020/0261057 | A1 | 8/2020 | Maracaja |
| 2020/0305927 | A1 | 10/2020 | Grim et al. |
| 2020/0397399 | A1 | 12/2020 | Adams et al. |
| 2021/0259660 | A1 | 8/2021 | Bharat et al. |
| 2021/0356437 | A1* | 11/2021 | Skoglund ............. G01N 29/221 |
| 2021/0378628 | A1 | 12/2021 | Adams et al. |
| 2021/0386397 | A1 | 12/2021 | Adams et al. |
| 2021/0393234 | A1 | 12/2021 | Adams et al. |
| 2022/0000446 | A1 | 1/2022 | Adams et al. |
| 2022/0000565 | A1 | 1/2022 | Gururaj et al. |
| 2022/0008033 | A1 | 1/2022 | Adams et al. |
| 2022/0047240 | A1 | 2/2022 | Adams et al. |
| 2022/0087639 | A1 | 3/2022 | Adams et al. |
| 2023/0090966 | A1 | 3/2023 | Mauldin, Jr. et al. |
| 2023/0181152 | A1 | 6/2023 | Adams et al. |
| 2023/0293141 | A1 | 9/2023 | Adams et al. |
| 2023/0293142 | A1 | 9/2023 | Adams et al. |
| 2024/0074733 | A1 | 3/2024 | Frane et al. |
| 2024/0350113 | A1 | 10/2024 | Adams et al. |
| 2024/0366179 | A1 | 11/2024 | Adams et al. |

OTHER PUBLICATIONS

Jiang, T., et al. "Localization Accuracy of Ultrasound-actuated Needle with Color Doppler Imaging," Diagnostics (Basel) 11(5): 755, pp. 1-14, 2020.

Uemura, K., et al., "A Minimally-Occlusive Cuff Method Utilizing Ultrasound Vascular Imaging for Stress-Free Blood Pressure Measurement," ESC Congress 2020—The Digital Experience, Aug. 29, 2020-Sep. 1, 2020, National Cerebral & Cardiovascular Center, Suita, Japan, p. 2753.

International Search Report and Written Opinion of the International Searching Authority directed to Application No. PCT/US2024/029434, mailed Aug. 27, 2024; 17 pages.

International Search Report and Written Opinion of the International Searching Authority directed to Application No. PCT/US2024/012122, mailed Jul. 2, 2024; 11 pages.

U.S. Appl. No. 19/007,176, filed Dec. 31, 2024, entitled "Ultrasound Probe With an Integrated Needle Assembly and a Computer Program Product, a Method and a System for Providing a Path for Inserting a Needle of the Ultrasound Probe".

U.S. Appl. No. 19/007,186, filed Dec. 31, 2024, entitled "Ultrasound Probe With an Integrated Needle Assembly and a Computer Program Product, a Method and a System for Providing a Path for Inserting a Needle of the Ultrasound Probe".

* cited by examiner

DEVICE

ULTRASOUND PROBE WITH AN INTEGRATED NEEDLE ASSEMBLY AND A COMPUTER PROGRAM PRODUCT, A METHOD AND A SYSTEM FOR PROVIDING A PATH FOR INSERTING A NEEDLE OF THE ULTRASOUND PROBE

CROSS-REFERENCE TO RELATED APPLICATIONS

This application is a continuation of U.S. patent application Ser. No. 18/427,452, filed Jan. 30, 2024. U.S. patent application Ser. No. 18/427,452 claims priority to U.S. Provisional Patent Application No. 63/590,135, filed Oct. 13, 2023. U.S. patent application Ser. No. 18/427,452 is also a continuation-in-part of U.S. patent application Ser. No. 18/322,394, filed May 23, 2023, which is continuation of U.S. patent application Ser. No. 17/461,468, filed Aug. 30, 2021, which is a continuation of U.S. patent application Ser. No. 16/445,355, filed Jun. 19, 2019. The entirety of each of the aforementioned applications is incorporated by reference herein.

FIELD OF THE INVENTION

Embodiments of the present invention generally relate to application of ultrasonic waves in medical procedures and more particularly to an ultrasound probe with an integrated needle assembly and a computer program product, a method and a system for providing a path for inserting a needle of the ultrasound probe.

BACKGROUND ART

Procedures that require needle penetration are some of the most common medical procedures, yet remain relatively unchanged since their inception in 1891. In a typical scenario, a practitioner uses palpation of landmarks, such as the iliac crests and the spinous processes, to guide location of a needle during a blind procedure. Examples of such procedures include lumbar puncture (LP), epidural and spinal injections, and spinal nerve blocks. Failure rate of one of the most common medical procedures, lumbar puncture, however, is about 20% owing to the difficulty of identifying landmarks and the inability to visualize the location and trajectory of the needle. This rate is expected to increase as obesity increases in the global population. While ultrasound has been used to aid in the identification of structural landmarks, needle insertion continues to be an obstructed or blind procedure without significant improvement in success rates with using static ultrasound. Failure of a bedside lumbar puncture consequently leads to a fluoroscopic lumbar puncture which results in increased cost, unnecessary inpatient admissions and delay in patient care. Additionally, pain control and anesthesia has increasingly included local and regional nerve blocks. These procedures can use either landmarks or are limited to two-dimensional (2D) ultrasound, which limits the number of providers choosing this method due to the high initial skill required for a successful procedure. For example, femoral nerve blocks are increasingly being utilized to decrease the need for opiate pain control after hip fractures, which are proven to have improved pain control and decrease adverse events.

Several recent approaches are meant to address the above-mentioned problems. But each approach continues to have multiple system or use limitations. For example, certain systems include ultrasound devices with an attached needle.

These devices, however, are limited in function at least by the location or attachment of the needle away from the ultrasound transducer itself such that the needle is outside of the field of view provided by the ultrasound transducers. Other devices provide a needle that has restricted movement yielding inadequate procedural flexibility. Additionally, other certain available devices provide inadequate image viewing, such as with 2D imaging, that make needle tracking or visualization more difficult for the medical practitioner. These systems also suffer from the inability to provide a predicted optimum path within the patient for needle travel. Obstructed image viewing of the needle path and inability to predict the path of the needle leads to procedure failure. Overall, there remains an enhanced risk of injuring the anatomical parts of the body such as the tissues, nerves etc. that are located near the target internal body part.

Therefore, a need exists in the art for an ultrasound probe with an integrated needle assembly and a computer program product, a method and a system for providing a path for inserting a needle of the ultrasound probe which does not suffer from above mentioned deficiencies.

SUMMARY OF THE INVENTION

In accordance with teachings of the present invention a device for providing a path for inserting a needle inside a body of a patient for performing medical procedures is provided.

An object of the present invention is to provide a device having an ultrasound probe housing, a guide channel cut-out or aperture, and a needle guide assembly. The ultrasound probe housing generates ultrasound waves to produce images inside of the body of a patient. The ultrasound probe housing has an ambient side and a body side and can be of any shape meeting the requirements of the invention. The ultrasound probe housing may also provide an adhesion or suction quality to the body side of the device to facilitate aspects of the invention.

The guide channel cut-out or aperture is configured between the ambient side and the body side through the ultrasound probe housing. The needle guide assembly may pivotally connect internal to the guide channel cut-out or aperture on the body side of the ultrasound probe housing at a pivot point. The needle guide assembly receives a needle. A needle is adapted to slide within the needle guide assembly such that during use the needle enters the patient through the needle guide assembly within the ultrasound probe housing so that the needle can be visualized by the ultrasonic probes in real time.

Another object of the invention is to provide a device with a rotation angle sensor. The rotation angle sensor is configured at or near the pivot point and connected with the needle guide assembly or sufficiently close to the needle guide assembly to approximate the needle angle within the assembly. Further, the rotation angle sensor can be a potentiometer.

Another object of the invention is to provide a device with a rotation angle sensor. The rotation angle sensor is configured at or near the pivot point and connected with the needle guide assembly or sufficiently close to the needle guide assembly to approximate the needle angle within the assembly. Further, the rotation angle sensor can be a potentiometer.

Another object of the invention is to provide a device with a locking mechanism that will hold the angular position of the needle to a fixed position as selected by the operator as to hold the needle in a fixed angular position while the procedure is being conducted.

Another object of the invention is to provide a device with an angle of rotation of the needle guide assembly inside the guide channel cut-out or aperture of the ultrasound probe housing. The guide channel cut-out or aperture may be a slot within the ultrasound probe housing giving an angle of rotation within a range of 0 degrees to roughly 180 degrees, or may be a more complex shape, such as conical shape, to further increase the degree of rotation of the needle guide assembly beyond that of a slotted shape. Further, the needle guide assembly is configured to be actuated by either mechanical unit or electrical unit. A person skilled in the art may appreciate that range of motion of the needle guide assembly may be assisted by the use of movement aids such as a bearing collar.

Another object of the invention is to provide the device with a pressure transducer is configured to be disposed in the needle.

Another object of the invention is to provide a path for inserting a needle into a body of a patient for performing medical procedures involving an ultrasound probe. The method includes steps of receiving images of inside of body of a patient generated corresponding to reflected ultrasonic waves, from an ultrasound probe housing, generating real-time 3-Dimensional (3D) images of anatomical parts of the body between the ultrasound probe and a target internal body part, displaying the real-time 3D images on a display device connected with the ultrasound probe, optionally comparing the real-time 3D images with pre-stored reference data stored in a data repository, and providing a path for inserting the needle through the ultrasound probe towards the target internal body part. A path or paths may be displayed as a visual overlay on the display device displaying the underlying anatomy, and may be generated with the assistance of computer software, for example with the use of artificial intelligence. The path or paths may be based on the available information that is both general (non-patient specific) and/or patient specific. The operator may then accept a path in space within the patient or choose a different path. The system receiving, processing, and providing an output may be a desktop PC, notebook, handheld, or mobile device, such as a smartphone, being linked in a wired or wireless form to the ultrasound probe.

Another object of the invention is to provide the step of guiding the needle on the provided path to the target internal body part through an automated and rotatable needle guide assembly, wherein the needle being covered in the field of view of the ultrasound probe is displayed on the display device during insertion.

Another object of the invention is to provide the step of guiding the needle on the provided path to the target internal body part using a needle insertion handle provided on the needle through the rotatable needle guide assembly, wherein the needle being covered in the field of view of the ultrasound probe is displayed on a display device during insertion, and wherein the needle insertion handle provides enhanced maneuverability for the practitioner/user.

Another object of the present invention is to provide the step of providing one or more of 3D images of the previously performed medical procedures, previously provided paths for similar procedures and images and details of anatomical parts of the body. Such images may be specific to the patient having the procedure performed with the device or method of the invention, and may be general in nature.

An object of the present invention is to provide a device having an ultrasound probe housing. The ultrasound probe housing generates ultrasound waves to produce images inside of the body of a patient. The ultrasound probe housing has an ambient side and a body side. The ultrasound probe housing provides an adhesion or suction quality to the body side of the device.

Another object of the device is to allow the ultrasound array and other various device components to be removed, maintained, or replaced for sterility, cleaning and other maintenance functions.

BRIEF DESCRIPTION OF THE DRAWINGS

So that the manner in which the above recited features of the present invention can be understood in detail, a more particular description of the invention, briefly summarized above, may have been referred by examples, some of which are illustrated in the appended drawings. It is to be noted, however, that the appended drawings illustrate only typical examples of this invention and are therefore not to be considered limiting of its scope, for the invention may admit to other equally effective examples.

These and other features, benefits, and advantages of the present invention will become apparent by reference to the following text figure, with like reference numbers referring to like structures across the views, wherein.

DETAILED DESCRIPTION OF THE EMBODIMENTS

While various embodiments of the present disclosure are provided herein, it should be understood that they are presented as examples only, and are not intended to be limiting. Similarly, the drawings and diagrams depict structural or architectural examples or alternate configurations of the invention, which are provided to aid in understanding the features and functionality of the various embodiments of the invention but are not intended to be limiting. The embodiments and features may be implemented and/or altered in a variety of ways known to those of ordinary skill the art.

Figure 1:
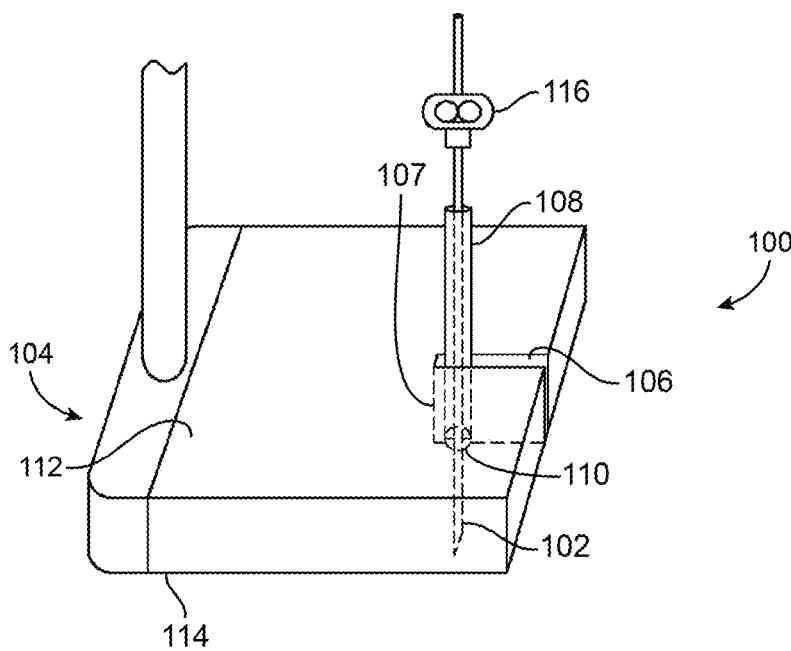
FIG. 1 illustrates a perspective view of a device providing a path for inserting a needle for performing medical procedures, in accordance with an embodiment of the present invention.

FIG. 1 illustrates a perspective view of a device 100 providing a path for inserting a needle 102 for performing medical procedures, in accordance with an embodiment of the present invention. The device 100 includes an ultrasound probe housing 104, a guide channel cut-out or aperture 106, and a needle guide assembly 108. In another embodiment of the present invention, the device 100 further includes a pivot point 110 and rotation angle sensor 111.

The ultrasound probe housing 104 contains a series of probes 105 (not shown) that generate ultrasound waves to produce images of inside of body of a patient. Ultrasound probe housing 104 having an ambient side 112 and a body side 114. Ultrasound probe housing 104 is explained in detail throughout and, for example, in conjunction with FIG. 3 of the present invention.

Guide channel cut-out or aperture 106 is configured between the ambient side 112 and the body side 114 through ultrasound probe housing 104. A needle guide assembly 108 pivotally connects to the guide channel cut-out or aperture 106 on the body side 114 of the ultrasound probe housing 104 at pivot point 110. The needle guide assembly 108 receives a needle 102. Needle 102 is adapted to slide in needle guide assembly 108 such that needle 102 enters the field of view of the ultrasound probe housing 104 upon insertion into the tissue of the patient receiving the procedure.

In an embodiment of the present invention, pivot point 110 is located near to left side 107 of the guide channel cut-out or aperture 106. However, it would be readily apparent to those skilled in the art to move pivot point 110 in the guide channel cut-out or aperture 106 to increase angle of rotation of needle 102 without deviating from the scope of the present invention.

Needle guide assembly 108 pivotally moves inside the guide channel cut-out or aperture 106 between a vertical setting and a shallow setting. As shown in FIG. 1, needle guide assembly 108 is at vertical setting. However, it would be readily apparent to those skilled in the art that the guide channel cut-out 106 may be created in multiple shapes such as circular, conical, hyperboloid, etc. to increase the angle of rotation to a desired angle without deviating from the scope of the present invention. The angle of rotation of the needle guide assembly 108 is explained by way of example in detail in conjunction with FIGS. 8 and 9 of the present invention.

Further in another embodiment of the present invention, the rotational angle sensor 111 is configured at pivot point 110 and connected with needle guide assembly 108 to measure needle location. The rotational angle sensor 111 is a potentiometer. In another embodiment of the present invention, the angle of rotation of the needle guide assembly 108 inside the guide channel cut-out or aperture 106 is in the range of 0 to 180 degrees.

In another embodiment of the present invention, device 100 further includes a needle insertion handle 116 for allowing practitioner/user 706 to hold and move needle 102 inside needle guide assembly 108. Needle guide assembly 108 is a rigid housing that is manually or automatically adjusted and provides a predetermined and rigid path to allow for precise needle insertion to the target. Needle insertion handle 116 may be a conventional cuboid plastic grip but can be modified for improved control and tactile response required in a procedure. Needle insertion handle 116 may include a plastic (or suitable material) shape such as a wing tip, protrusion, or fingerhold that resides at a distance away from the end of the needle to allow for more control with needle insertion, as shown in FIG. 1. Modifying needle insertion handle 116 may obviate practitioner/user 706 need or desire to handle needle 102 directly during the procedure. Further, needle guide assembly 108 will stabilize needle 102 in the x axis to improve practitioner/user 706 needle usage.

Figure 2:
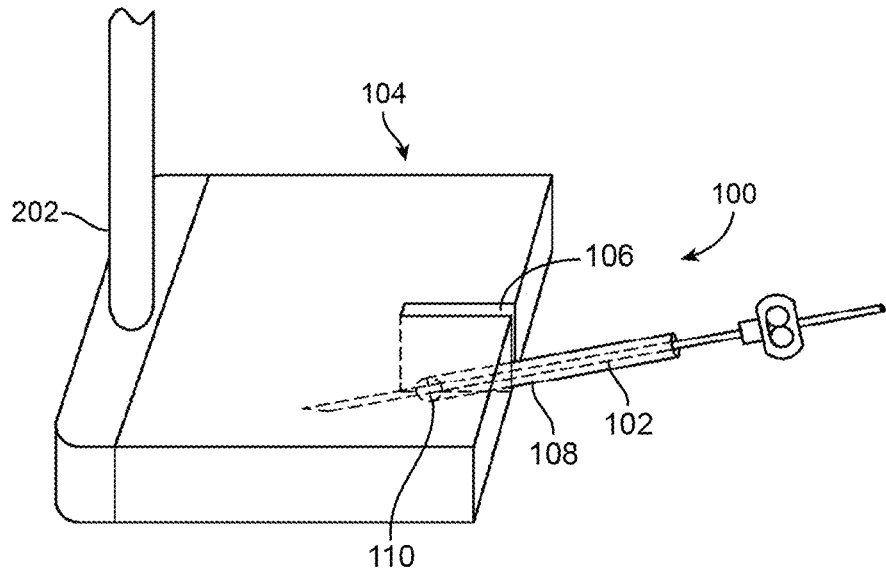
FIG. 2 illustrates another perspective view of a device providing a path for inserting a needle for performing a medical procedure, in accordance with another embodiment of the present invention.

FIG. 2 illustrates another perspective view of the device 100 providing a path for inserting needle 102 for performing medical procedure, in accordance with another embodiment of the present invention. Needle guide assembly 108 is at the shallow setting.

Needle guide assembly 108 is movable by practitioner/user 706 within guide channel cut-out or aperture 106 at any desired angle. Alternatively, needle guide assembly 108 is actuated either by a mechanical unit (such as levers) or an electrical unit (such as robotic arm). In another embodiment of the present invention, device 100 may further include a cord 202 to supply power and transmit data to ultrasound probe housing 104.

In another embodiment of the present invention, guide channel cut-out or aperture 106 is a U shape cut at the edge of the ultrasound probe housing 104. However, it would be readily apparent to those skilled in the art that various shapes (such as V-shaped) and place (such as center) to create the guide channel cut-out or aperture 106 on the ultrasound probe housing 104 may be envisioned without deviating from the scope of the present invention.

Figure 3A:
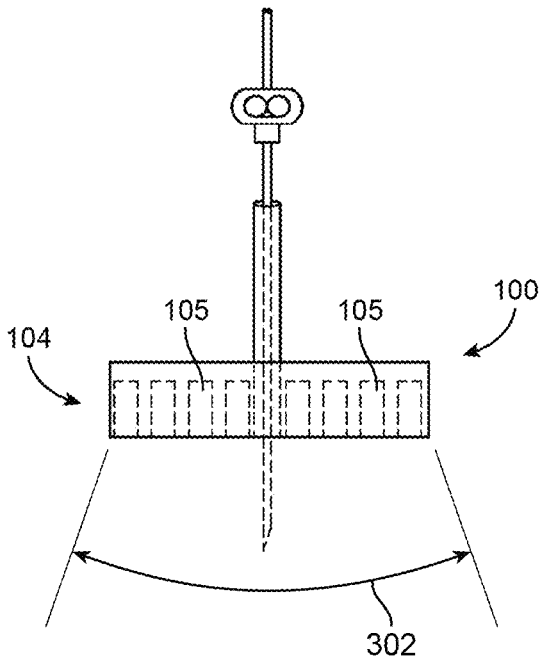
FIG. 3A illustrates a front view of a device in accordance with an embodiment of the present invention.
Figure 3B:
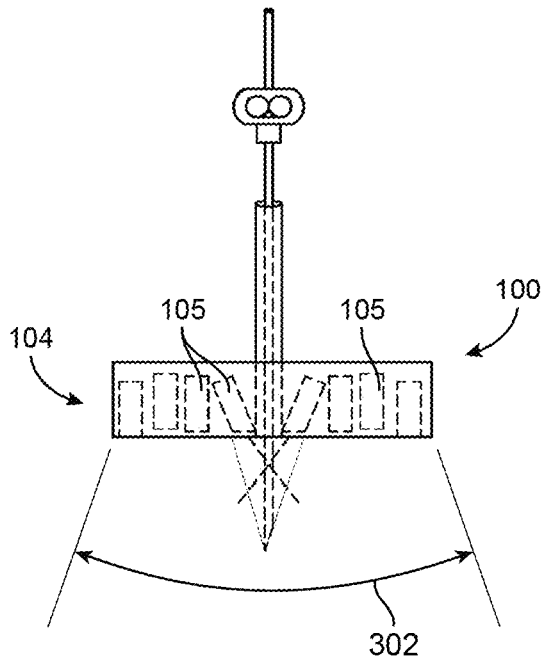
FIG. 3B illustrates a front view of a device in accordance with another embodiment of the present invention.

FIG. 3A illustrates a partial front view of device 100 in accordance with an embodiment of the present invention. Ultrasound probe housing 104 contains probes 105 that generate ultrasonic waves, receive the reflected ultrasonic waves and generate data in the form of electrical signals corresponding to the received ultrasonic waves.

Ultrasound probe housing 104 generates real-time 3-Dimensional (3D) images of anatomical parts of the body of the patient. A field 302 shows the viewable image area beneath and near the ultrasound probe housing 104. As shown by example in FIG. 3B, the array of probes 105 may be positioned within ultrasound probe housing 104 to alter the viewable image of field 302. In certain formats, probes 105 may be angled within ultrasound probe housing 104 to optimize the viewable image at the site of needle penetration beneath ultrasound probe housing 104. This may be helpful to accommodate changes to the structure of guide channel cut-out or aperture 106. Likewise, probes 105 may be positioned perpendicular to body side 114 of ultrasound probe housing 104 to give a wider viewable image area. Ultrasound probe housing 104 may also contain a mixed array of angled and perpendicular probes 105 to alter viewable image geometries. It would be readily apparent to those skilled in the art that various types and shapes of ultrasound probe housing 104 containing probes 105 may be envisioned without deviating from the scope of the present invention.

Figure 4A:
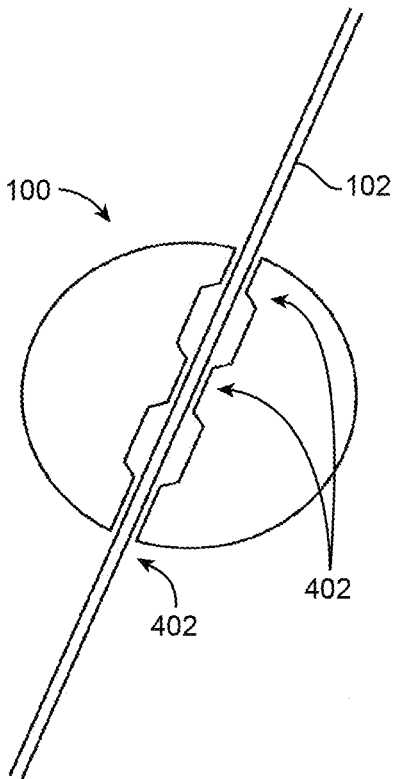
FIG. 4A illustrates a perspective view of a needle guide assembly in accordance with an embodiment of the present invention.

FIG. 4A illustrates a perspective view of needle 102 in accordance with an embodiment of the present invention. In another embodiment of the present invention, device 100 further includes plurality of guide bearings 402 to facilitate sliding motion of needle 102 in needle guide assembly 108 (as shown by example in FIG. 1 to FIG. 3). Needle guide assembly 108 stabilizes needle 102 during insertion into the patient body and attaches needle 102 to ultrasound probe housing 104.

Figure 4B:
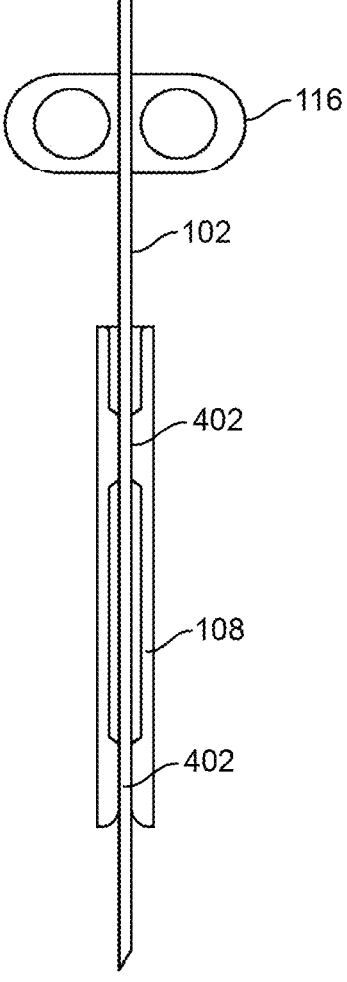
FIG. 4B provides another perspective view of needle in accordance with an embodiment of the invention.

FIG. 4B provides another perspective view of needle 102 in accordance with an embodiment of the invention. FIG. 4A further includes exemplary needle insertion handle 116. It will be appreciated that examples of guide bearings 402 include but are not limited to 1 or more sliding bearings designed to allow needle 102 to move in the radial direction, restricts the needle from bending on insertion, and maintains the needle position in space.

Figure 5:
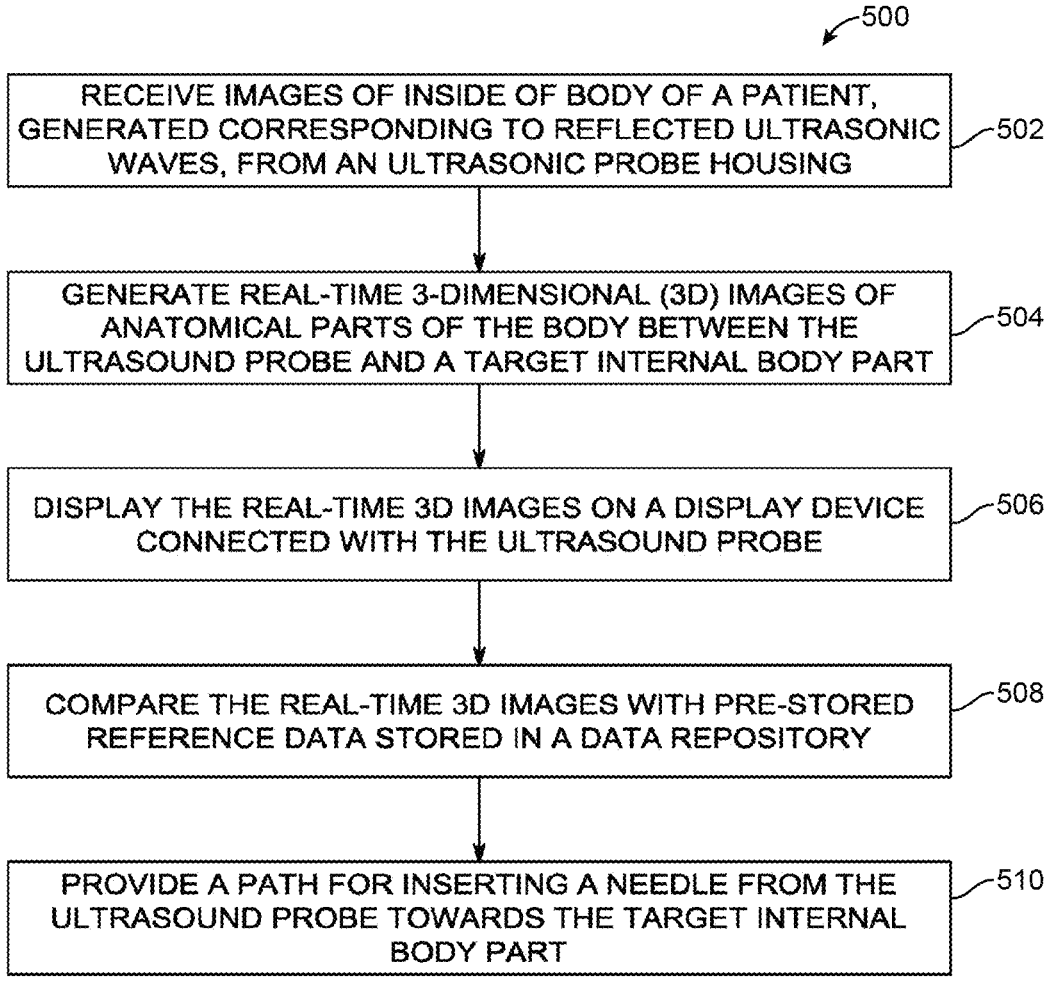
FIG. 5 illustrates a method for providing a path for inserting a needle of the ultrasound probe inside a body of a patient, in accordance with an embodiment of the present invention.

FIG. 5 illustrates a method 500 for providing a path for inserting inside a body of a patient during medical procedures involving an ultrasound probe housing in accordance with an embodiment of the present invention. The method 500 initiates with a step 502 of receiving images of inside of body of a patient, generated corresponding to reflected ultrasonic waves from probes 105 of ultrasound probe housing 104. Ultrasound probe housing 104 of step 502 is explained in detail in conjunction with FIG. 1 and FIG. 3 of the present invention.

Step 502 is followed by a step 504 of generating real-time 3-Dimensional (3D) images of anatomical parts of the body between the ultrasound probe and an internal target body location. Data from ultrasound probe housing 104 is transmitted to a processor. The processor processes received data and generates 3D images of anatomical parts in real-time.

Step 504 is followed by a step 506 of displaying the real-time 3D images on a display device receiving information from device 100. The processor processes the data received from the ultrasound probes and the display device displays the processed data. The display device may also display a predicted path 705 of needle 102 based on the current body location of device 100 and current needle angular position. Predicted path 705 represents the path that needle 102 would take through the patient anatomy if needle were extended in space from and based on its current coordinates. The display device and the processor is explained herein and also in further conjunction with FIG. 6 of the present invention.

Figure 6:
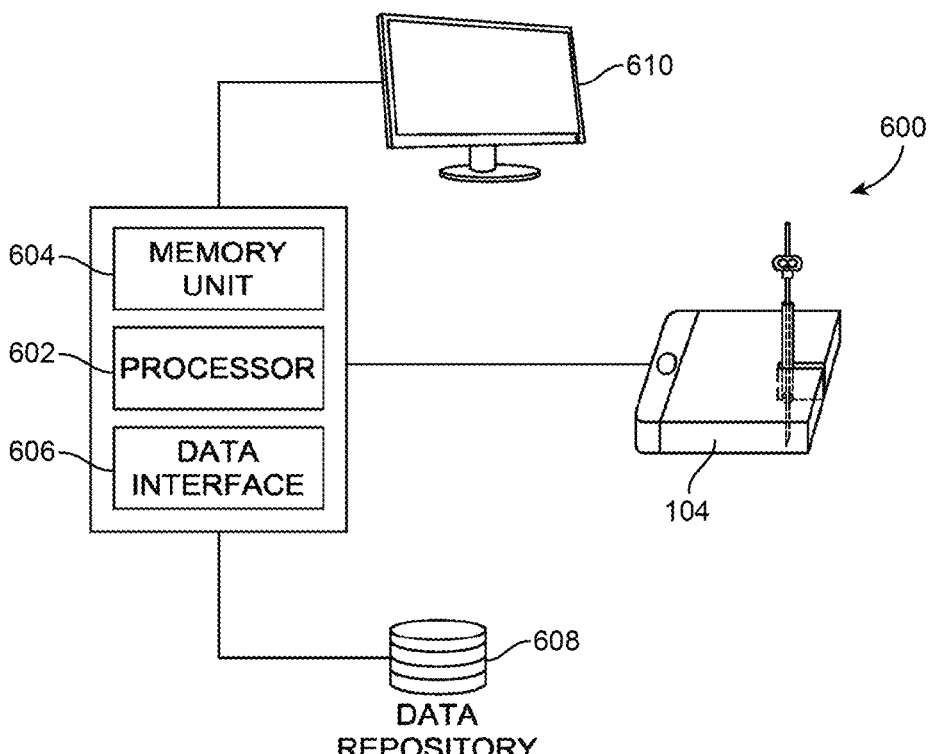
FIG. 6 illustrates a system for providing a path for inserting a needle for medical procedures, in accordance with an embodiment of the present invention.

Step 506 may optionally be followed by a step 508 of comparing the real time 3D images and data with reference data stored in a data repository 608 (as shown by example in FIG. 6). Data repository 608 may also be at a remote location but accessible in real time, such as with cloud storage. Further, step 506 or 508 may then be followed by step 510 of providing a recommended path 707 for inserting needle 102 through the ultrasound probe housing towards the internal target body location. Recommended path 707 is a path through the anatomy of the patient based on available data that may include current real time data from device 100, stored data, and the type of procedure to be performed. The recommended path 707 for inserting needle 102 through the ultrasound probe is displayed on the display device. Both the distance and angle of the device from its current position to the position matching that of the recommended path can be displayed to enable practitioner/user 706 to relocate the device on the patient body to be able to match the recommended path. Predicted path 705 and recommended path 707 may differ from each other. Practitioner/user 706 has the option to use the recommended path 707 or to select an alternate path based on the real time 3D image display and predicted path 705.

Examples of the pre-stored data include but not limited to one or more 2D and 3D images of the previously performed medical procedures that can be patient-specific, previously provided paths for similar procedures, and images and details of anatomical parts of the body, etc.

In an exemplary embodiment of the present invention, the 3D image shows a kidney of a patient in real time, then the processor compares the real time 3D image with the pre-stored data. The pre-stored data showcase the path for inserting needle 102 that corresponds to the image of the kidney. The desired path to perform the medical procedure is displayed on the display device depending upon the real time image.

It would be readily apparent to those skilled in the art that artificial intelligence may be involved at various stages of information usage for the device. For example, AI may assess the path of treating the internal target body location from the data repository 608 (shown in FIG. 6) and may identify a recommended path 707 (shown in FIG. 7) on receiving the similar situation without deviating from the scope of the present invention.

FIG. 6 illustrates a system 600 for providing a path or paths for inserting needle 102 for medical procedures, in accordance with an embodiment of the present invention. The system 600 further includes an ultrasound probe housing 104, a guide channel cut-out or aperture 106, needle guide assembly 108, a processor 602, a memory unit 604, a data interface 606, a data repository 608 and a display unit 610.

The ultrasound probe housing 104, the guide channel cut-out or aperture 106 and needle guide assembly 108 are explained in detail in conjunction with exemplary FIG. 1 to FIG. 3 of the present invention. Processor 602 is connected with the ultrasound probe housing 104 through the data interface 606, which may or may not be a physical, wired connection. For instance, data interface 606 may receive data from a wireless, cellular, or bluetooth connection. Thus, processor 602 may be connected to ultrasound probe housing via a wired or wireless connection.

The data interface 606 receives data from the ultrasound probe housing 104 and transfers the received data to the processor 602 for processing. Examples of the processor 602 can include any system that processes images to predict and map the real patient's anatomy during the live procedure based on changes in echogenecity during the ultrasound. This can include the use of AI or other simulated intelligent programs.

The memory unit 604, the display unit 610 and the data repository 608 are connected with the processor 602, and may each be stand-alone equipment or could be a composite device, such as a desktop PC, notebook, handheld, or mobile device, such as a smartphone. The memory unit 604 stores the instructions, the processor 602 processes the stored instructions and the display unit 610 displays the processed instructions. The instructions are explained in the conjunction with FIG. 5 (method 500) of the present invention.

Examples of the memory unit 604 include but not limited to a fixed memory unit or a portable memory unit that can be inserted into the device. It will be appreciated that memory unit 604 would have sufficient memory to adequately store large volumes of information. It is expected that each system may offer advantages in certain use situations. For example, a portable memory unit may also be insertable into and compatible with an available medical record system for information exchange. A fixed memory unit may achieve a similar goal by having a port for information exchange. Examples of the display unit 610 include but not limited to LCD, LED, OLED, TFT, or any specific display of any unit device capable of visually providing information such as on a desktop PC, notebook, handheld, or mobile device, such as a smartphone.

Figure 7:
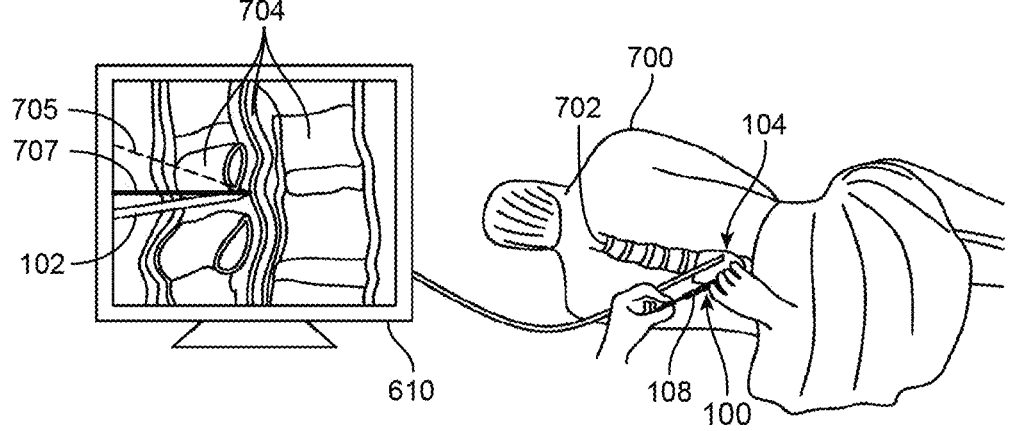
FIG. 7 illustrates a schematic diagram of performing medical procedures on the patient using a device in which a pathway for needle insertion into the patient is provided, in accordance with an embodiment of the present invention.

FIG. 7 illustrates a schematic diagram of performing medical procedure on the patient 700 using the device 100, in accordance with an embodiment of the present invention. In this example, ultrasound probe housing 104 is placed on the back of the patient 700 to perform a medical procedure on spine 702.

The ultrasound probe housing 104 captures images of spine 702 and other anatomical body parts 704 of patient 700 and displays the images on the display device 610 in real time. The display of spine 702 and anatomical body parts 704 allows a practitioner/user 706 to move needle 102, which is placed inside needle guide assembly 108, through the guide channel cut-out or aperture 106 to perform the required medical procedure on the desired location of the body part of the patient 700.

Device 100 allows practitioner/user 706 to perform the medical procedure with greater ease and on the desired location. Due to its location within and through ultrasound probe housing 104, the visibility of needle 102 in 3D allows practitioner/user 706 viewing of the desired location from multiple angles for improved procedural accuracy.

Further, FIG. 7 illustrates use of device 100 where the pathway for insertion of needle 102 through ultrasound probe housing 104 is predicted and displayed on display unit 610 based on information collected in real time and/or from data repository 608 of system 600. The control unit will take the angular position input from the potentiometer and automatically adjust the optimum angle of needle 102 via a motor to pass between anatomical structures, for example, spinous processes, for procedural success. The angle of needle 102 may also be manually managed by a movement mechanism such as a turning dial to set a final needle path. Practitioner/user 706 can choose to follow predicted path 705 for needle 102, recommended path 707 for needle 102, or some other path of the operator's choosing. Once practitioner/user 706 selects an insertion pathway, needle guide assembly 108 is locked in position to allow needle 102 to be inserted along the selected path. Depending on the embodiment of the device, practitioner/user 706 would also be able to stabilize the device location relative to the patient body by actuating attachment features of device 100 discussed herein. The insertion of needle 102 can be manually or automatically driven by or through device 100. It will be appreciated that system 600 will use computer processing in determining and displaying predicted path 705 and recommended path 707, and such processing may be based on artificial intelligence. In another embodiment of the invention, the display device may further display anticipated procedural steps to be performed for the specific procedure being undertaken by practitioner/user 706. Upcoming procedure steps may be indicated as textual prompts, bubble callouts, audibles, and may also include voice commands or prompts.

Figure 8A:
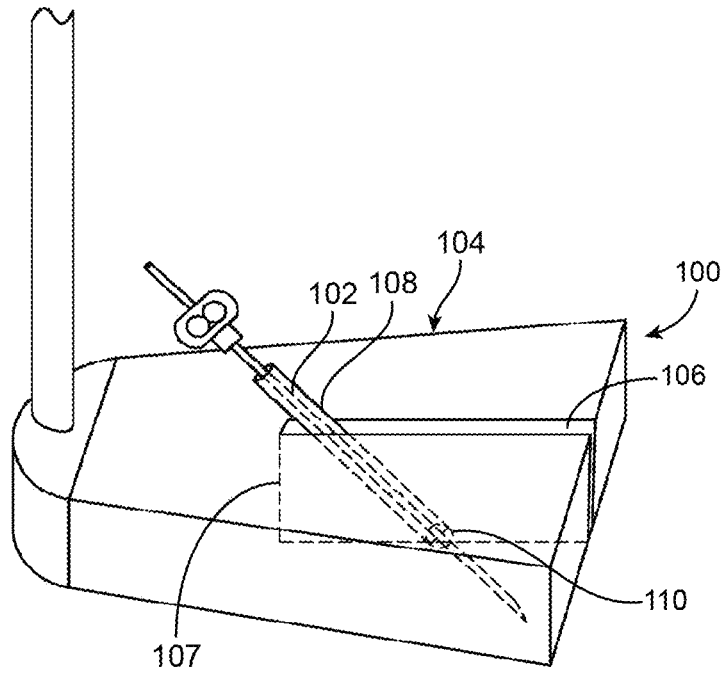
FIG. 8A illustrates a perspective view of the device providing a path for inserting a needle for performing a medical procedure, in accordance with an embodiment of the present invention.
Figure 8B:
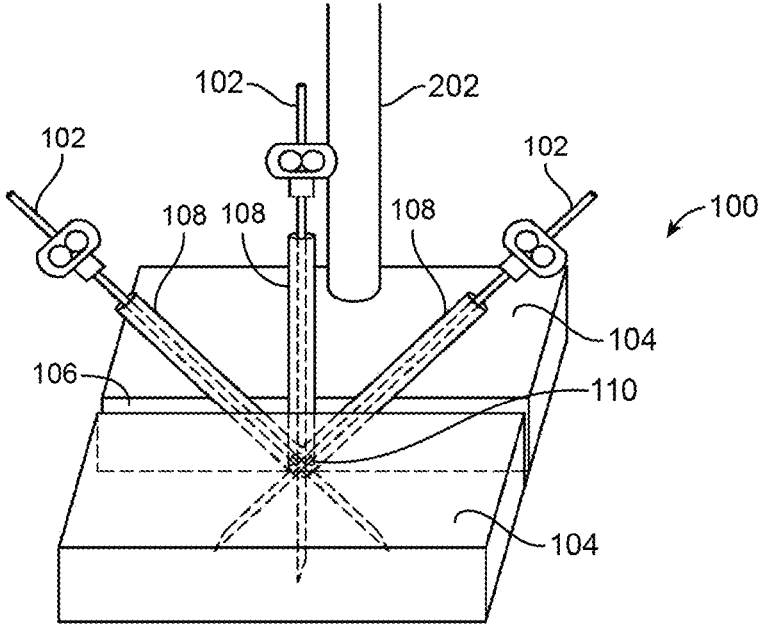
FIG. 8B illustrates a perspective view of the device providing a path for inserting a needle for performing a medical procedure, in accordance with another embodiment of the present invention.
Figure 9A:
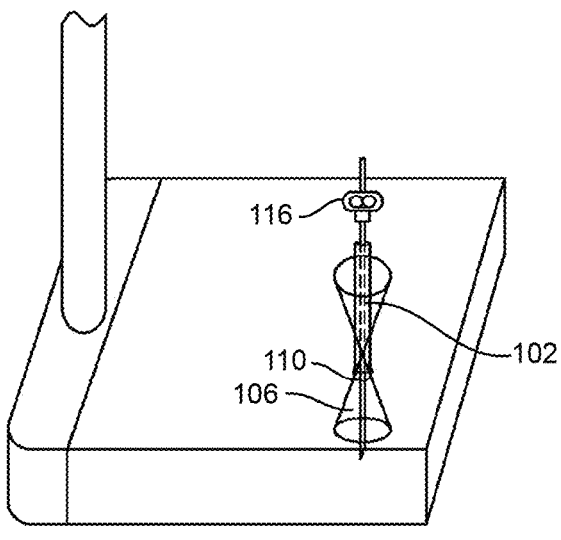
FIG. 9A illustrates a perspective view of the device providing a path for inserting a needle for performing medical procedure, in accordance with another embodiment of the present invention.
Figure 9B:
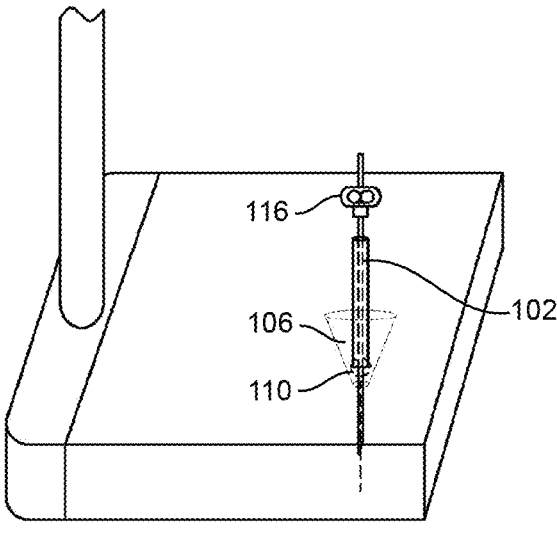
FIG. 9B illustrates a perspective view of the device providing a path for inserting a needle for performing medical procedure, in accordance with another embodiment of the present invention.
Figure 9C:
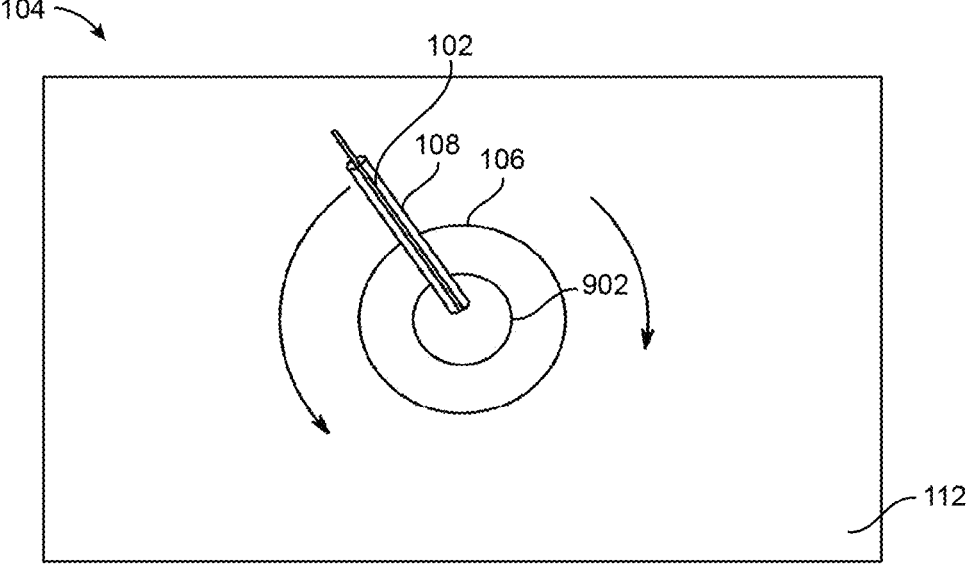
FIG. 9C illustrates a top view of the device providing a path for inserting a needle for performing medical procedure, in accordance with another embodiment of the present invention.
Figure 9D:
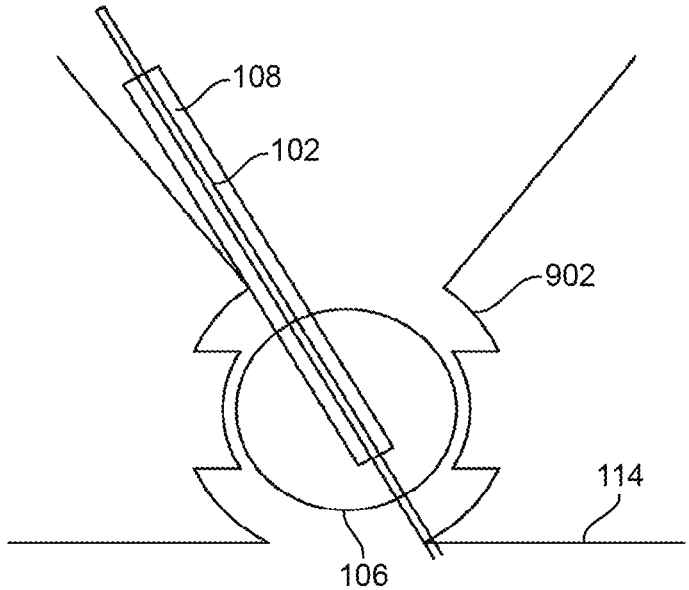
FIG. 9D illustrates a side view cutaway of the device providing a path for inserting a needle for performing medical procedure, in accordance with another embodiment of the present invention.

FIG. 8A illustrates another perspective view of the device 100 providing a path for inserting a needle 102 for performing the medical procedure, in accordance with another embodiment of the present invention. The length of the guide channel cut-out or aperture 106 is extended to allow needle guide assembly 108 to rotate in both directions within the channel-like structure, i.e., up to 180 degrees of total range of movement. Pivot point 110 is now away from the left side 107 of the guide channel cut-out or aperture 106. The needle guide assembly 108 passes through pivot point 110 and thus the angle of rotation increases from approximately 0 to 90 degrees to a fuller range of 0 to 90 degrees and 0 to minus 90 degrees. FIG. 8B provides another example where guide channel cut-out or aperture 106 provides a greater range of motion over device 100 as depicted in exemplary FIG. 1. In this embodiment, it will be appreciated that guide channel cut-out or aperture 106 has rotated from the direction provided in FIG. 8A. It will further be appreciated that the location of guide channel cut-out or aperture 106 is not fixed so long as needle 102 exits through body side 114 of ultrasound probe housing 104 of device 100 to achieve the purposes of the invention.

FIG. 9 illustrates various views of device 100 for providing a path for inserting needle 102 for performing a medical procedure with guide channel cut-out or aperture 106 having cone-like geometries. Needle guide assembly 108 pivotally connects to the guide channel cut-out or aperture 106 on or near the body side 114 of the ultrasound probe housing 104 at pivot point 110. In these configurations, needle guide assembly 108 and guide channel cut-out or aperture 106 may use a spherical bearing or similar device that allows needle 102 to rotate both radially and circumferentially, as shown in FIGS. 9C and 9D. Needle 102 is adapted to slide in needle guide assembly 108 such that the needle 102 is in a field of view of the ultrasound probe housing 104 upon insertion into the tissue of the patient receiving the procedure. It will be appreciated that guide channel cut-out or aperture 106 may be a cone or hyperboloid shape, for example as shown as in FIGS. 9A and 9B, to potentially provide greater degrees of movement over the guide channel cut-out or aperture 106 as depicture in FIG. 1. It would be readily apparent to those skilled in the art that various shapes and sizes of guide channel cut-out or aperture 106 may be envisioned without deviating from the scope of the present invention.

Figure 10A:
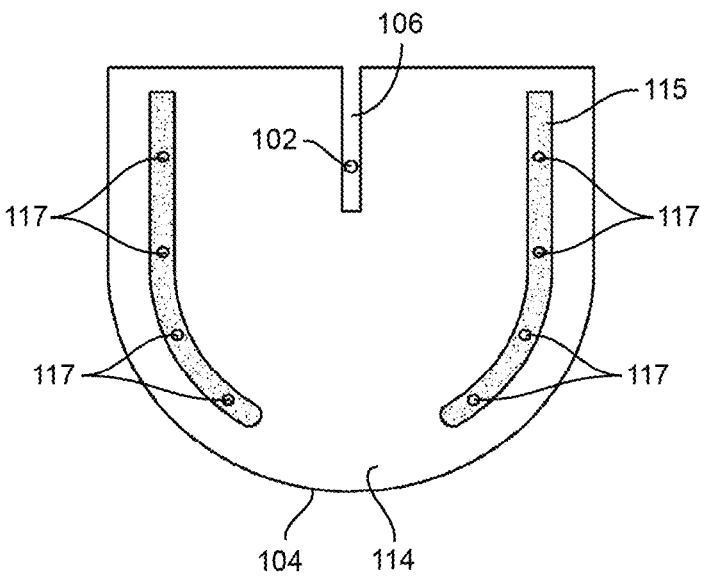
FIG. 10A illustrates a bottom view of the ultrasound probe housing having adhesion points located at the perimeter of the body side of the device in accordance with another embodiment of the present invention.

FIG. 10A illustrates a bottom view of ultrasound probe housing 104 of device 100 having adhesion points 115 located on body side 114 of ultrasound probe housing 104. Adhesion points 115, which may further contain holes 117, fix or adhere ultrasound probe housing 104 in location on the patient to maintain further control of the device for needle penetration. FIG. 10A depicts adhesion points 115 along the perimeter of ultrasound probe housing 104, but it will be appreciated that adhesion points 115 may be located anywhere across body side 114 of ultrasound probe housing 104 so long as they do not interfere with the ability of probes 105 to generate the viewable image field required for the procedure to be performed. FIG. 10A provides adhesion points 115 in the shape of elongated depressions, but adhesion points 115 may be any shape, such as channels, cups, cups with lips or pronounced outer edges, or may have no additional contouring different from body side 114 of ultrasound probe housing 104. It will be appreciated that ultrasound probe housing 104 may be held in place during the procedure by applying suction or tactile adhesion. Holes 117 may provide suction forces to adhesion points 115 in one format and may be a source of skin adhesive to adhere ultrasound probe housing 104 in place in another format.

Figure 10B:
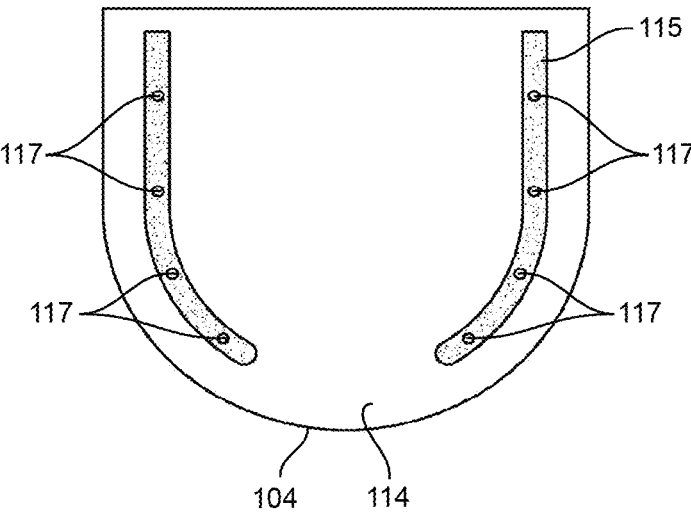
FIG. 10B illustrates a bottom view of the ultrasound probe housing having adhesion points located at the perimeter of the body side of the device in accordance with another embodiment of the present invention.

FIG. 10B provides a bottom of ultrasound probe housing 104 with no guide channel cut-out or aperture 106. This embodiment provides the fixing ability of ultrasound probe housing 104 as described herein with the ability to have needle 102 attached to the ultrasound probe housing 104 in an external manner, or to have needle 102 unattached completely per practitioner/user 706 preference. It will be appreciated that each of the devices disclosed having adhesion points 115 may be without guide channel cut-out or aperture 106 and still provide the ability to fix the device to the patient as desired.

Figure 11A:
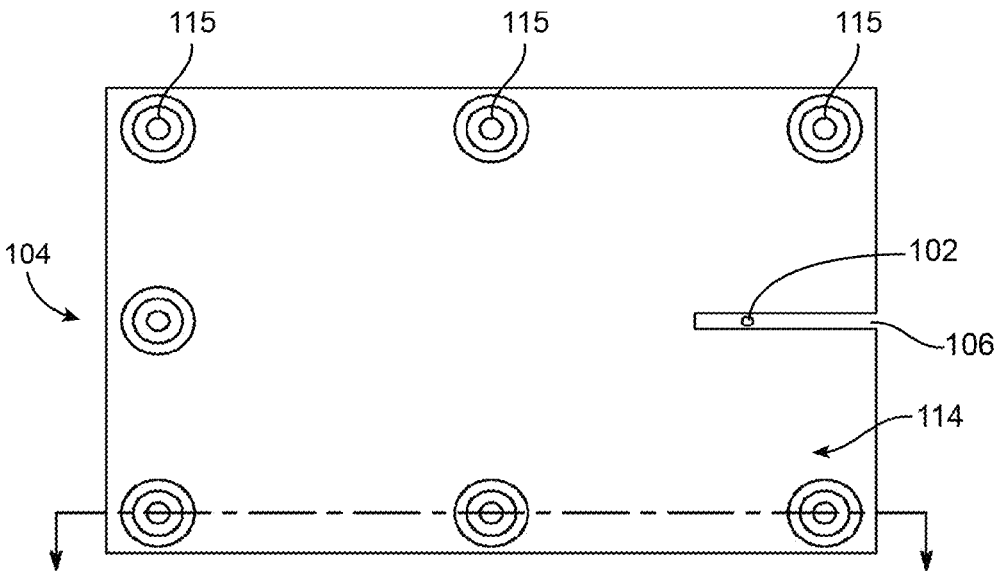
FIG. 11A illustrates a bottom view of the ultrasound probe housing having adhesion points located at the perimeter of the body side of the device in accordance with another embodiment of the present invention.
Figure 11B:
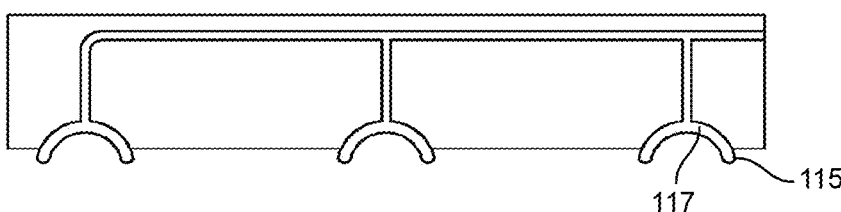
FIG. 11B provides a side cutaway view of the ultrasound probe housing having adhesion points located at the perimeter of the body side of the device in accordance with another embodiment of the present invention.

FIG. 11A demonstrates a bottom view of ultrasound probe housing 104 having adhesion points 115 located at the perimeter of the body side 114 of device 100 (shown in FIG. 1) in accordance with an embodiment of the present invention. FIG. 11B provides adhesion points 115 shaped as depressions with structure along the perimeter of said depressions to facilitate suction contact, e.g. suction cups. Adhesion points 115 further contain holes 117 through which suction forces may be applied to the contact point on the patient body. Ultrasound probe housing 104 contains internal structure such as tubing or channels for air exchange to create suction through holes 117. It will be appreciated that the exact architecture needed to facilitate suction forces can vary so long as it does not interfere with the purposes of this invention.

FIG. 11B provides a side cutaway view of ultrasound probe housing 104 in which adhesion points 115 and holes 117 are apparent and opened to body side 114. It will be appreciated that holes 117 and the corresponding architecture within ultrasound probe housing 104 may provide a source of adhesive instead of suction forces by which to fix device 100.

Figure 12A:
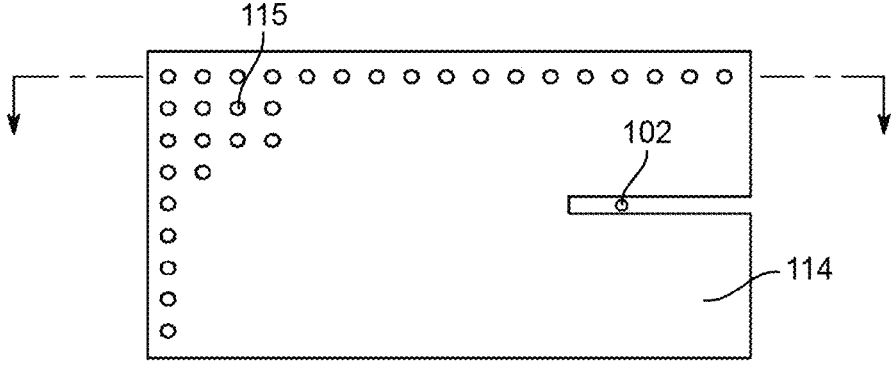
FIG. 12A illustrates a bottom view of the ultrasound probe housing having adhesion points located across the body side of the device in accordance with another embodiment of the present invention.
Figure 12B:
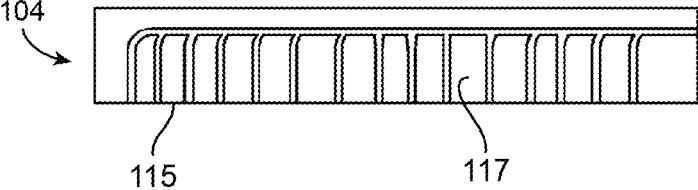
FIG. 12B illustrates a side cutaway view of ultrasound probe housing in which adhesion points and holes are apparent and opened to body side of the device in accordance with another embodiment of the present invention.

FIG. 12A illustrates a bottom view of the ultrasound probe housing 104 having adhesion points 115 located across body side 114 of device 100 in accordance with another embodiment of the present invention. Adhesion points 115 are also holes 117 in this configuration and have no additional contouring on body side 114 of device 100. FIG. 12B provides a side cutaway view of ultrasound probe housing 104 in which adhesion points 115 and holes 117 are apparent and opened to body side 114. It will be appreciated that holes 117 and the corresponding architecture within ultrasound probe housing 104 may provide a source of adhesive instead of suction forces by which to fix device 100. FIG. 12B provides a side view cutaway for illustrate the exemplary architecture of ultrasound probe housing 104.

Figure 13A:
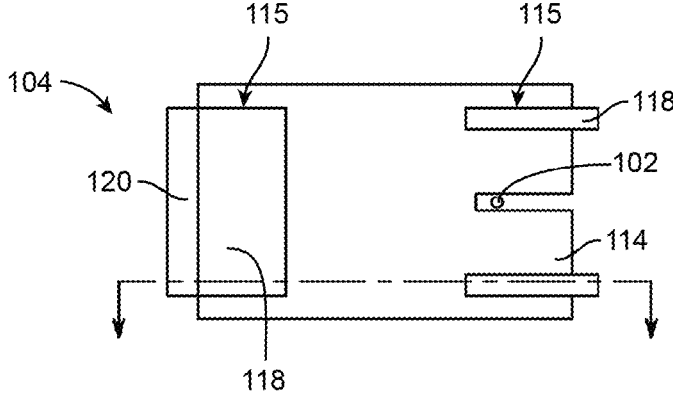
FIG. 13A illustrates a perspective view of the ultrasound probe housing having adhesion points located across the body side of the device in accordance with another embodiment of the present invention.
Figure 13B:
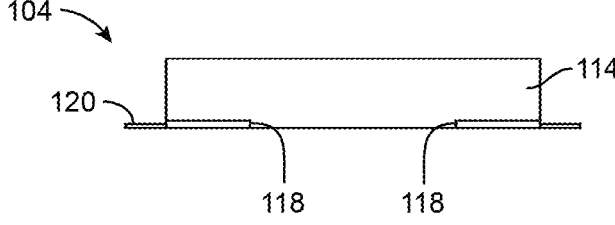
FIG. 13B illustrates a side view of ultrasound probe housing in which adhesion points and adhesive pads are apparent on body side of the device in accordance with another embodiment of the present invention.

FIG. 13A illustrates a bottom view of ultrasound probe housing 104 having adhesion points 115 located on body side 114 of device 100 in accordance with an embodiment of the present invention, where adhesion points 115 are ready for use adhesive pads or films 118. Adhesion points 115 may further contain a protective cover over adhesive pads or films 118 for storage that can be removed at time of use during the surgical procedure. It will be appreciated that body side 114 may be a receptacle for replaceable adhesive pads or films 118 that may be disposed of after each procedure. Such disposable adhesive pads or films 118 may be sterile. Ultrasound probe housing 104 may contain a removable cover 120 that coupleably joins all or a portion of body side 114. Removable cover 120 may itself provide adhesive pads or films 118 or the surface for adhesive pads or films 118 that can be fitted to body side 114 of device 100 for ease of use. Each removable cover 120 may be sterile and individually provided to ultrasound probe housing 104 for the specific procedure. FIG. 13B provides a side view of ultrasound probe housing 104 in which adhesion points 115 and adhesive pads or films 118 are apparent on body side 114.

Figure 14:
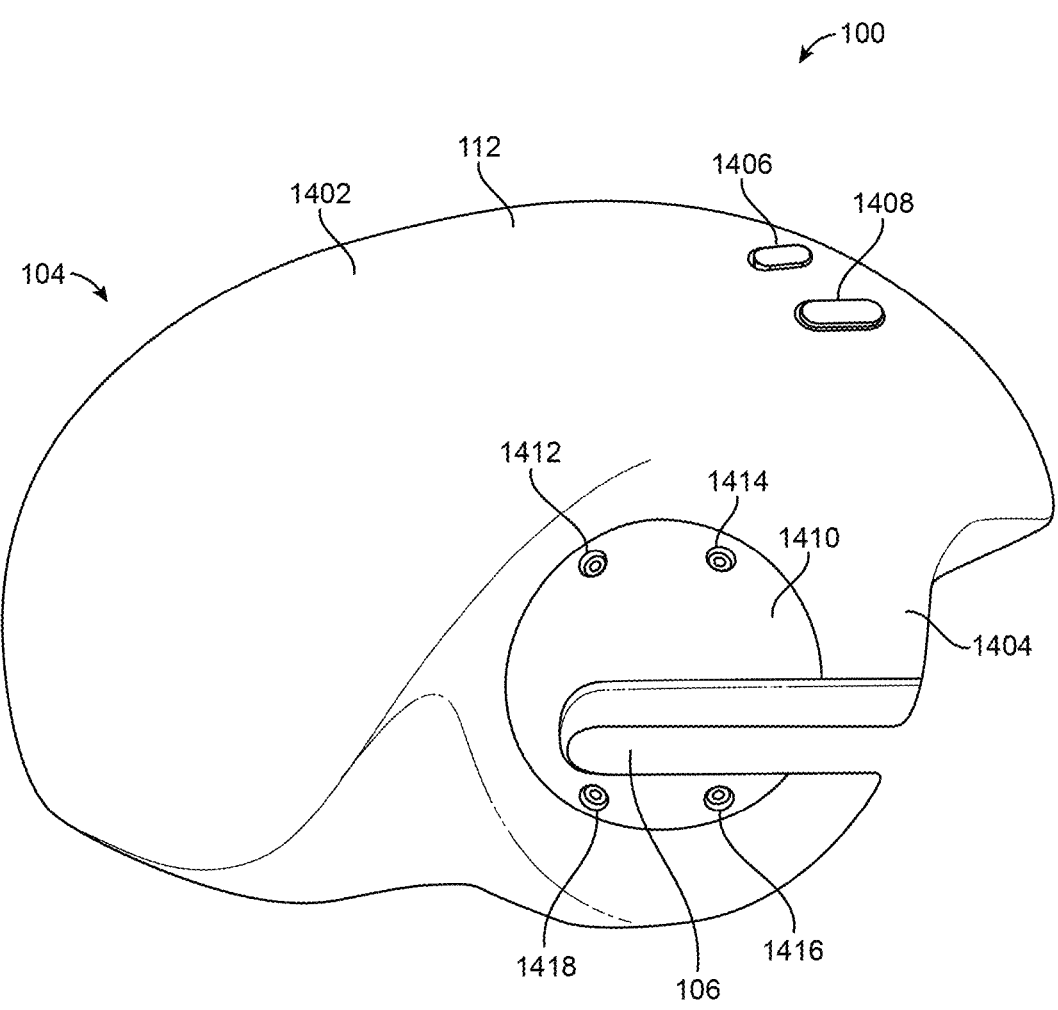
FIG. 14 illustrates a perspective view of a device providing a path for inserting a needle for performing medical procedures that is designed to facilitate use by a single user, in accordance with an embodiment of the present invention.

FIG. 14 illustrates a perspective view of device 100 in accordance with an embodiment in which ultrasound probe housing 104 is sized and shaped to facilitate use thereof by a single user. In particular, as shown in FIG. 14, ambient side 112 of ultrasound probe housing 104 includes a first portion 1402 and a second portion 1404 that is directly adjacent to first portion 1402. First portion 1402 is ergonomically shaped to fit at least a portion of a hand (in this case, the left hand) of a user. For example, first portion 1402 may be ergonomically shaped to fit within a cupped hand of a user, or a cupped portion of a hand of a user, with a relaxed, natural and low tension grip, thereby enabling the user to comfortably use said hand, or said portion of said hand, to adjust a position of device 100 as needed with respect to a body of a patient and/or hold device 100 in place against the body of the patient while performing a needle insertion. The shape of first portion 1402 of ambient side 112 may be contoured to maximize contact area with the user's hand, or the portion of the user's hand, to optimize control of device 100. The alternate hand of the user (in this case, the right hand) may then be used to perform a needle insertion through guide channel cut-out or aperture 106, which extends through ultrasound probe housing 104 from second portion 1404 of ambient side 112 to body side 114 (not visible in FIG. 14).

Needle guide assembly 108 may be present and connected to guide channel cut-out or aperture 106. For example, needle guide assembly 108 may be connected to guide channel cut-out or aperture 106 in any manner previously described. Needle guide assembly 108 may be adapted to receive needle 102 and allow needle 102 to slide along needle guide assembly 108 to perform needle insertion. Alternatively, needle guide assembly 108 may not be present and needle 102 may be hand-operated to perform an insertion through guide channel cut-out or aperture 106. In either case, after passing through guide channel cut-out or aperture 106 and upon insertion into the body of the patient, needle 102 will enter a field of view of ultrasound probes 105 within ultrasound probe housing 104.

As shown in FIG. 14, guide channel cut-out or aperture 106 may have an elongated shape to allow for greater needle angle and to provide a user with easier access to needle 102 and, if present, a catheter hub. In alternate embodiments, guide channel cut-out or aperture 106 may be formed in other shapes such as shallow, circular, conical, hyperboloid, etc. During use, a user's left-hand palm and fingers may be placed or rested on first portion 1402 of ambient side 112 of ultrasound probe housing 104 above guide channel cut-out or aperture 106 (relative to the perspective view of device shown in FIG. 14), while the user's left-hand thumb may either be placed or rested alongside the fingers above guide channel cut-out or aperture 106 (on first portion 1402) or placed or rested below (on the other side of) guide channel cut-out or aperture 106, on second portion 1404 of ambient side 112. In the former configuration, the user may insert needle 102 through guide channel cut-out or aperture 106 in an area adjacent to and to the left of their left-hand thumb, while in the latter configuration, the user may insert needle 102 through guide channel cut-out or aperture 106 in a gap or area defined by their left-hand forefinger and left-hand thumb.

As further shown in FIG. 14, first portion 1402 of ambient side 112 of ultrasound probe housing 104 may comprise a first finger-actuated control 1406 and a second finger-actuated control 1408. In the embodiment shown in FIG. 14, first finger-actuated control 1406 and second finger-actuated control 1408 each comprise a button; however, these finger-actuated controls may be implemented using different structures, such as but not limited to switches, toggles, wheels, touch-sensitive surfaces, reactive surfaces configured to respond to a material in a fingertip of a glove, or the like.

First finger-actuated control 1406 and second finger-actuated control 1408 may be used, for example, to power on or off device 100, to activate and/or control a particular functionality that may be provided by device 100, or to perform some other operation with respect to device 100. For example, with respect to activating and/or controlling a particular functionality that may be provided by device 100, and depending upon the implementation of device 100, first finger-actuated control 1406 and second finger-actuated control 1408 may be used to activate and/or control an image capture functionality of device 100, a video capture functionality of device 100, a functionality of device 100 that enables a user to cycle between different depths associated with images or video captured by device 100, or a functionality of device 100 that enables graphical overlays to be added to or removed from images or video captured by device 100, or that enables graphical overlays to be added to or removed from particular elements (e.g., needle 102, an internal target body location, an anatomical part of the body of the patient, or the like) that are identified within images or video captured by device 100. However, first finger-actuated control 1406 and second finger-actuated control 1408 may be used to activate and/or control other functionality of device 100 in other embodiments. First finger-actuated control 1406 and second finger-actuated control 1408 may be located in respective positions on first portion 1402 of ambient side 112 of ultrasound probe housing 104 such that they are proximal to the fingertips of the hand that the user is using to hold or move device 100 (in this case, their left hand). This enables the user to comfortably and easily activate the controls with the fingertips of the same hand that is holding or moving device 100 without having to release their grip on device 100. Additional finger-actuated controls with redundant or further functionality may be provided on device 100 within finger reach.

As still further shown in FIG. 14, second portion 1404 of ambient side 112 of ultrasound probe housing 104 may comprise a concave region 1410 that surrounds or partially surrounds guide channel cut-out or aperture 106. In some embodiments, a modular version of needle guide assembly 108 may be inserted into concave region 1410 and/or connected thereto. Such concave region 1410 thus may allow needle guide assembly 108 to be inserted within and/or connected to second portion 1404 of ambient side 112 of ultrasound probe housing 104 for subsequent use in performing a needle insertion. Concave region 1410 may be shaped to provide a desired range of movement of needle 102 and/or needle guide assembly 108 when used by an operator. Needle guide assembly 108 may be firmly affixed or may be a disposable unit removable upon completion of a procedure or at the convenience of the operator. Needle guide assembly 108 may further be sterile. In certain embodiments, concave region 1410 may be absent.

Device 100 shown in FIG. 14 also includes surface cameras 1412, 1414, 1416 and 1418 that are disposed within a perimeter sidewall of concave region 1410 of second portion 1404 of ultrasound probe housing 104 and proximate to guide channel cut-out or aperture 106. Surface cameras 1412, 1414, 1416 and 1418 may be situated such that each camera has a field of view that encompasses at least a portion of needle 102 as needle 102 passes through guide channel cut-out or aperture 106. Surface cameras 1412, 1414, 1416 and 1418 may be used to capture images or video of needle 102 that may be used to determine an angle of rotation of needle 102, whether needle 102 has been inserted into the body of the patient, a location of needle 102 for insertion into the body of the patient, or the like. Such images or video may also be processed instantaneously or near instantaneously by processor 602 for real-time display by display unit 610. Depending upon the implementation and the size/shape of needle guide assembly 108, the connection of needle guide assembly 108 to concave region 1410 may obscure a field of view of one or more of surface cameras 1412, 1414, 1416 and 1418, in which case those camera(s) may be rendered inoperable while needle guide assembly 108 is attached to concave region 1410. In alternate implementations, the connection of needle guide assembly 108 to concave region 1410 may not interfere with operation of surface cameras 1412, 1414, 1416 and 1418. In still other implementations, surface cameras may also be located in other locations on ultrasound probe housing 104 such as in other locations on first portion 1402 or second portion 1404 of ambient side 112 of ultrasound probe housing 104 or within guide channel cut-out or aperture 106, or may be located elsewhere, such as on needle guide assembly 108.

Figure 15:
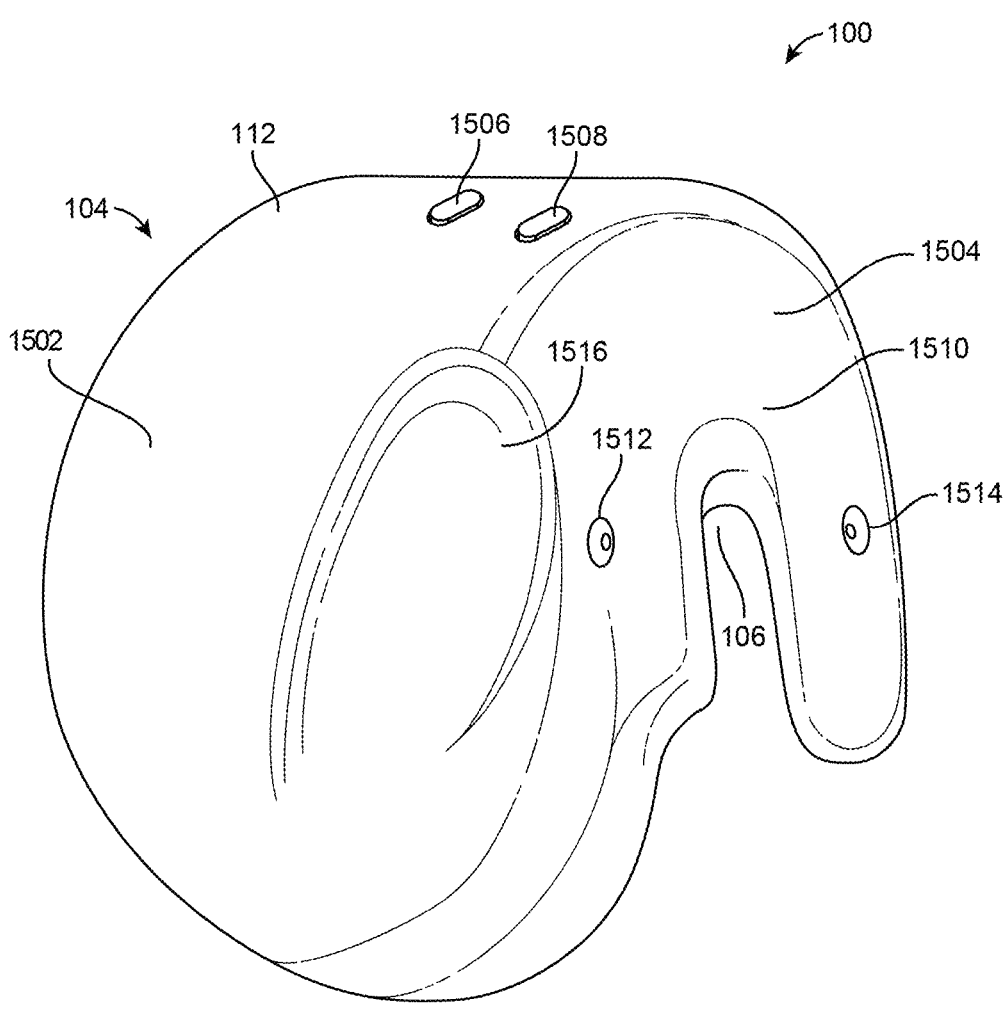
FIG. 15 illustrates a perspective view of a device providing a path for inserting a needle for performing medical procedures that is designed to facilitate use by a single user, in accordance with another embodiment of the present invention.

FIG. 15 depicts a perspective view of device 100 in accordance with another embodiment in which ultrasound probe housing 104 is sized and shaped to facilitate use thereof by a single user. As shown in FIG. 15, ambient side 112 of ultrasound probe housing 104 includes a first portion 1502 and a second portion 1504 that is directly adjacent to first portion 1502. First portion 1502 is ergonomically shaped to fit at least a portion of a hand (in this case, the left hand) of a user. For example, first portion 1502 may be ergonomically shaped to fit within a cupped hand of a user, or a cupped portion of a hand of a user, with a relaxed, natural and low tension grip, thereby enabling the user to comfortably use said hand, or said portion of said hand, to adjust a position of device 100 as needed with respect to a body of a patient and/or hold device 100 in place against the body of the patient while performing a needle insertion. The shape of first portion 1502 of ambient side 112 may be contoured to maximize contact area with the user's hand, or the portion of the user's hand, to optimize control of device 100. In addition, first portion 1502 of ambient side 112 of ultrasound probe housing 104 includes a depression 1516 that is adapted to fit a thumb of the at least a portion of the hand of the user when placed over first portion 1502. Thus, the user may comfortably rest their left-hand thumb within depression 1516 while using device 100. The alternate hand of the user (in this case, the right hand) may then be used to perform a needle insertion through guide channel cut-out or aperture 106, which extends through ultrasound probe housing 104 from second portion 1504 of ambient side 112 to body side 114 (not visible in FIG. 15).

Needle guide assembly 108 may be present and connected to guide channel cut-out or aperture 106. For example, needle guide assembly 108 may be connected to guide channel cut-out or aperture 106 in any manner previously described. Needle guide assembly 108 may be adapted to receive needle 102 and allow needle 102 to slide along needle guide assembly 108 to perform needle insertion. Alternatively, needle guide assembly 108 may not be present and needle 102 may be hand-operated to perform an insertion through guide channel cut-out or aperture 106. In either case, after passing through guide channel cut-out or aperture 106 and upon insertion into the body of the patient, needle 102 will enter a field of view of ultrasound probes 105 with ultrasound probe housing 104.

As shown in FIG. 15, guide channel cut-out or aperture 106 may have an elongated shape to allow for greater needle angle and to provide a user with easier access to needle 102 and, if present, a catheter hub. In alternate embodiments, guide channel cut-out or aperture 106 may be created in other shapes such as shallow, circular, conical, hyperboloid, etc.

As further shown in FIG. 15, first portion 1502 of ambient side 112 of ultrasound probe housing 104 may comprise a first finger-actuated control 1506 and a second finger-actuated control 1508. In the embodiment shown in FIG. 15, first finger-actuated control 1506 and second finger-actuated control 1508 each comprise a button; however, these finger-actuated controls may be implemented using different structures, such as but not limited to switches, toggles, wheels, touch-sensitive surfaces, reactive surfaces configured to respond to a material in a fingertip of a glove, or the like.

First finger-actuated control 1506 and second finger-actuated control 1508 may be used, for example, to power on or off device 100, to activate and/or control a particular functionality that may be provided by device 100, or to perform some other operation with respect to device 100. For example, with respect to activating and/or controlling a particular functionality that may be provided by device 100, and depending upon the implementation of device 100, first finger-actuated control 1506 and second finger-actuated control 1508 may be used to activate and/or control an image capture functionality of device 100, a video capture functionality of device 100, a functionality of device 100 that enables a user to cycle between different depths associated with images or videos captured by device 100, or a functionality of device 100 that enables graphical overlays to be added to or removed from images or videos captured by device 100, or that enables graphical overlays to be added to or removed from particular elements (e.g., needle 102, an internal target body location, an anatomical part of the body of the patient, or the like) that are identified within images or videos captured by device 100. However, first finger-actuated control 1506 and second finger-actuated control 1508 may be used to activate and/or control other functionality of device 100 in other embodiments. First finger-actuated control 1506 and second finger-actuated control 1508 may be located in respective positions on first portion 1502 of ambient side 112 of ultrasound probe housing 104 such that they are proximal to the fingertips of the hand that the user is using to hold or move device 100 (in this case, their left hand). This enables the user to comfortably and easily activate the controls with the fingertips of the same hand that is holding or moving device 100 with having to release their grip on device 100. A finger-actuated control may also be disposed within or proximate to depression 1516 such that it may activated with the user's thumb when resting in depression 1516. Additional finger-actuated controls with redundant or further functionality may be provided on device 100 within finger reach.

As still further shown in FIG. 15, second portion 1504 of ambient side 112 of ultrasound probe housing 104 may comprise a concave region 1510 that surrounds or partially surrounds guide channel cut-out or aperture 106. Concave region 1510 has a more open shape than concave region 1410 of the embodiment of FIG. 14, but may serve a similar purpose. For example, in some embodiments, a modular version of needle guide assembly 108 may be inserted into concave region 1510 and/or connected thereto. Such concave region 1510 thus may allow needle guide assembly 108 to be inserted within and/or connected to second portion 1504 of ambient side 112 of ultrasound probe housing 104 for subsequent use in performing a needle insertion. Concave region 1510 may be shaped to provide a desired range of movement of needle 102 and/or needle guide assembly 108 when used by an operator. As noted above, needle guide assembly 108 may be firmly affixed or may be a disposable unit removable upon completion of a procedure or at the convenience of the operator, and may further be sterile. In certain embodiments, concave region 1510 may be absent.

Device 100 shown in FIG. 15 also includes surface cameras 1512 and 1514 that are connected to second portion 1504 of ambient side 112 of ultrasound probe housing 104 within concave region 1510 and proximate to guide channel cut-out or aperture 106. Surface cameras 1512 and 1514 may be situated such that each camera has a field of view that encompasses at least a portion of needle 102 as needle 102 passes through guide channel cut-out or aperture 106. Surface cameras 1512 and 1514 may be used to capture images or video of needle 102 that may be used to determine an angle of rotation of needle 102, whether needle 102 has been inserted into the body of the patient, a location of needle 102 for insertion into the body of the patient, or the like. Such images or video may also be processed instantaneously or near-instantaneously by processor 602 for real-time display by display unit 610. Depending upon the implementation and the size/shape of needle guide assembly 108, the connection of needle guide assembly 108 to concave region 1510 may obscure a field of view of one or more of surface cameras 1512 and 1514, in which case those camera(s) may be rendered inoperable while needle guide assembly 108 is attached to concave region 1510. In alternate implementations, the connection of needle guide assembly 108 to concave region 1510 may not interfere with operation of surface cameras 1512 and 1514. In still other implementations, surface cameras may also be located in other locations on ultrasound probe housing 104 such as in other locations on first portion 1502 or second portion 1504 of ambient side 112 of ultrasound probe housing 104 or within guide channel cut-out or aperture 106, or may be located elsewhere, such as on needle guide assembly 108.

Figure 16A:
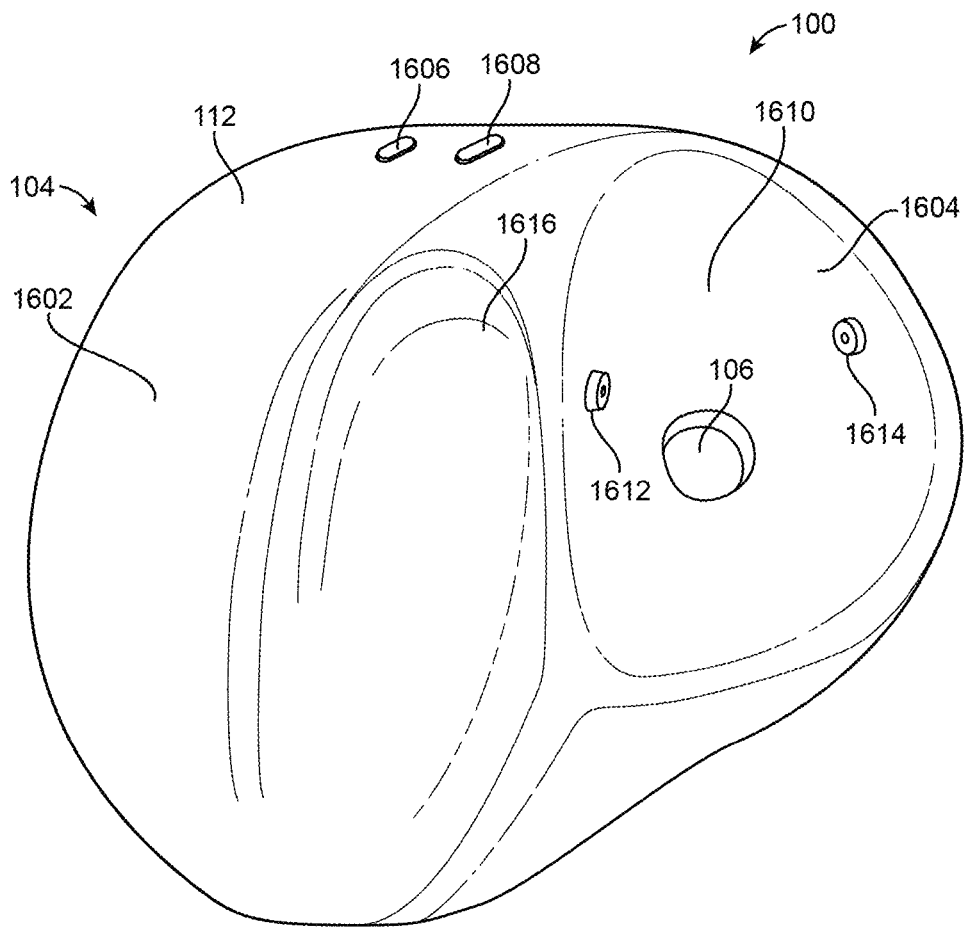
FIG. 16A illustrates a perspective view of a device providing a path for inserting a needle for performing medical procedures that is designed to facilitate use by a single user, in accordance with yet another embodiment of the present invention.

FIG. 16A depicts a perspective view of device 100 in accordance with yet another embodiment in which ultrasound probe housing 104 is sized and shaped to facilitate use thereof by a single user. As shown in FIG. 16A, ambient side 112 of ultrasound probe housing 104 includes a first portion 1602 and a second portion 1604 that is directly adjacent to first portion 1602. First portion 1602 is ergonomically shaped to fit at least a portion of a hand (in this case, the left hand) of a user. For example, first portion 1602 may be ergonomically shaped to fit within a cupped hand of a user, or a cupped portion of a hand of a user, with a relaxed, natural and low tension grip, thereby enabling the user to comfortably use said hand, or said portion of said hand, to adjust a position of device 100 as needed with respect to a body of a patient and/or hold device 100 in place against the body of the patient while performing a needle insertion. The shape of first portion 1602 of ambient side 112 may be contoured to maximize contact area with the user's hand, or the portion of the user's hand, to optimize control of device 100. In addition, first portion 1602 of ambient side 112 of ultrasound probe housing 104 includes a depression 1616 that is adapted to fit a thumb of the at least a portion of the hand of the user when placed over first portion 1602. Thus, the user may comfortably rest their left-hand thumb within depression 1616 while using device 100. The alternate hand of the user (in this case, the right hand) may then be used to perform a needle insertion through guide channel cut-out or aperture 106, which extends through ultrasound probe housing 104 from second portion 1604 of ambient side 112 to body side 114 (not visible in FIG. 16A).

Needle guide assembly 108 may be present and connected to guide channel cut-out or aperture 106. For example, needle guide assembly 108 may be connected to guide channel cut-out or aperture 106 in any manner previously described. Needle guide assembly 108 may be adapted to receive needle 102 and allow needle 102 to slide along needle guide assembly 108 to perform the needle insertion. Alternatively, needle guide assembly 108 may not be present and needle 102 may be hand-operated to perform an insertion through guide channel cut-out or aperture 106. In either case, after passing through guide channel cut-out or aperture 106 and upon insertion into the body of the patient, needle 102 will enter a field of view of ultrasound probes 105 with ultrasound probe housing 104.

As shown in FIG. 16A, guide channel cut-out or aperture 106 may be of a circular shape. In alternate embodiments, guide channel cut-out 106 may be created in other shapes such as elongated, shallow, conical, hyperboloid, etc.

As further shown in FIG. 16A, first portion 1602 of ambient side 112 of ultrasound probe housing 104 may comprise a first finger-actuated control 1606 and a second finger-actuated control 1608. In the embodiment shown in FIG. 16A, first finger-actuated control 1606 and second finger-actuated control 1608 each comprise a button; however, these finger-actuated controls may be implemented using different structures, such as but not limited to switches, toggles, wheels, touch-sensitive surfaces, reactive surfaces configured to respond to a material in a fingertip of a glove, or the like.

First finger-actuated control 1606 and second finger-actuated control 1608 may be used, for example, to power on or off device 100, to activate and/or control a particular functionality that may be provided by device 100, or to perform some other operation with respect to device 100. For example, with respect to activating and/or controlling a particular functionality that may be provided by device 100, and depending upon the implementation of device 100, first finger-actuated control 1606 and second finger-actuated control 1608 may be used to activate and/or control an image capture functionality of device 100, a video capture functionality of device 100, a functionality of device 100 that enables a user to cycle between different depths associated with images or videos captured by device 100, or a functionality of device 100 that enables graphical overlays to be added to or removed from images or videos captured by device 100, or that enables graphical overlays to be added to or removed from particular elements (e.g., needle 102, an internal target body location, an anatomical part of the body of the patient, or the like) that are identified within images or videos captured by device 100. However, first finger-actuated control 1606 and second finger-actuated control 1608 may be used to activate and/or control other functionality of device 100 in other embodiments. First finger-actuated control 1606 and second finger-actuated control 1608 may be located in respective positions on first portion 1602 of ambient side 112 of ultrasound probe housing 104 such that they are proximal to the fingertips of the hand that the user is using to hold or move device 100 (in this case, their left hand). This enables the user to comfortably and easily activate the controls with the fingertips of the same hand that is holding or moving device 100 without having to release their grip on device 100. A finger-actuated control may also be disposed within or proximate to depression 1616 such that it may be activated with the user's thumb when resting in depression 1616. Additional finger-actuated controls with redundant or further functionality may be provided on device 100 within finger reach.

As still further shown in FIG. 16A, second portion 1604 of ambient side 112 of ultrasound probe housing 104 may comprise a concave region 1610 that surrounds or partially surrounds guide channel cut-out or aperture 106. Concave region 1610 has a more open shape than concave region 1410 of the embodiment of FIG. 4, but may serve a similar purpose. For example, in some embodiments, a modular version of needle guide assembly 108 may be inserted into concave region 1610 and/or connected thereto. Such concave region 1610 may allow needle guide assembly 108 to be inserted within and/or connected to second portion 1604 of ambient side 112 of ultrasound probe housing 104 for subsequent use in performing a needle insertion. Concave region 1610 may be shaped to provide a desired range of movement of needle 102 and/or needle guide assembly 108 when used by an operator. As noted above, needle guide assembly 108 may be firmly affixed or may be a disposable unit removable upon completion of a procedure or at the convenience of the operator, and may further be sterile. In certain embodiments, concave region 1610 may be absent.

Device 100 shown in FIG. 16A also includes surface cameras 1612 and 1614 that are connected to second portion 1604 of ambient side 112 of ultrasound probe housing 104 within concave region 1610 and proximate to guide channel cut-out or aperture 106. Surface cameras 1612 and 1614 may be situated such that each camera has a field of view that encompasses at least a portion of needle 102 as needle 102 passes through guide channel cut-out or aperture 106. Surface cameras 1612 and 1614 may be used to capture images or video of needle 102 that may be used to determine an angle of rotation of needle 102, whether needle 102 has been inserted into the body of the patient, a location of needle 102 for insertion into the body of the patient, or the like. Such images or video may also be processed instantaneously or near-instantaneously by processor 602 for real-time display by display unit 610. Depending upon the implementation and the size/shape of needle guide assembly 108, the connection of needle guide assembly 108 to concave region 1610 may obscure a field of view of one or more of surface cameras 1612 and 1614, in which case those camera(s) may be rendered inoperable while needle guide assembly 108 is attached to concave region 1610. In alternate implementations, the connection of needle guide assembly 108 to concave region 1610 may not interfere with operation of surface cameras 1612 and 1614. In still other implementations, surface cameras may also be located in other locations on ultrasound probe housing 104 such as in other locations on first portion 1602 or second portion 1604 of ambient side 112 of ultrasound probe housing 104 or within guide channel cut-out or aperture 106, or may be located elsewhere, such as on needle guide assembly 108.

Figure 16B:
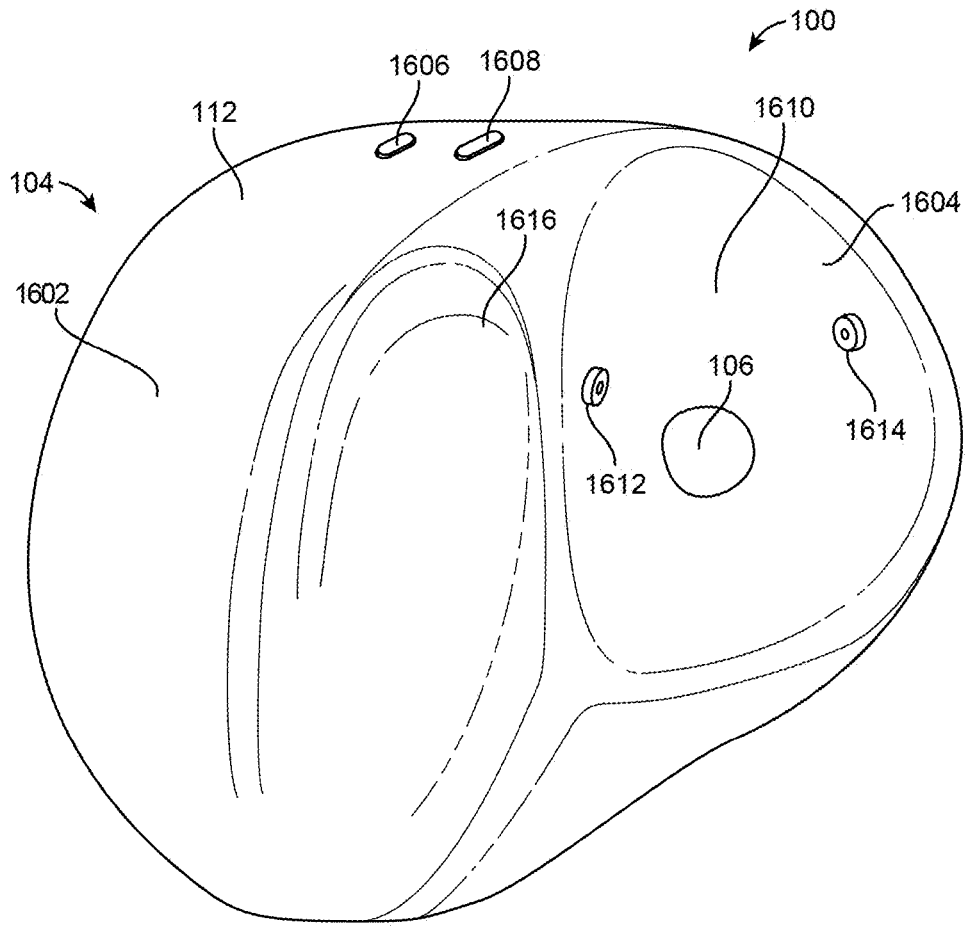
FIG. 16B illustrates a perspective view of a device providing a path for inserting a needle for performing medical procedures that is designed to facilitate use by a single user, in accordance with yet another embodiment of the present invention.

While guide channel cut-out or aperture 106 is shown having a particular depth or height in FIG. 16A, it will be appreciated that the depth of guide channel cut-out or aperture 106 can vary. By way of example, FIG. 16B depicts an alternate implementation of the embodiment of FIG. 16A in which concave region 1610 of second portion 1604 of ambient side 112 of ultrasound probe housing 104 tapers downward to meet guide channel cut-out or aperture 106 at a thinnest point that is almost flush with the body of the patient. As such, in an embodiment in which concave region 1610 is present, it may appear to run directly to the body of the patient.

Figure 16C:
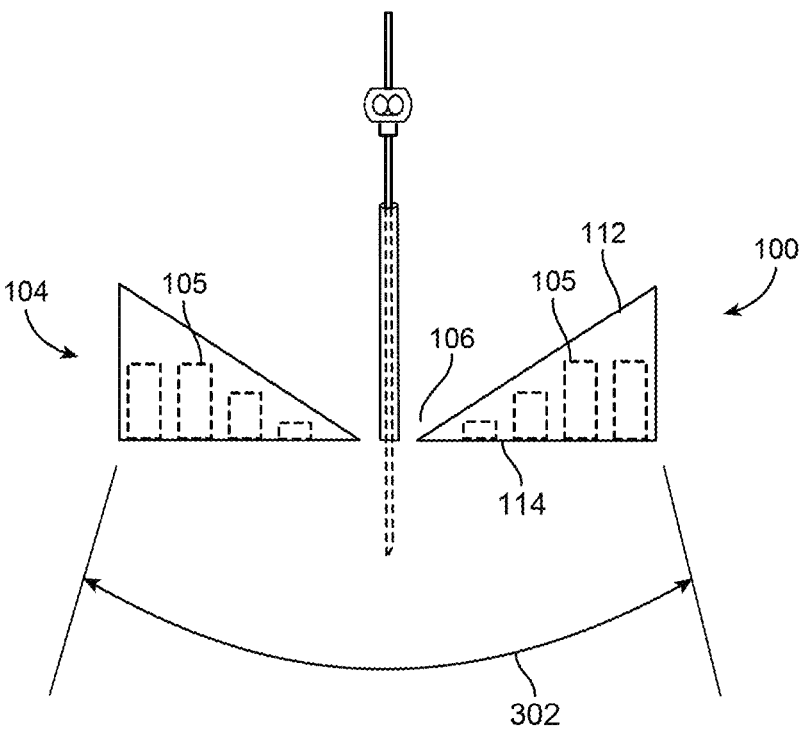
FIG. 16C illustrates a front view of a device in accordance with an embodiment of the present invention.

FIG. 16C illustrates a partial front view of device 100 in accordance with an embodiment of the present invention. FIG. 16C may be a partial front view, for example and without limitation, of the embodiment of device 100 described above in reference to FIG. 16B. As shown in FIG. 16C, owing to the presence of concave region 1610 that surrounds guide channel-cut out or aperture 106, the distance between ambient side 112 and body side 114 of ultrasound probe housing gradually decreases as ambient side 112 approaches guide-channel cut out or aperture 106. That is to say, the profile or depth of ultrasound probe housing 104 gradually decreases toward guide channel cut-out or aperture 106 in a region surrounding guide channel cut-out or aperture 106. Such a design effectively reduces the depth of guide channel cut-out or aperture 106. This in turn can provide greater range of movement of needle 102 with respect to guide channel cut-out or aperture 106. By effectively reducing the depth of guide channel cut-out or aperture 106, such a design can also improve the visibility of needle 102 during needle insertion. It is noted that such a design may be implemented in any of the embodiments of device 100 described herein.

As further shown in FIG. 16C, smaller, lower or varied power ultrasound probes 105, including chip-based transducers, or micromachined ultrasound transducers (MUTs) that use silicon chips to convert voltage to resonance, may be disposed within the lower profile portion of ultrasound probe housing 104 while ultrasound probes 105 that benefit from greater space may be disposed within the higher profile portion of ultrasound probe housing 104. Such an approach may be motivated, for example, by the reduced amount of internal space within the lower profile portion relative to the higher profile portion. However, since the lower profile portion of ultrasound probe housing 104 is closest to the point of needle insertion into the body of the patient, the use of smaller, lower-power ultrasound probes in this portion of the device may be deemed acceptable. Such locational usage of transducers with varying viewing depths and resolutions (corresponding to frequency ranges, such as between 2.5 MHz to approximately 15 MHz) allows flexibility with regard to space required for needle movement and the need to visualize and track the needle as it progresses from point of entry to the target site. Transducers resolving at shallow depths may be used primarily to track needle 102 at the point of entry, and thus such probes may not need to provide the same depth of viewing as the probes disposed in the higher profile section.

In certain implementations, the higher profile portion of ultrasound probe housing 104 may be utilized to house relatively large internal components (e.g., a CPU and/or battery of device 100) that might not be accommodated (or easily accommodated) within the lower profile portion of ultrasound probe housing 104. In addition to providing more internal space within which to house such components, the higher profile portion of ultrasound probe housing 104 may also provide enough additional space to include one or more heat exchange elements (e.g., vents, heat sinks), examples of which were previously described.

Figure 16D:
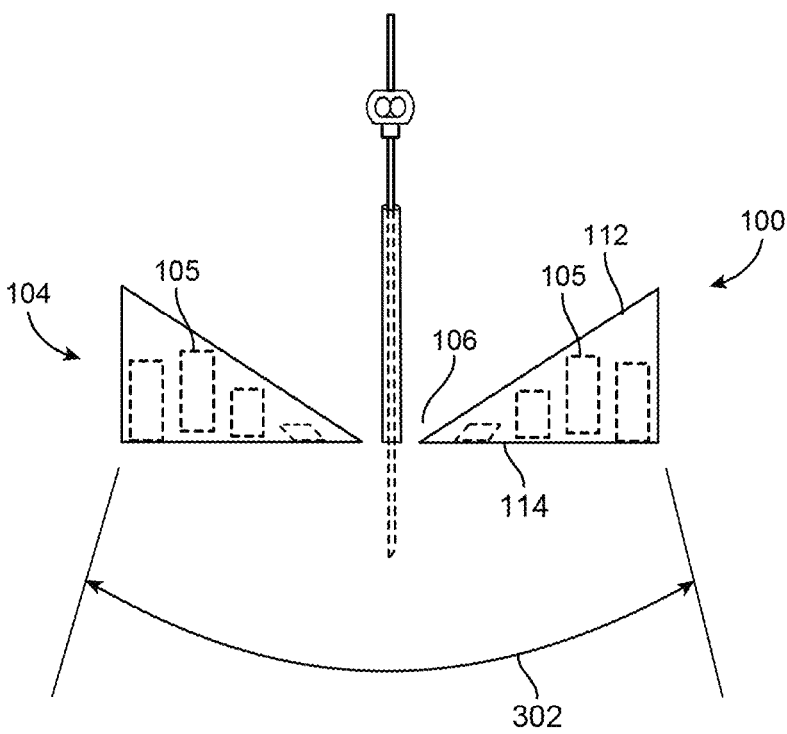
FIG. 16D illustrates a front view of a device in accordance with an embodiment of the present invention.

In the embodiment of FIG. 16C, ultrasound probes 105 are positioned perpendicular to and at a uniform distance from body side 114 of ultrasound probe housing 104. As shown by example in FIG. 16D, the ultrasound probes 105 may be positioned within ultrasound probe housing 104 to alter the viewable image of field 302. In certain formats, ultrasound probes 105 may be angled within ultrasound probe housing 104 to optimize the viewable image at the site of needle penetration beneath ultrasound probe housing 104. Likewise, ultrasound probes 105 may be positioned perpendicular to and at varying distances from body side 114 of ultrasound probe housing 104 to give a wider viewable image area. Ultrasound probe housing 104 may also contain a mixed array of angled and perpendicular probes 105 to alter viewable image geometries. For example, ultrasound probe housing may contain different angled probes 105 that are positioned at different distances from body side 114. It would be readily apparent to those skilled in the art that various types and shapes of ultrasound probe housing 104 containing probes 105 may be envisioned without deviating from the scope of the present invention.

Although the foregoing discussion refers to certain types of transducers, persons skilled in the art will appreciate that ultrasound probes 105 may be implemented using any suitable transducer types, including but by no means limited to 2D or 3D linear transducers, curved transducers, phased array transducers (including piezoelectric type and MUTs, such as pMUTs and cMUTs), or the like, as well as any combination thereof.

FIGS. 17A, 17B, 17C and 17D depict various perspective views of device 100 in accordance with a further embodiment in which ultrasound probe housing 104 is sized and shaped to facilitate use thereof by a single user. As was the case with the previously-described embodiments of FIGS. 14-16, ambient side 112 of ultrasound probe housing 104 includes a first portion 1702 and a second portion 1704 that is directly adjacent to first portion 1702. First portion 1702 is ergonomically shaped to fit at least a portion of a hand (in this case, the left hand) of a user. For example, first portion 1702 may be ergonomically shaped to fit within a hand of a user, or a portion of a hand of a user, with a relaxed, natural and low tension grip, thereby enabling the user to comfortably use said hand to adjust a position of device 100 as needed with respect to a body of a patient and/or hold device 100 in place against the body of the patient while performing a needle insertion. The shape of first portion 1702 of ambient side 112 may be contoured to maximize contact area with the user's hand, or the portion of the user's hand, to optimize control of device 100. In addition, first portion 1702 of ambient side 112 of ultrasound probe housing 104 may include a depression 1716 (visible in FIG. 17D) that is adapted to fit a thumb of the at least a portion of the hand of the user when placed over first portion 1702. Thus, the user may comfortably rest their left-hand thumb within depression 1716 while using device 100. The alternate hand of the user (in this case, the right hand) may then be used to perform a needle insertion through guide channel cut-out or aperture 106, which extends through ultrasound probe housing 104 from second portion 1704 of ambient side 112 to body side 114.

Needle guide assembly 108 may be present and connected to guide channel cut-out or aperture 106. For example, needle guide assembly 108 may be connected to guide channel cut-out or aperture 106 in any manner previously described. Needle guide assembly 108 may be adapted to receive needle 102 and allow needle 102 to slide along needle guide assembly 108 to perform needle insertion. Alternatively, needle guide assembly 108 may not be present and needle 102 may be hand-operated to perform an insertion through guide channel cut-out or aperture 106. In either case, after passing through guide channel cut-out or aperture 106 and upon insertion into the body of the patient, needle 102 will enter a field of view of ultrasound probes 105 within ultrasound probe housing 104.

As shown in FIGS. 17A-17D, guide channel cut-out or aperture 106 may have an elongated shape to allow for greater needle angle and to provide a user with easier access to needle 102 and, if present, a catheter hub. In alternate embodiments, guide channel cut-out 106 may be formed in other shapes such as shallow, circular, conical, hyperboloid, etc.

Although not shown in FIGS. 17A-17D, first portion 1702 of ambient side 112 of ultrasound probe housing 104 may comprise a first finger-actuated control and a second finger-actuated control. The first finger-actuated control and the second finger-actuated control may be used, for example, to power on or off device 100, to activate and/or control a particular functionality that may be provided by device 100, or to perform some other operation with respect to device 100. For example, with respect to activating and/or controlling a particular functionality that may be provided by device 100, and depending upon the implementation of device 100, the first finger-actuated control and the second finger-actuated control may be used to activate and/or control an image capture functionality of device 100, a video capture functionality of device 100, a functionality of device 100 that enables a user to cycle between different depths associated with images or video captured by device 100, or a functionality of device 100 that enables graphical overlays to be added to or removed from images or video captured by device 100, or that enables graphical overlays to be added to or removed from particular elements (e.g., needle 102, an internal target body location, an anatomical part of the body of the patient, or the like) that are identified within images or video captured by device 100. However, the first finger-actuated control and the second finger-actuated control may be used to activate and/or control other functionality of device 100 in other embodiments. The first finger-actuated control and the second finger-actuated control may be located in respective positions on first portion 1702 of ambient side 112 of ultrasound probe housing 104 such that they are proximal to the fingertips of the hand that the user is using to hold or move device 100 (in this case, their left hand). This enables the user to comfortably and easily activate the controls with the fingertips of the same hand that is holding or moving device 100 without having to release their grip on device 100. When a thumb depression is present on first portion 1702, a finger-actuated control may also be disposed within or proximate to the depression such that it may be activated with the user's thumb when resting in the depression. Additional finger-actuated controls with redundant or further functionality may be provided on device 100 within finger reach.

Figure 17A:
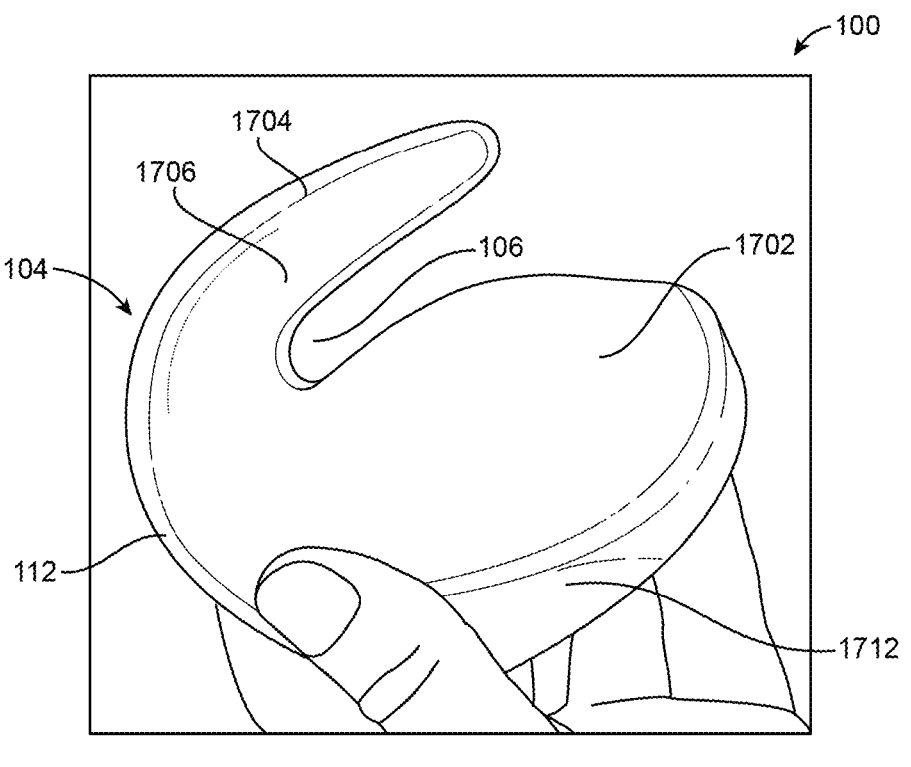
FIGS. 17A, 17B, 17C and 17D illustrate perspective views of a device providing a path for inserting a needle for performing medical procedures that is designed to facilitate use by a single user, in accordance with a further embodiment of the present invention.
Figure 17B:
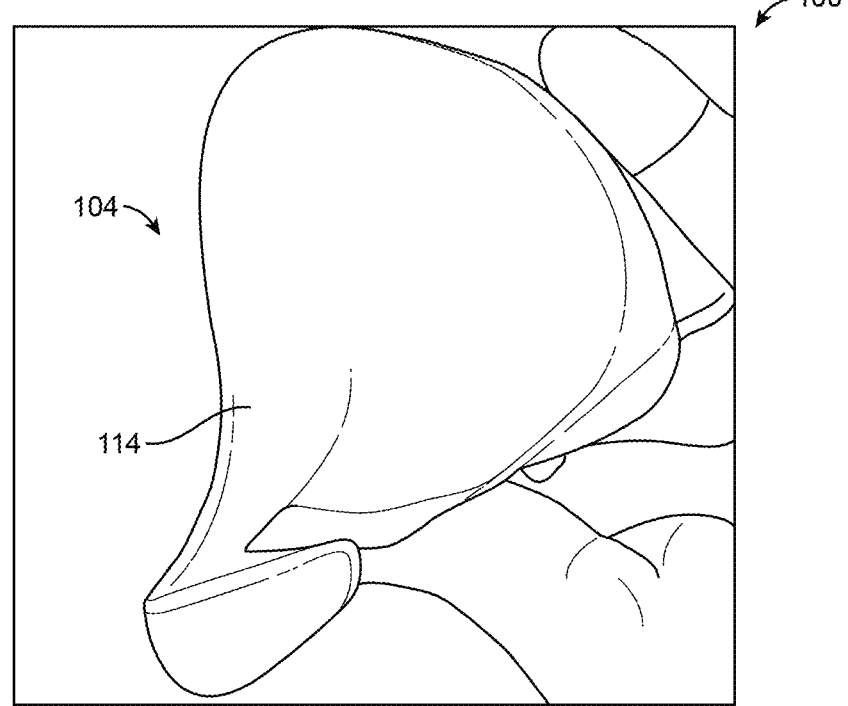
Figures 17C, 17D:
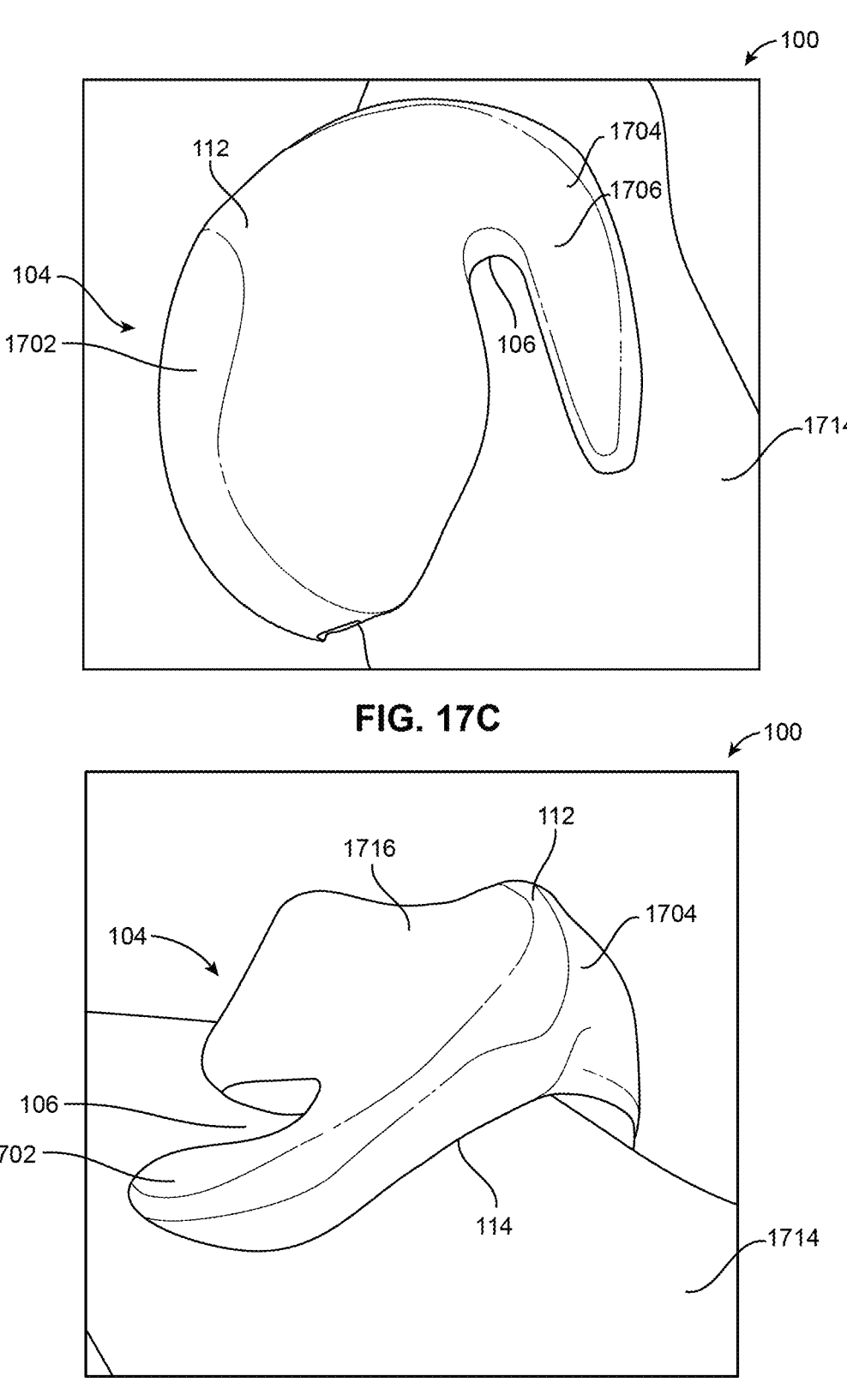

As still further shown in FIGS. 17A, 17C and 17D, second portion 1704 of ambient side 112 of ultrasound probe housing 104 may comprise a concave region 1706 that surrounds or partially surrounds guide channel cut-out or aperture 106. Concave region 1706 has a more open shape than concave region 1410 of the embodiment of FIG. 14, but may serve a similar purpose. For example, in some embodiments, a modular version of needle guide assembly 108 may be inserted into concave region 1706 and/or connected thereto. Such concave region 1706 thus may allow needle guide assembly 108 to be inserted within and/or connected to second portion 1704 of ambient side 112 of ultrasound probe housing 104 for subsequent use in performing a needle insertion. Concave region 1706 may be shaped to provide a desired range of movement of needle 102 and/or needle guide assembly 108 when used by an operator. As noted above, needle guide assembly 108 may be firmly affixed or may be a disposable unit removable upon completion of a procedure or at the convenience of the operator, and may further be sterile. In certain embodiments, concave region 1706 may be absent.

Device 100 shown in FIGS. 17A-17D may also include one or more surface cameras that are connected to second portion 1704 of ambient side 112 of ultrasound probe housing 104 within concave region 1706 and proximate to guide channel cut-out or aperture 106. Such surface camera(s) may be situated such that each camera has a field of view that encompasses at least a portion of needle 102 as needle 102 passes through guide channel cut-out or aperture 106. Such surface camera(s) may be used to capture images of video of needle 102 that may be used to determine an angle of rotation of needle 102, whether needle 102 has been inserted into the body of the patient, a location of needle 102 for insertion into the body of the patient, or the like. Such images or video may also be processed instantaneously or near-instantaneously by processor 602 for real-time display by display unit 610. Depending upon the implementation and the size/shape of needle guide assembly 108, the connection of needle guide assembly 108 to concave region 1706 may obscure a field of view of one or more of the surface cameras, in which case those camera(s) may be rendered inoperable while needle guide assembly 108 is attached to concave region 1706. In alternate implementations, the connection of needle guide assembly 108 to concave region 1706 may not interfere with operation of the surface camera(s). In still other implementations, surface cameras may also be located in other locations on ultrasound probe housing 104 such as in other locations on first portion 1702 or second portion 1704 of ambient side 112 of ultrasound probe housing 104 or within guide channel cut-out or aperture 106, or may be located elsewhere, such as on needle guide assembly 108.

As further shown in FIGS. 17A-17D, body side 114 of ultrasound probe housing 104 may be contoured to fit on a part of the body of the patient, such as but not limited to a limb of the body of the patient. For example, and as shown in FIGS. 17C and 17D, body side 114 of ultrasound probe housing 104 may be curved so that body side 114 contours around the inside of an arm 1714 of the patient allowing needle 102 access through guide channel cut-out or aperture 106. This may further enable device 100 to wrap around arm 1714 of the patient and potentially be held in place that way.

Figure 18:
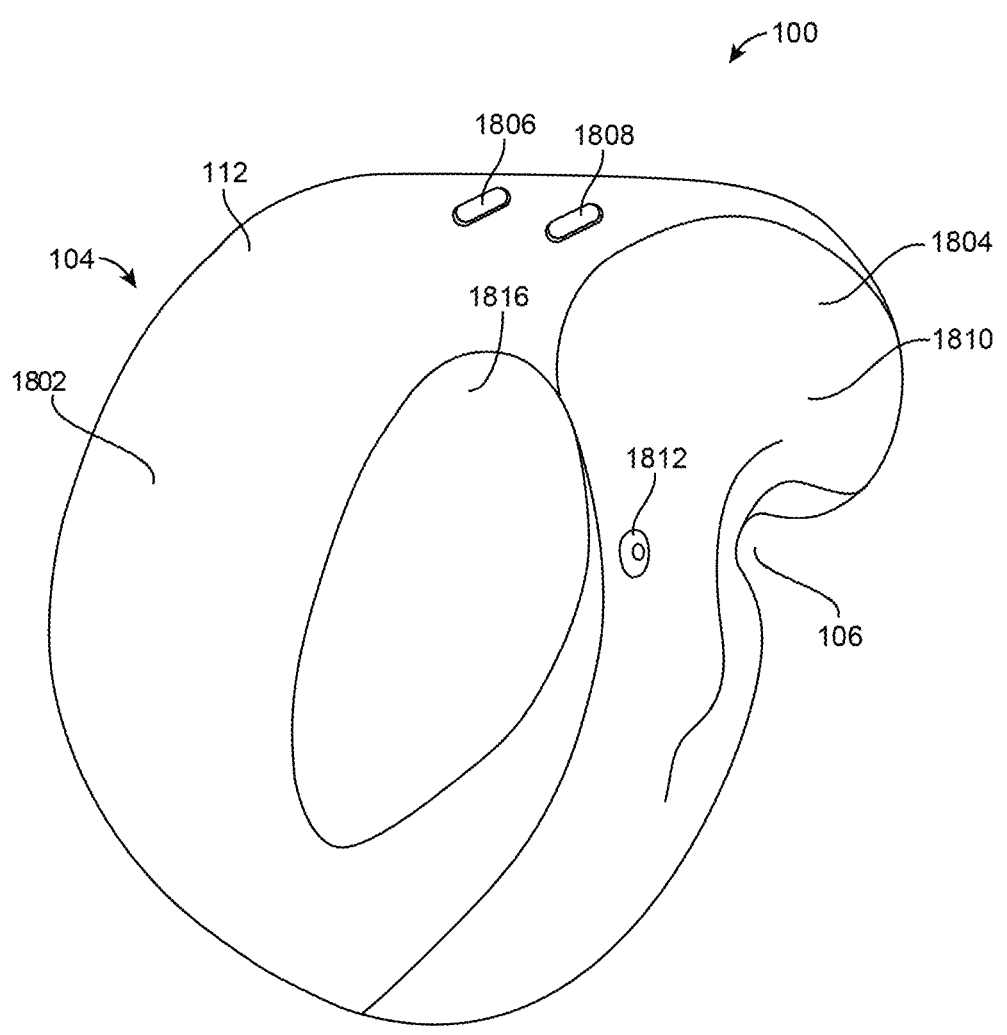
FIG. 18 illustrates a perspective view of a device providing a path for inserting a needle for performing medical procedures that is designed to facilitate use by a single user, in accordance with yet another embodiment of the present invention.

FIG. 18 depicts a perspective view of device 100 in accordance with another embodiment in which ultrasound probe housing 104 is sized and shaped to facilitate use thereof by a single user. As shown in FIG. 18, ambient side 112 of ultrasound probe housing 104 includes a first portion 1802 and a second portion 1804 that is directly adjacent to first portion 1802. First portion 1802 is ergonomically shaped to fit at least a portion of a hand (in this case, the left hand) of a user. For example, first portion 1802 may be ergonomically shaped to fit within a cupped hand of a user, or a cupped portion of a hand of a user, with a relaxed, natural and low tension grip, thereby enabling the user to comfortably use said hand, or said portion of said hand, to adjust a position of device 100 as needed with respect to a body of a patient and/or hold device 100 in place against the body of the patient while performing a needle insertion. The shape of first portion 1802 of ambient side 112 may be contoured to maximize contact area with the user's hand, or the portion of the user's hand, to optimize control of device 100. In addition, first portion 1802 of ambient side 112 of ultrasound probe housing 104 includes a depression 1816 that is adapted to fit a thumb of the at least a portion of the hand of the user when placed over first portion 1802. Thus, the user may comfortably rest their left-hand thumb within depression 1816 while using device 100. The alternate hand of the user (in this case, the right hand) may then be used to perform a needle insertion through guide channel cut-out or aperture 106, which extends through ultrasound probe housing 104 from second portion 1804 of ambient side 112 to body side 114 (not visible in FIG. 18).

In the embodiment of FIG. 18, guide channel cut-out or aperture 106 is a relatively shallow indent that is inset within a perimeter of ultrasound probe housing 104 and passes from second portion 1804 of ambient side 112 to body side 114 (not shown in FIG. 18). Such an embodiment may allow for greater range of movement of needle 102 with respect to guide channel cut-out or aperture 106, while still enabling needle 102 to be passed through guide channel cut-out or aperture 106 in a manner that enables it to appear within a field of view of ultrasound probes 105 of ultrasound probe housing 104 when inserted into the body of the patient. The embodiment of FIG. 18 may be used without needle guide assembly 108. Alternatively, needle guide assembly 108 may be adapted to connect to concave region 1810 and/or guide channel cut-out or aperture 106 so that it may be utilized to help guide and/or stabilize needle 102 during needle insertion. In alternate embodiments, guide channel cut-out 106 may be created in other shapes such as elongated, circular, conical, hyperboloid, etc.

As further shown in FIG. 18, first portion 1802 of ambient side 112 of ultrasound probe housing 104 may comprise a first finger-actuated control 1806 and a second finger-actuated control 1808. In the embodiment shown in FIG. 18, first finger-actuated control 1806 and second finger-actuated control 1808 each comprise a button; however, these finger-actuated controls may be implemented using different structures, such as but not limited to switches, toggles, wheels, touch-sensitive surfaces, reactive surfaces configured to respond to a material in a fingertip of a glove, or the like.

First finger-actuated control 1806 and second finger-actuated control 1808 may be used, for example, to power on or off device 100, to activate and/or control a particular functionality that may be provided by device 100, or to perform some other operation with respect to device 100. For example, with respect to activating and/or controlling a particular functionality that may be provided by device 100, and depending upon the implementation of device 100, first finger-actuated control 1806 and second finger-actuated control 1808 may be used to activate and/or control an image capture functionality of device 100, a video capture functionality of device 100, a functionality of device 100 that enables a user to cycle between different depths associated with images or videos captured by device 100, or a functionality of device 100 that enables graphical overlays to be added to or removed from images or videos captured by device 100, or that enables graphical overlays to be added to or removed from particular elements (e.g., needle 102, an internal target body location, an anatomical part of the body of the patient, or the like) that are identified within images or videos captured by device 100. However, first finger-actuated control 1806 and second finger-actuated control 1808 may be used to activate and/or control other functionality of device 100 in other embodiments. First finger-actuated control 1806 and second finger-actuated control 1808 may be located in respective positions on first portion 1802 of ambient side 112 of ultrasound probe housing 104 such that they are proximal to the fingertips of the hand that the user is using to hold or move device 100 (in this case, their left hand). This enables the user to comfortably and easily activate the controls with the fingertips of the same hand that is holding or moving device 100 without having to release their grip on device 100. A finger-actuated control may also be disposed within or proximate to depression 1816 such that it may be activated with the user's thumb when resting in depression 1816. Additional finger-actuated controls with redundant or further functionality may be provided on device 100 within finger reach.

As still further shown in FIG. 18, second portion 1804 of ambient side 112 of ultrasound probe housing 104 may comprise a concave region 1810 that surrounds or partially surrounds guide channel cut-out or aperture 106. Concave region 1810 has a more open shape than concave region 1410 of the embodiment of FIG. 14, but may serve a similar purpose. For example, in some embodiments, a modular version of needle guide assembly 108 may be inserted into concave region 1810 and/or connected thereto. Such concave region 1810 may allow needle guide assembly 108 to be inserted within and/or connected to second portion 1804 of ambient side 112 of ultrasound probe housing 104 for subsequent use in performing a needle insertion. Concave region 1810 may be shaped to provide a desired range of movement of needle 102 and/or needle guide assembly 108 when used by an operator. As noted above, needle guide assembly 108 may be firmly affixed or may be a disposable unit removable upon completion of a procedure or at the convenience of the operator, and may further be sterile. In certain embodiments, concave region 1810 may be absent.

Device 100 shown in FIG. 18 also includes a surface camera 1812 that is connected to second portion 1804 of ambient side 112 of ultrasound probe housing 104 within concave region 1810 and proximate to guide channel cut-out or aperture 106. Surface camera 1812 may be situated such that it has a field of view that encompasses at least a portion of needle 102 as needle 102 passes through guide channel cut-out or aperture 106. Surface camera 1812 may be used to capture images or video of needle 102 that may be used to determine an angle of rotation of needle 102, whether needle 102 has been inserted into the body of the patient, a location of needle 102 for insertion into the body of the patient, or the like. Such images or video may also be processed instantaneously or near-instantaneously by processor 602 for real-time display by display unit 610. Depending upon the implementation and the size/shape of needle guide assembly 108, the connection of needle guide assembly 108 to concave region 1810 may obscure a field of view of surface camera 1812, in which case that camera may be rendered inoperable while needle guide assembly 108 is attached to concave region 1810. In alternate implementations, the connection of needle guide assembly 108 to concave region 1810 may not interfere with operation of surface camera 1812. In still other implementations, surface cameras may also be located in other locations on ultrasound probe housing 104 such as in other locations on first portion 1802 or second portion 1804 of ambient side 112 of ultrasound probe housing 104 or within guide channel cut-out or aperture 106, or may be located elsewhere, such as on needle guide assembly 108.

Figure 19:
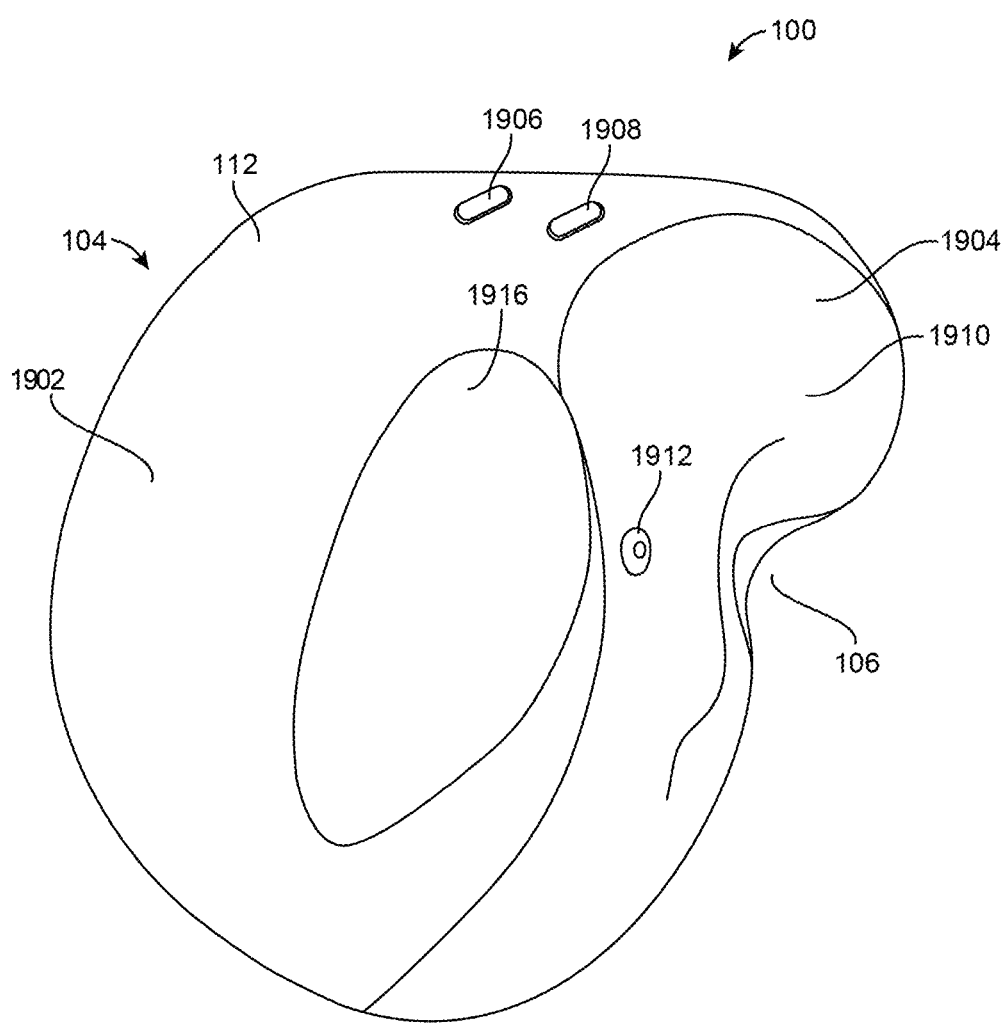
FIG. 19 illustrates a perspective view of a device providing a path for inserting a needle for performing medical procedures that is designed to facilitate use by a single user, in accordance with yet another embodiment of the present invention.

FIG. 19 depicts a perspective view of device 100 in accordance with another embodiment in which ultrasound probe housing 104 is sized and shaped to facilitate use thereof by a single user. As shown in FIG. 19, ambient side 112 of ultrasound probe housing 104 includes a first portion 1902 and a second portion 1904 that is directly adjacent to first portion 1902. First portion 1902 is ergonomically shaped to fit at least a portion of a hand (in this case, the left hand) of a user. For example, first portion 1902 may be ergonomically shaped to fit within a cupped hand of a user, or a cupped portion of a hand of a user, with a relaxed, natural and low tension grip, thereby enabling the user to comfortably use said hand, or said portion of said hand, to adjust a position of device 100 as needed with respect to a body of a patient and/or hold device 100 in place against the body of the patient while performing a needle insertion. The shape of first portion 1902 of ambient side 112 may be contoured to maximize contact area with the user's hand, or the portion of the user's hand, to optimize control of device 100. In addition, first portion 1902 of ambient side 112 of ultrasound probe housing 104 includes a depression 1916 that is adapted to fit a thumb of the at least a portion of the hand of the user when placed over first portion 1902. Thus, the user may comfortably rest their left-hand thumb within depression 1916 while using device 100. The alternate hand of the user (in this case, the right hand) may then be used to perform a needle insertion through guide channel cut-out or aperture 106, which extends through ultrasound probe housing 104 from second portion 1904 of ambient side 112 to body side 114 (not visible in FIG. 19).

In the embodiment of FIG. 19, guide channel cut-out or aperture 106 is a relatively shallow indent that is inset within a perimeter of ultrasound probe housing 104 and passes from second portion 1904 of ambient side 112 to body side 114 (not shown in FIG. 19). The embodiment of FIG. 19 differs from that of FIG. 18 in terms of the shape and position of the indent. Such an embodiment may allow for greater range of movement of needle 102 with respect to guide channel cut-out or aperture 106, while still enabling needle 102 to be passed through guide channel cut-out or aperture 106 in a manner that enables it to appear within a field of view of ultrasound probes 105 of ultrasound probe housing 104 when inserted into the body of the patient. The embodiment of FIG. 19 may be used without needle guide assembly 108. Alternatively, needle guide assembly 108 may be adapted to connect to concave region 1910 and/or guide channel cut-out or aperture 106 so that it may be utilized to help guide and/or stabilize needle 102 during needle insertion. In alternate embodiments, guide channel cut-out 106 may be created in other shapes such as elongated, circular, conical, hyperboloid, etc.

As further shown in FIG. 19, first portion 1902 of ambient side 112 of ultrasound probe housing 104 may comprise a first finger-actuated control 1906 and a second finger-actuated control 1908. In the embodiment shown in FIG. 19, first finger-actuated control 1906 and second finger-actuated control 1908 each comprise a button; however, these finger-actuated controls may be implemented using different structures, such as but not limited to switches, toggles, wheels, touch-sensitive surfaces, reactive surfaces configured to respond to a material in a fingertip of a glove, or the like.

First finger-actuated control 1906 and second finger-actuated control 1908 may be used, for example, to power or off device 100, to activate and/or control a particular functionality that may be provided by device 100, or to perform some other operation with respect to device 100. For example, with respect to activating and/or controlling a particular functionality that may be provided by device 100, and depending upon the implementation of device 100, first finger-actuated control 1906 and second finger-actuated control 1908 may be used to activate and/or control an image capture functionality of device 100, a video capture functionality of device 100, a functionality of device 100 that enables a user to cycle between different depths associated with images or videos captured by device 100, or a functionality of device 100 that enables graphical overlays to be added to or removed from images or videos captured by device 100, or that enables graphical overlays to be added to or removed from particular elements (e.g., needle 102, an internal target body location, an anatomical part of the body of the patient, or the like) that are identified within images or videos captured by device 100. However, first finger-actuated control 1906 and second finger-actuated control 1908 may be used to activate and/or control other functionality of device 100 in other embodiments. First finger-actuated control 1906 and second finger-actuated control 1908 may be located in respective positions on first portion 1902 of ambient side 112 of ultrasound probe housing 104 such that they are proximal to the fingertips of the hand that the user is using to hold or move device 100 (in this case, their left hand). This enables the user to comfortably and easily activate the controls with the fingertips of the same hand that is holding or moving device 100 without having to release their grip on device 100. A finger-actuated control may also be disposed within or proximate to depression

1916 such that it may be activated with the user's thumb when resting in depression 1916. Additional finger-actuated controls with redundant or further functionality may be provided on device 100 within finger reach.

As still further shown in FIG. 19, second portion 1904 of ambient side 112 of ultrasound probe housing 104 may comprise a concave region 1910 that surrounds or partially surrounds guide channel cut-out or aperture 106. Concave region 1910 has a more open shape than concave region 1410 of the embodiment of FIG. 14, but may serve a similar purpose. For example, in some embodiments, a modular version of needle guide assembly 108 may be inserted into concave region 1910 and/or connected thereto. Such concave region 1910 may allow needle guide assembly 108 to be inserted within and/or connected to second portion 1904 of ambient side 112 of ultrasound probe housing 104 for subsequent use in performing a needle insertion. Concave region 1910 may be shaped to provide a desired range of movement of needle 102 and/or needle guide assembly 108 when used by an operator. As noted above, needle guide assembly 108 may be firmly affixed or may be a disposable unit removable upon completion of a procedure or at the convenience of the operator, and may further be sterile. In certain embodiments, concave region 1910 may be absent.

Device 100 shown in FIG. 19 also includes a surface camera 1912 that is connected to second portion 1904 of ambient side 112 of ultrasound probe housing 104 within concave region 1910 and proximate to guide channel cut-out or aperture 106. Surface camera 1912 may be situated such that it has a field of view that encompasses at least a portion of needle 102 as needle 102 passes through guide channel cut-out or aperture 106. Surface camera 1912 may be used to capture images or video of needle 102 that may be used to determine an angle of rotation of needle 102, whether needle 102 has been inserted into the body of the patient, a location of needle 102 for insertion into the body of the patient, or the like. Such images or video may also be processed instantaneously or near-instantaneously by processor 602 for real-time display by display unit 610. Depending upon the implementation and the size/shape of needle guide assembly 108, the connection of needle guide assembly 108 to concave region 1910 may obscure a field of view of surface camera 1912, in which case that camera may be rendered inoperable while needle guide assembly 108 is attached to concave region 1910. In alternate implementations, the connection of needle guide assembly 108 to concave region 1910 may not interfere with operation of surface camera 1912. In still other implementations, surface cameras may also be located in other locations on ultrasound probe housing 104 such as in other locations on first portion 1902 or second portion 1904 of ambient side 112 of ultrasound probe housing 104 or within guide channel cut-out or aperture 106, or may be located elsewhere, such as on needle guide assembly 108.

Although the embodiments of device 100 shown in FIGS. 14, 15, 16A-16D, 17A-17D, 18 and 19 are ergonomically designed for left-handed manipulation and positioning of ultrasound probe housing 104, thereby freeing the right hand for conducting a needle insertion, it is to be understood that device 100 can likewise be designed for right-handed manipulation and positioning of ultrasound probe housing, thereby freeing the left hand for performing needle insertion.

For example, in the embodiment of FIG. 14, first portion 1402 of ambient side 112 of ultrasound probe housing 104 is ergonomically shaped to fit at least a portion of a left hand of the user and second portion 1404 of ambient side 112 of ultrasound probe housing 104 is directly adjacent to first portion 1402 such that second portion 1404 is located to the right of the at least the portion of the left hand of the user when the at least the portion of the left hand of the user is placed over first portion 1402. However, in an alternate design, a first portion of ambient side 112 of ultrasound probe housing 104 may be ergonomically shaped to fit at least a portion of a right hand of the user and a second portion of ambient side 112 of ultrasound probe housing 104 may be directly adjacent to the first portion such that second portion is located to the left of the at least the portion of the right hand of the user when the at least the portion of the right hand of the user is placed over the first portion.

Still further, embodiments of device 100 may be designed for ambidextrous (both right and left hand) use while still being ergonomically designed.

In certain embodiments, ultrasound probe housing 104 may comprise or incorporate one or more mechanisms that form an attachment between at least a portion of the hand of the user and device 100. Such a feature may enhance a user's ability to maneuver device 100 and/or lift device 100 (e.g., away from a body of a patient). For example, ultrasound probe housing 104 may comprise or incorporate a mechanism that allows device 100 to stay attached to a user's hand as the user lifts his/her hand away from a body of a patient. For example, a loop may be permanently or removably attached to ultrasound probe housing 104 (e.g., ambient side 112 of ultrasound probe housing 104) and the user may slide his/her fingers through the loop. The loop may be a strap made of a flexible material, such as fabric or a flexible plastic. Alternatively, the loop may be made of a rigid material, such as metal or a rigid plastic. When a rigid material is utilized, a partial loop (e.g., a loop that is open on one side or that has a gap in the top) may be sufficient to connect device 100 to the hand of the user. For maintaining sterility, a plastic or metal material that is easily wiped clean may be used to implement the loop.

As another example, one or more finger loops may be permanently or removably attached to the first portion (e.g., first portion 1402, first portion 1502, first portion 1602, first portion 1702, first portion 1802, or first portion 1902) of ambient side 112 of ultrasound probe housing 104, and the user one or more of his/her fingers through corresponding ones of the one or more finger loops. As with the hand loops, the finger loop(s) may be made of a flexible material, such as fabric or a flexible plastic, or a rigid material such as metal or a rigid plastic. When a rigid material is utilized, partial finger loops (e.g., finger loop(s) that are open on one side or have a gap at the top) may be sufficient to connect device 100 to the hand of the user. For maintaining sterility, a plastic or metal material that is easily wiped clean may be used to implement the finger loop(s).

Figure 20:
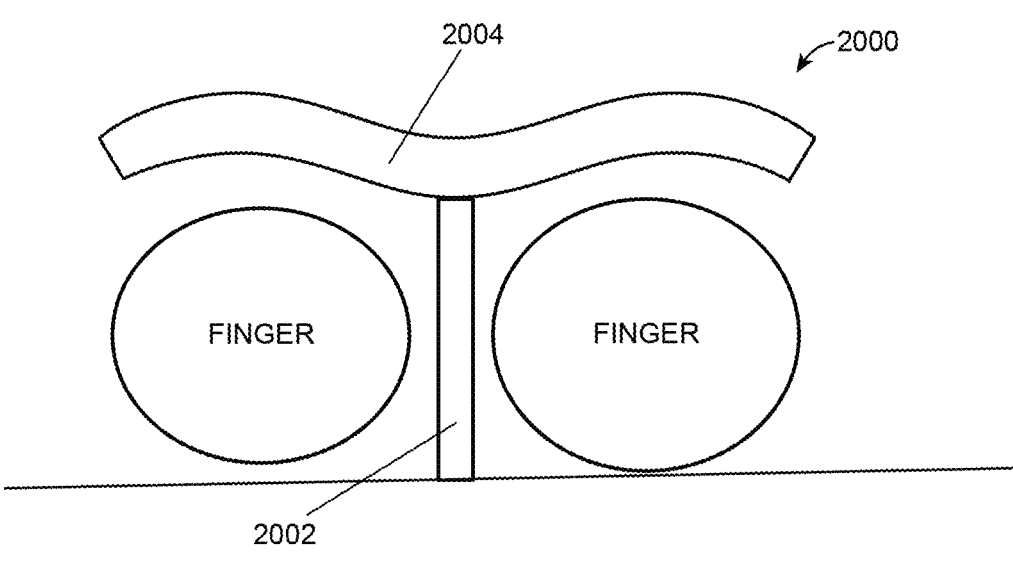
FIG. 20 illustrates a mechanism that may be connected to a device providing a path for inserting a needle for performing medical procedures to enhances a user's ability to grip the device and/or lift the device (e.g., away from a body of a patient), in accordance with an embodiment of the present invention.

FIG. 20 illustrates one example mechanism 2000 that may be connected to any of the embodiments of device 100 described herein to enhances a user's ability to grip the device and/or lift the device (e.g., away from a body of a patient). In particular, as shown in FIG. 20, mechanism 2000 may comprise a vertical bar 2002 that connects to ultrasound probe housing 104 (e.g., ambient side 112 of ultrasound probe housing 104). The connection may be a removable connection that is achieved, for example and without limitation, by snapping the mechanism into ultrasound probe housing 104 or turn locking the mechanism into ultrasound probe housing. As further shown in FIG. 20, mechanism 2000 comprises a horizontal crossbar 2004 that is connected to the top of and is bisected by vertical bar 2002. In this example, vertical bar 2002 is what connects the mechanism to ultrasound probe housing 104. In this way, vertical bar

2002 can sit between the fingers of the user and crossbar 2004 can sit above the fingers of the user. As can be seen in FIG. 20, mechanism 2000 thus creates partial finger loops into which two of the user's fingers may be inserted. If the user lifts her hand, mechanism 2000 allows the device to be lifted up with it. Crossbar 2004 may be contoured on each side from centrally connected vertical bar 2002, to shape over each adjacent finger. However, this is merely one example of a mechanism that enable device 100 to stay attached to a user's hand as the user lifts his/her hand away from a body of a patient, and are not intended to be limiting.

In certain embodiments, ambient side 112 of ultrasound probe housing 104 may be shaped in such a manner that it encompasses or partially encompasses at least a portion of the user's hand (e.g., one or more fingers of the user's hand) when the user's hand is holding device 100 or resting thereon. By way of example only and with continued reference to the embodiment of FIG. 15, ambient side 112 of ultrasound probe housing 104 may include a portion that extends partially or fully over depression 1516, such that when the user's thumb is resting in depression 1516, it is partially or fully encompassed by such portion of ambient side 112 of ultrasound probe housing 104. Likewise, ambient side 112 of ultrasound probe housing 104 may include a portion that extends partially or fully over depression 1516 and an adjacent region of first portion 1502 of ambient side 112, such that the user's thumb and one or more fingers are partially or fully encompassed by ambient side 112 of ultrasound probe housing 104 when the user's hand is holding or resting on device 100. Such a design can advantageously utilize the shape of ambient side 112 of ultrasound probe housing itself to form an attachment between at least a portion of the hand of the user and device 100, thereby enhancing a user's ability to maneuver device 100 and/or lift device 100 (e.g., away from a body of a patient). Such a design may also be implemented with respect to other embodiments of device 100 described herein.

In certain embodiments, ultrasound probe housing 104 may further comprise one or more heat exchange elements, such as vents and/or external heat sinks, that are configured to enable heat to dissipate from inside device 100. Such heat may build up during operation of device 100 due to internal hardware components thereof. By way of example, an embodiment of device 100 may include one or more intake vents that are located on a side of ultrasound probe housing 104 or on a lower portion of ambient side 112 of ultrasound probe housing 104, and one or more exhaust vents that are located at a higher elevation on ultrasound probe housing 104 than the intake vent(s). For example, the exhaust vent(s) may be located higher on the side of ultrasound probe housing 104 or higher on ambient side 112 of ultrasound probe housing than the intake vent(s). Such a design may facilitate an airflow in which cooler air from an environment in which device 100 is being operated is drawn into the intake vent(s) and warmer air that has been heated by the internal hardware components of device 100 rises out of device 100 via the exhaust vent(s). Such vent(s) may be strategically located on ultrasound probe housing 104 in positions that are unlikely to be blocked by a finger or hand of the user who is using device 100, the body of the patient, or by an ultrasound gel that may be applied to the body of the patient.

As noted above, ultrasound probe housing 104 may also comprise an external heat sink. For example, a metal structure that connects to one or more internal heat generating or heat conducting elements within device 100 may protrude from or be exposed via an aperture in ultrasound probe housing 104, such that heat may be conducted from the inside of device 100 through the metal structure to the outside of device 100. Such metal structure may be strategically located on ultrasound probe housing 104 in positions that are unlikely to come into contact with a finger or hand of the user who is using device 100, the body of the patient, or an ultrasound gel that may be applied to the body of the patient.

Device 100 may further include one or more internal active mechanisms, such as micro-fans, to assist with such heat dissipation, or further passive mechanisms, such as heat sinks, that transfer generated heat to a fluid medium, e.g., air or liquid coolant, where it is dissipated away from the device.

Figure 21:
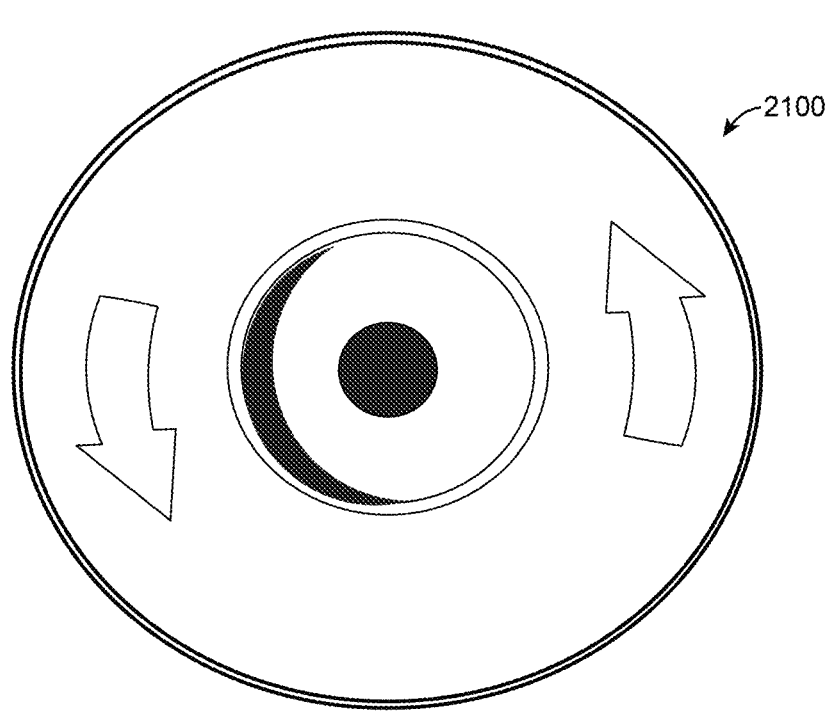
FIG. 21 illustrates a rotational clip connector that may be used to a connect a modular version of a needle guide assembly to a device providing a path for inserting a needle for performing medical procedures, in accordance with an embodiment of the present invention.

As was previously discussed with respect to the embodiments of FIGS. 14, 15, 16A-16D, 17A-17D, 18 and 19, a second portion of ambient side 112 of ultrasound probe housing 104 may comprise a concave region to which a modular version of needle guide assembly 108 may be attached. The inclusion of the concave region may enable easy switching between a hand-operated procedure in which needle guide assembly 108 is not attached to the concave region and a guided procedure in which needle guide assembly 108 is attached to the concave region. FIGS. 14, 15, 16A-16D, 17A-17D, 18 and 19 each show device 100 without needle guide assembly 108 inserted into the receiving concave region. The concave region may be adapted to work with both cutout and aperture configurations of guide channel cut-out or aperture 106. The modular version of needle guide assembly 108 that attaches to the concave region may comprise a circular component that houses the components of needle guide assembly 108 and that fits into or is seated in the concave region. Any of a wide variety of connection types may be used to attach the modular version of needle guide assembly 108, such as a snapping mechanism, rotational clip, interference fit, threaded fastener, hook and loop fastener, adhesives, tapes, or the like. FIG. 21 illustrates a rotational clip connector 2100 that may be used to connect a modular version of needle guide assembly 108.

It is further noted that the ergonomic shapes of ultrasound probe housing 104 as shown in FIGS. 14-16, 17A-17D, 18 and 19 are presented by way of example and are not intended to be limiting. A wide variety of other shapes may be used. For example, more finger depressions than just a single thumb depression may be used. Different sized housings may be made available to match different hand sizes. Furthermore, external ergonomic designs may be custom made and formed to a specific operator's hand without impacting the internal hardware necessary for device 100 to function as described.

In certain embodiments of device 100, a display may be attached to ultrasound probe housing 104. For example, the display may be attached to ultrasound probe housing 104 via a connector such that the display is separate from ultrasound probe housing 104 but fixedly or removably attached thereto. As another example, the display may be integrated into ultrasound probe housing 104. Alternatively, the display may be external to device 100 but connected thereto via a wired or wireless connection. In such a scenario, the display may be attached to a portion of the user's body (e.g., a finger, hand, wrist or extremity of the user). In further accordance with this example, the display may be affixed to the wrist of the hand of the user that is holding device 100 so that the display is readily visible to the user while using the device. The display may also be provided elsewhere. For example, the display may comprise a component of a tablet, smartphone or monitor that is communicatively connected to device 100 via a wired or wireless connection and that is situated on a stand, bed, table, or other surface nearby the site at which the procedure is being performed such that it is visible to the operator. As another example, the display may be located remotely with respect to the site at which the procedure is being performed so that a third-party operator can visualize and assist in the procedure remotely. In certain implementations, the display is located in a convenient sightline for the user and does not impede operation.

The display can be used to display a variety of information, such as ultrasound images or video generated based on data from ultrasound probes 105, images or video captured by surface cameras affixed to ultrasound probe housing 104, or any other information directly or indirectly related to device 100. The display can also be used to display information about the patient, a procedure being performed, or the like. In embodiments in which the display is attached to ultrasound probe housing 104 or to the user, the attachment mechanism may comprise an adhesive or locking/securing mechanism. For example, a band or strap may be used to attach the display to ultrasound probe housing 104 or to the operator. As another example, the display may include a disposable or reusable adhesive feature to allow for securing position with or without the band or strap. The adhesive feature can be attached to any object or person.

Figure 22:
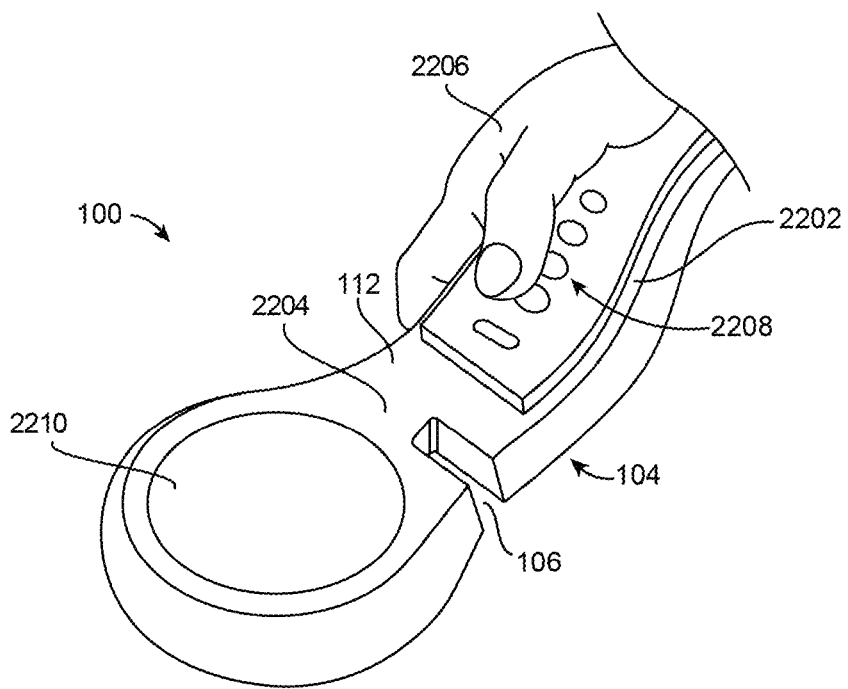
FIG. 22 illustrates a perspective view of a device providing a path for inserting a needle for performing medical procedures that is designed to facilitate use by a single user and which includes an integrated display, in accordance with an embodiment of the present invention.

FIG. 22 illustrates a perspective view of device 100 in accordance with another embodiment in which ultrasound probe housing 104 is sized and shaped to facilitate use thereof by a single user and in which ultrasound probe housing 104 includes an integrated display.

As shown in FIG. 22, ambient side 112 of ultrasound probe housing 104 includes a first portion 2202 and a second portion 2204 that is directly adjacent to first portion 2202. First portion 2202 is ergonomically shaped to fit within at least a portion of a hand (in this case, the right hand) of a user. For example, first portion 2202 may be ergonomically shaped to fit within a hand of a user, or a portion of a hand of a user, thereby enabling the user to comfortably use said hand, or said portion of said hand, to adjust a position of device 100 as needed with respect to a body of a patient and/or hold device 100 in place against the body of the patient while performing a needle insertion. The shape of first portion 2202 of ambient side 112 may be contoured to maximize contact area with the user's hand, or the portion of the user's hand, to optimize control of device 100. The alternate hand of the user (in this case, the left hand) may then be used to perform a needle insertion through guide channel cut-out or aperture 106, which extends through ultrasound probe housing 104 from second portion 2204 of ambient side 112 to body side 114 (not visible in FIG. 22).

Needle guide assembly 108 may be present and connected to guide channel cut-out or aperture 106. For example, needle guide assembly 108 may be connected to guide channel cut-out or aperture 106 in any manner previously described. Needle guide assembly 108 may be adapted to receive needle 102 and allow needle 102 to slide along needle guide assembly 108 to perform needle insertion. Alternatively, needle guide assembly 108 may not be present and needle 102 may be hand-operated to perform an insertion through guide channel cut-out or aperture 106. In either case, after passing through guide channel cut-out or aperture 106 and upon insertion into the body of the patient, needle 102 will enter a field of view of ultrasound probes 105 within ultrasound probe housing 104.

As shown in FIG. 22, guide channel cut-out or aperture 106 may have an elongated shape to allow for greater needle angle and to provide a user with easier access to needle 102 and, if present, a catheter hub. In alternate embodiments, guide channel cut-out or aperture 106 may be formed in other shapes such as shallow, circular, conical, hyperboloid, etc. While not shown, it will be appreciated that guide channel cut-out or aperture 106 may reside within a concave region of second portion 2204 of ambient side 112 of ultrasound probe housing 104. During use, a user may grip or hold with her right hand 2206 a portion of ultrasound probe housing 104 that is surmounted by first portion 2202 of ambient side 112, while using her left hand to insert needle 102 through guide channel cut-out or aperture 106.

As further shown in FIG. 22, first portion 2202 of ambient side 112 of ultrasound probe housing 104 may comprise a plurality of finger-actuated controls 2208. In the embodiment shown in FIG. 22, each of finger-actuated controls 2208 comprises a button; however, these finger-actuated controls may be implemented using different structures, such as but not limited to switches, toggles, wheels, touch-sensitive surfaces, reactive surfaces configured to respond to a material in a fingertip of a glove, or the like.

One or more of finger-actuated controls 2208 may be used, for example, to power on or off device 100, to activate and/or control a particular functionality that may be provided by device 100, or to perform some other operation with respect to device 100. For example, with respect to activating and/or controlling a particular functionality that may be provided by device 100, and depending upon the implementation of device 100, one or more of finger-actuated controls 2208 may be used to activate and/or control an image capture functionality of device 100, a video capture functionality of device 100, a functionality of device 100 that enables a user to cycle between different depths associated with images or video captured by device 100, or a functionality of device 100 that enables graphical overlays to be added to or removed from images or video captured by device 100, or that enables graphical overlays to be added to or removed from particular elements (e.g., needle 102, an internal target body location, an anatomical part of the body of the patient, or the like) that are identified within images or video captured by device 100. However, one or more of finger-actuated controls 2208 may be used to activate and/or control other functionality of device 100 in other embodiments. Finger-actuated controls 2208 may be located in respective positions on first portion 2202 of ambient side 112 of ultrasound probe housing 104 such that they are proximal to the thumb of the hand that the user is using to hold or move device 100 (in this case, their right hand). This enables the user to comfortably and easily activate the controls with the thumb of the same hand that is holding or moving device 100 without having to release their grip on device 100. Additional finger-actuated controls with redundant or further functionality may be provided on device 100 within finger reach.

Device 100 shown in FIG. 22 may also include one or more surface cameras that are disposed on ambient side 112 of ultrasound probe housing 104 proximate to guide channel cut-out or aperture 106 and/or within guide channel cut-out or aperture 106. Such surface camera(s) may be situated such that each camera has a field of view that encompasses at least a portion of needle 102 as needle 102 passes through guide channel cut-out or aperture 106. Such surface camera (s) may be used to capture images or video of needle 102 that may be used to determine an angle of rotation of needle 102, whether needle 102 has been inserted into the body of the patient, a location of needle 102 for insertion into the body of the patient, or the like. Such images or video may also be processed instantaneously or near instantaneously by processor 602 for real-time display by display unit 610 and/or by an integrated display 2210. In still other implementations, surface cameras may also be located in other locations on ultrasound probe housing 104 such as in other locations on first portion 2202 or second portion 2204 of ambient side 112 of ultrasound probe housing 104, or may be located elsewhere, such as on needle guide assembly 108.

Device 100 shown in FIG. 22 also includes integrated display 2210. As shown in FIG. 22, integrated display 2210 is located on second portion 2204 of ambient side 112 of ultrasound probe housing 104 such that it is in a convenient sightline to the operator of device 100 during use thereof. In particular, because integrated display 2210 is located proximal to guide channel cut-out or aperture 106 on ambient side 112 of ultrasound probe housing 104, an operator of device 100 can easily view such integrated display 2210 when performing a needle insertion without having to look away from needle 102, needle guide assembly 108 (if present), or guide channel cut-out or aperture 106. Integrated display 2210 may be implemented as an LCD display, an LED display, an OLED display, a TFT display, or any other type of display that is suitable for visually presenting information. As noted above, integrated display 2210 can be used to display a variety of information, such as ultrasound images or video generated based on data from ultrasound probes 105, images or video captured by surface cameras affixed to ultrasound probe housing 104, or any other information directly or indirectly related to device 100. Integrated display 2210 can also be used to display information about the patient, a procedure, or the like.

Figure 23:
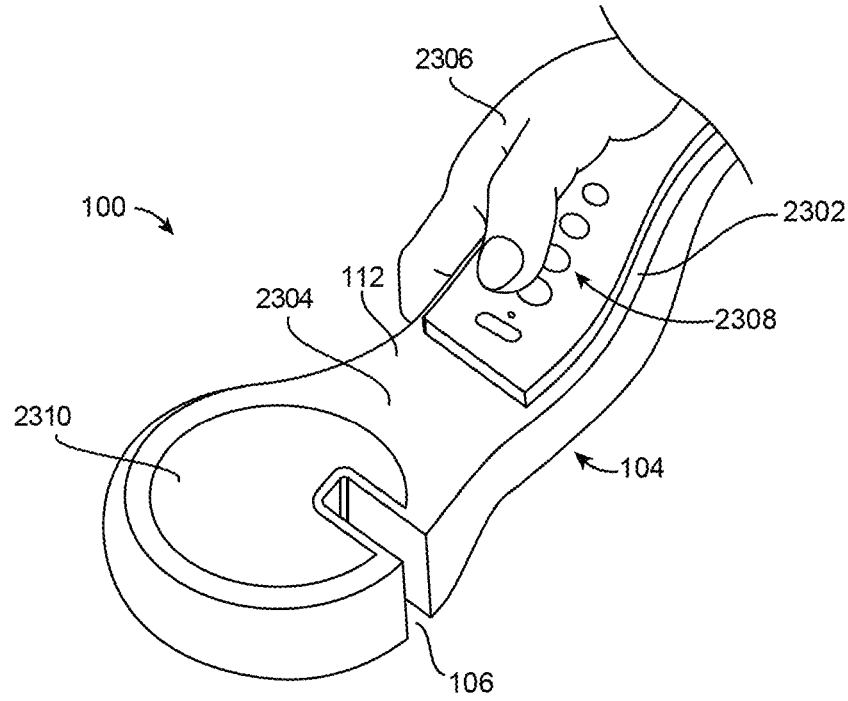
FIG. 23 illustrates a perspective view of a device providing a path for inserting a needle for performing medical procedures that is designed to facilitate use by a single user and which includes an integrated display, in accordance with another embodiment of the present invention.

FIG. 23 illustrates a perspective view of device 100 in accordance with another embodiment in which ultrasound probe housing 104 is sized and shaped to facilitate use thereof by a single user and in which ultrasound probe housing 104 includes an integrated display.

As shown in FIG. 23, ambient side 112 of ultrasound probe housing 104 includes a first portion 2302 and a second portion 2304 that is directly adjacent to first portion 2302. First portion 2302 is ergonomically shaped to fit within at least a portion of a hand (in this case, the right hand) of a user. For example, first portion 2302 may be ergonomically shaped to fit within a hand of a user, or a portion of a hand of a user, thereby enabling the user to comfortably use said hand, or said portion of said hand, to adjust a position of device 100 as needed with respect to a body of a patient and/or hold device 100 in place against the body of the patient while performing a needle insertion. The shape of first portion 2302 of ambient side 112 may be contoured to maximize contact area with the user's hand, or the portion of the user's hand, to optimize control of device 100. The alternate hand of the user (in this case, the left hand) may then be used to perform a needle insertion through guide channel cut-out or aperture 106, which extends through ultrasound probe housing 104 from second portion 2304 of ambient side 112 to body side 114 (not visible in FIG. 23).

Needle guide assembly 108 may be present and connected to guide channel cut-out or aperture 106. For example, needle guide assembly 108 may be connected to guide channel cut-out or aperture 106 in any manner previously described. Needle guide assembly 108 may be adapted to receive needle 102 and allow needle 102 to slide along needle guide assembly 108 to perform needle insertion. Alternatively, needle guide assembly 108 may not be present and needle 102 may be hand-operated to perform an insertion through guide channel cut-out or aperture 106. In either case, after passing through guide channel cut-out or aperture 106 and upon insertion into the body of the patient, needle 102 will enter a field of view of ultrasound probes 105 within ultrasound probe housing 104.

As shown in FIG. 23, guide channel cut-out or aperture 106 may have an elongated shape to allow for greater needle angle and to provide a user with easier access to needle 102 and, if present, a catheter hub. In alternate embodiments, guide channel cut-out or aperture 106 may be formed in other shapes such as shallow, circular, conical, hyperboloid, etc. While not shown, it will be appreciated that guide channel cut-out or aperture 106 may reside within a concave region of second portion 2304 of ambient side 112 of ultrasound probe housing 104. During use, a user may grip or hold with her right hand 2306 a portion of ultrasound probe housing 104 that is surmounted by first portion 2302 of ambient side 112, while using her left hand to insert needle 102 through guide channel cut-out or aperture 106.

As further shown in FIG. 23, first portion 2302 of ambient side 112 of ultrasound probe housing 104 may comprise a plurality of finger-actuated controls 2308. In the embodiment shown in FIG. 23, each of finger-actuated controls 2308 comprises a button; however, these finger-actuated controls may be implemented using different structures, such as but not limited to switches, toggles, wheels, touch-sensitive surfaces, reactive surfaces configured to respond to a material in a fingertip of a glove, or the like.

One or more of finger-actuated controls 2308 may be used, for example, to power on or off device 100, to activate and/or control a particular functionality that may be provided by device 100, or to perform some other operation with respect to device 100. For example, with respect to activating and/or controlling a particular functionality that may be provided by device 100, and depending upon the implementation of device 100, one or more of finger-actuated controls 2308 may be used to activate and/or control an image capture functionality of device 100, a video capture functionality of device 100, a functionality of device 100 that enables a user to cycle between different depths associated with images or video captured by device 100, or a functionality of device 100 that enables graphical overlays to be added to or removed from images or video captured by device 100, or that enables graphical overlays to be added to or removed from particular elements (e.g., needle 102, an internal target body location, an anatomical part of the body of the patient, or the like) that are identified within images or video captured by device 100. However, one or more of finger-actuated controls 2308 may be used to activate and/or control other functionality of device 100 in other embodiments. Finger-actuated controls 2308 may be located in respective positions on first portion 2302 of ambient side 112 of ultrasound probe housing 104 such that they are proximal to the thumb of the hand that the user is using to hold or move device 100 (in this case, their right hand). This enables the user to comfortably and easily activate the controls with the thumb of the same hand that is holding or moving device 100 without having to release their grip on device 100. Additional finger-actuated controls with redundant or further functionality may be provided on device 100 within finger reach.

Device 100 shown in FIG. 23 may also include one or more surface cameras that are disposed on ambient side 112 of ultrasound probe housing 104 proximate to guide channel cut-out or aperture 106 and/or within guide channel cut-out or aperture 106. Such surface camera(s) may be situated such that each camera has a field of view that encompasses at least a portion of needle 102 as needle 102 passes through guide channel cut-out or aperture 106. Such surface camera(s) may be used to capture images or video of needle 102 that may be used to determine an angle of rotation of needle 102, whether needle 102 has been inserted into the body of the patient, a location of needle 102 for insertion into the body of the patient, or the like. Such images or video may also be processed instantaneously or near instantaneously by processor 602 for real-time display by display unit 610 and/or by an integrated display 2310. In still other implementations, surface cameras may also be located in other locations on ultrasound probe housing 104 such as in other locations on first portion 2302 or second portion 2304 of ambient side 112 of ultrasound probe housing 104, or may be located elsewhere, such as on needle guide assembly 108.

Device 100 shown in FIG. 23 also includes integrated display 2310. As shown in FIG. 23, integrated display 2310 is located on second portion 2304 of ambient side 112 of ultrasound probe housing 104 such that it is in a convenient sightline to the operator of device 100 during use thereof. In particular, in the embodiment of FIG. 23, integrated display 2310 partially surrounds guide channel cut-out or aperture 106, such that it appears that guide channel cut-out or aperture 106 passes through integrated display 2310. Due to this configuration, an operator of device 100 can easily view such integrated display 2310 when performing a needle insertion without having to look away from needle 102, needle guide assembly 108 (if present), or guide channel cut-out or aperture 106. Integrated display 2310 may be implemented as an LCD display, an LED display, an OLED display, a TFT display, or any other type of display that is suitable for visually presenting information. As noted above, integrated display 2310 can be used to display a variety of information, such as ultrasound images or video generated based on data from ultrasound probes 105, images or video captured by surface cameras affixed to ultrasound probe housing 104, or any other information directly or indirectly related to device 100. Integrated display 2310 can also be used to display information about the patient, a procedure, or the like.

Figure 24:
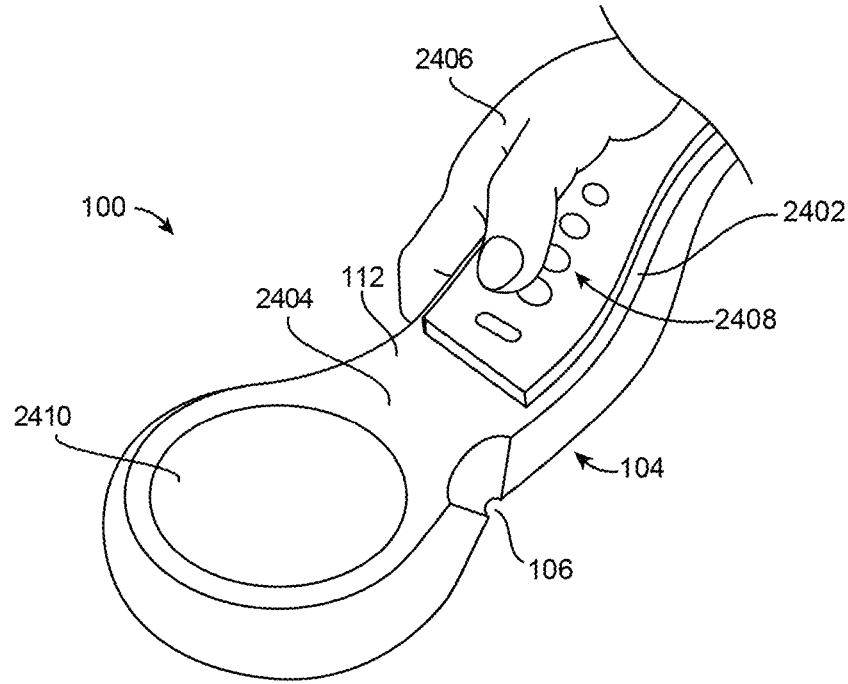
FIG. 24 illustrates a perspective view of a device providing a path for inserting a needle for performing medical procedures that is designed to facilitate use by a single user and which includes an integrated display, in accordance with yet another embodiment of the present invention.

FIG. 24 illustrates a perspective view of device 100 in accordance with another embodiment in which ultrasound probe housing 104 is sized and shaped to facilitate use thereof by a single user and in which ultrasound probe housing 104 includes an integrated display.

As shown in FIG. 24, ambient side 112 of ultrasound probe housing 104 includes a first portion 2402 and a second portion 2404 that is directly adjacent to first portion 2402. First portion 2402 is ergonomically shaped to fit within at least a portion of a hand (in this case, the right hand) of a user. For example, first portion 2402 may be ergonomically shaped to fit within a hand of a user, or a portion of a hand of a user, thereby enabling the user to comfortably use said hand, or said portion of said hand, to adjust a position of device 100 as needed with respect to a body of a patient and/or hold device 100 in place against the body of the patient while performing a needle insertion. The shape of first portion 2402 of ambient side 112 may be contoured to maximize contact area with the user's hand, or the portion of the user's hand, to optimize control of device 100. The alternate hand of the user (in this case, the left hand) may then be used to perform a needle insertion through guide channel cut-out or aperture 106, which extends through ultrasound probe housing 104 from second portion 2404 of ambient side 112 to body side 114 (not visible in FIG. 24).

During use, a user may grip or hold with her right hand 2406 a portion of ultrasound probe housing 104 that is surmounted by first portion 2302 of ambient side 112, while using her left hand to insert needle 102 through guide channel cut-out or aperture 106. In the embodiment of FIG.

24, guide channel cut-out or aperture 106 is a relatively shallow indent that is inset within a perimeter of ultrasound probe housing 104 and passes from second portion 2404 of ambient side 112 to body side 114 (not shown in FIG. 24). Such an embodiment may allow for greater range of movement of needle 102 with respect to guide channel cut-out or aperture 106, while still enabling needle 102 to be passed through guide channel cut-out or aperture 106 in a manner that enables it to appear within a field of view of ultrasound probes 105 of ultrasound probe housing 104 when inserted into the body of the patient. The embodiment of FIG. 24 may be used without needle guide assembly 108. Alternatively, needle guide assembly 108 may be adapted to connect to guide channel cut-out or aperture 106 so that it may be utilized to help guide and/or stabilize needle 102 during needle insertion. In alternate embodiments, guide channel cut-out 106 may be created in other shapes such as elongated, circular, conical, hyperboloid, etc.

As further shown in FIG. 24, first portion 2402 of ambient side 112 of ultrasound probe housing 104 may comprise a plurality of finger-actuated controls 2408. In the embodiment shown in FIG. 24, each of finger-actuated controls 2408 comprises a button; however, these finger-actuated controls may be implemented using different structures, such as but not limited to switches, toggles, wheels, touch-sensitive surfaces, reactive surfaces configured to respond to a material in a fingertip of a glove, or the like.

One or more of finger-actuated controls 2408 may be used, for example, to power on or off device 100, to activate and/or control a particular functionality that may be provided by device 100, or to perform some other operation with respect to device 100. For example, with respect to activating and/or controlling a particular functionality that may be provided by device 100, and depending upon the implementation of device 100, one or more of finger-actuated controls 2408 may be used to activate and/or control an image capture functionality of device 100, a video capture functionality of device 100, a functionality of device 100 that enables a user to cycle between different depths associated with images or video captured by device 100, or a functionality of device 100 that enables graphical overlays to be added to or removed from images or video captured by device 100, or that enables graphical overlays to be added to or removed from particular elements (e.g., needle 102, an internal target body location, an anatomical part of the body of the patient, or the like) that are identified within images or video captured by device 100. However, one or more of finger-actuated controls 2408 may be used to activate and/or control other functionality of device 100 in other embodiments. Finger-actuated controls 2408 may be located in respective positions on first portion 2402 of ambient side 112 of ultrasound probe housing 104 such that they are proximal to the thumb of the hand that the user is using to hold or move device 100 (in this case, their right hand). This enables the user to comfortably and easily activate the controls with the thumb of the same hand that is holding or moving device 100 without having to release their grip on device 100. Additional finger-actuated controls with redundant or further functionality may be provided on device 100 within finger reach.

Device 100 shown in FIG. 24 may also include one or more surface cameras that are disposed on ambient side 112 of ultrasound probe housing 104 proximate to guide channel cut-out or aperture 106 and/or within guide channel cut-out or aperture 106. Such surface camera(s) may be situated such that each camera has a field of view that encompasses at least a portion of needle 102 as needle 102 passes through guide channel cut-out or aperture 106. Such surface camera (s) may be used to capture images or video of needle 102 that may be used to determine an angle of rotation of needle 102, whether needle 102 has been inserted into the body of the patient, a location of needle 102 for insertion into the body of the patient, or the like. Such images or video may also be processed instantaneously or near instantaneously by processor 602 for real-time display by display unit 610 and/or by an integrated display 2410. In still other implementations, surface cameras may also be located in other locations on ultrasound probe housing 104 such as in other locations on first portion 2402 or second portion 2404 of ambient side 112 of ultrasound probe housing 104, or may be located elsewhere, such as on needle guide assembly 108.

Device 100 shown in FIG. 24 also includes integrated display 2410. As shown in FIG. 24, integrated display 2410 is located on second portion 2404 of ambient side 112 of ultrasound probe housing 104 such that it is in a convenient sightline to the operator of device 100 during use thereof. In particular, because integrated display 2410 is located proximal to guide channel cut-out or aperture 106 on ambient side 112 of ultrasound probe housing 104, an operator of device 100 can easily view such integrated display 2410 when performing a needle insertion without having to look away from needle 102, needle guide assembly 108 (if present), or guide channel cut-out or aperture 106. Integrated display 2410 may be implemented as an LCD display, an LED display, an OLED display, a TFT display, or any other type of display that is suitable for visually presenting information. As noted above, integrated display 2410 can be used to display a variety of information, such as ultrasound images or video generated based on data from ultrasound probes 105, images or video captured by surface cameras affixed to ultrasound probe housing 104, or any other information directly or indirectly related to device 100. Integrated display 2410 can also be used to display information about the patient, a procedure, or the like.

Figure 25:
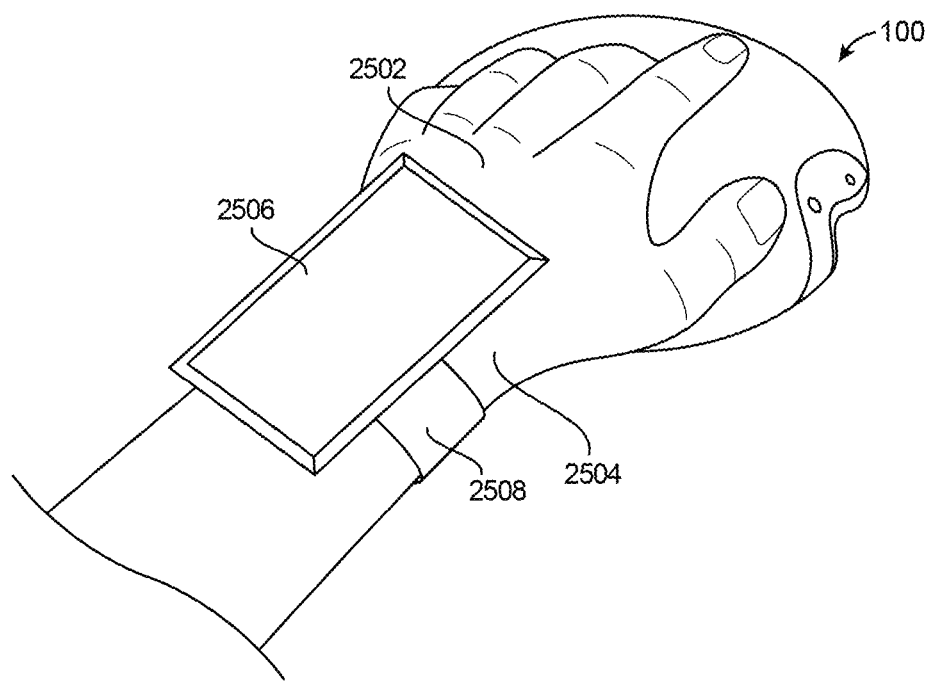
FIG. 25 illustrates a perspective view of an associated display that may be used in conjunction with a device providing a path for inserting a needle for performing medical procedures, in accordance with an embodiment of the present invention.

FIG. 25 depicts a perspective view of an associated display 2506 that may be used in conjunction with device 100 in accordance with an embodiment. In the embodiment of FIG. 25, display 2506 is attached to a left wrist 2504 of an operator using a band or loop 2508, such that display 2506 may be easily viewed by the operator while the operator is holding or manipulating device 100 with his or her left hand 2502. In such a configuration, display 2506 is located in a convenient sightline for the user and does not impede operation.

Band or loop 2508 may be made of a flexible material, such as fabric or a flexible plastic. Alternatively, band or loop 2508 may be made of a rigid material, such as metal or a rigid plastic. When a rigid material is utilized, a partial loop may be sufficient to connect display 2506 to wrist 2504 of the user. For maintaining sterility, a plastic or metal material that is easily wiped clean may be used to implement band or loop 2508.

Display 2506 may be connected to device 100 via a wired or wireless connection. Display 2506 can be used to display a variety of information, such as ultrasound images or video generated based on data from ultrasound probes 105, images or video captured by surface cameras affixed to ultrasound probe housing 104, or any other information directly or indirectly related to device 100. Display 2506 can also be used to display information about the patient, a procedure being performed, or the like.

Although display 2506 is shown as being attached to left wrist 2504 of the user via a band or loop 2508, it will be appreciated that other mechanisms may be used to affix display 2506 to the wrist, such as a disposable or reusable adhesive, a fixed (e.g., sewn) attachment to a sleeve or glove, a removable (e.g., hook and loop) attachment to a sleeve or glove, or the like. Furthermore, it will be appreciated that display 2506 may be similarly affixed to a right hand of a user in a scenario in which the user is using his or her right hand to hold or manipulate device 100.

Figure 26:
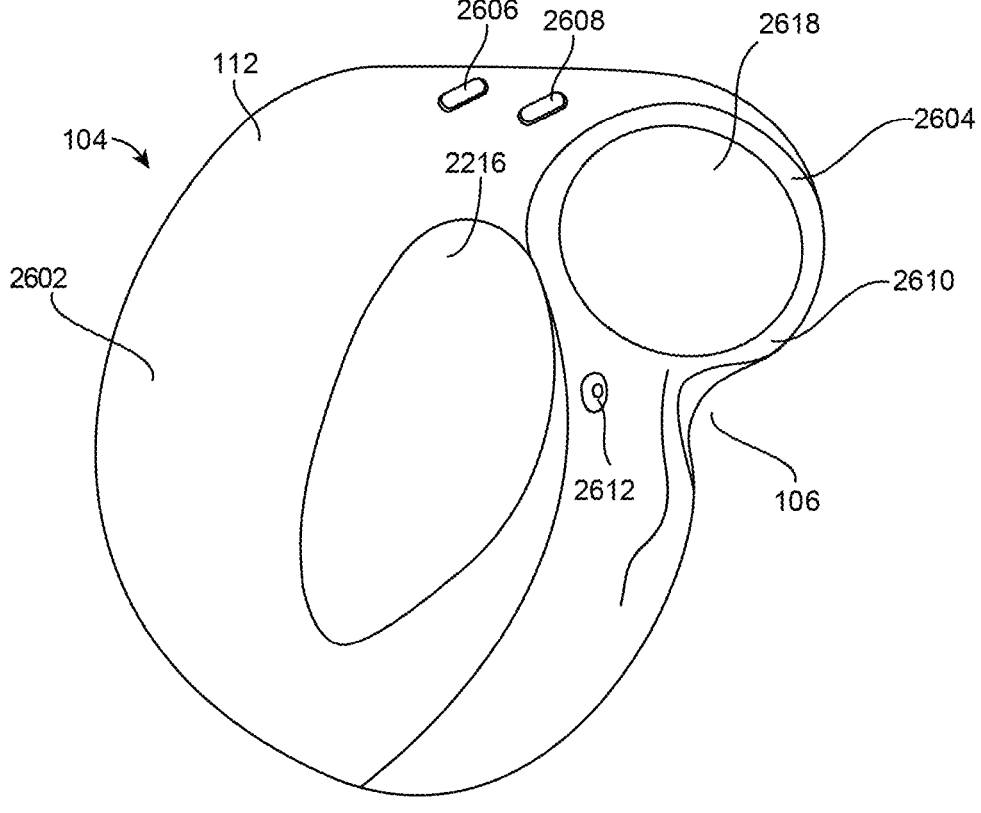
FIG. 26 illustrates a perspective view of a device providing a path for inserting a needle for performing medical procedures that is designed to facilitate use by a single user and which includes an integrated display, in accordance with a further embodiment of the present invention.

FIG. 26 depicts a perspective view of device 100 in accordance with another embodiment in which ultrasound probe housing 104 is sized and shaped to facilitate use thereof by a single user and includes an integrated display. As shown in FIG. 26, ambient side 112 of ultrasound probe housing 104 includes a first portion 2602 and a second portion 2604 that is directly adjacent to first portion 2602. First portion 2602 is ergonomically shaped to fit at least a portion of a hand (in this case, the left hand) of a user. For example, first portion 2602 may be ergonomically shaped to fit within a cupped hand of a user, or a cupped portion of a hand of a user, with a relaxed, natural and low tension grip, thereby enabling the user to comfortably use said hand, or said portion of said hand, to adjust a position of device 100 as needed with respect to a body of a patient and/or hold device 100 in place against the body of the patient while performing a needle insertion. The shape of first portion 2602 of ambient side 112 may be contoured to maximize contact area with the user's hand, or the portion of the user's hand, to optimize control of device 100. In addition, first portion 2602 of ambient side 112 of ultrasound probe housing 104 includes a depression 2616 that is adapted to fit a thumb of the at least a portion of the hand of the user when placed over first portion 2602. Thus, the user may comfortably rest their left-hand thumb within depression 2616 while using device 100. The alternate hand of the user (in this case, the right hand) may then be used to perform a needle insertion through guide channel cut-out or aperture 106, which extends through ultrasound probe housing 104 from second portion 2604 of ambient side 112 to body side 114 (not visible in FIG. 26).

In the embodiment of FIG. 26, guide channel cut-out or aperture 106 is a relatively shallow indent that is inset within a perimeter of ultrasound probe housing 104 and passes from second portion 2604 of ambient side 112 to body side 114 (not shown in FIG. 26). Such an embodiment may allow for greater range of movement of needle 102 with respect to guide channel cut-out or aperture 106, while still enabling needle 102 to be passed through guide channel cut-out or aperture 106 in a manner that enables it to appear within a field of view of ultrasound probes 105 of ultrasound probe housing 104 when inserted into the body of the patient. The embodiment of FIG. 26 may be used without needle guide assembly 108. Alternatively, needle guide assembly 108 may be adapted to connect to concave region 2610 and/or guide channel cut-out or aperture 106 so that it may be utilized to help guide and/or stabilize needle 102 during needle insertion. In alternate embodiments, guide channel cut-out 106 may be created in other shapes such as elongated, circular, conical, hyperboloid, etc.

As further shown in FIG. 26, first portion 2602 of ambient side 112 of ultrasound probe housing 104 may comprise a first finger-actuated control 2606 and a second finger-actuated control 2608. In the embodiment shown in FIG. 26, first finger-actuated control 2606 and second finger-actuated control 2608 each comprise a button; however, these finger-actuated controls may be implemented using different structures, such as but not limited to switches, toggles, wheels, touch-sensitive surfaces, reactive surfaces configured to respond to a material in a fingertip of a glove, or the like.

First finger-actuated control 2606 and second finger-actuated control 2608 may be used, for example, to power on or off device 100, to activate and/or control a particular functionality that may be provided by device 100, or to perform some other function with respect to device 100. For example, with respect to activating and/or controlling a particular functionality that may be provided by device 100, and depending upon the implementation of device 100, first finger-actuated control 2606 and second finger-actuated control 2608 may be used to activate and/or control an image capture functionality of device 100, a video capture functionality of device 100, a functionality of device 100 that enables a user to cycle between different depths associated with images or videos captured by device 100, or a functionality of device 100 that enables graphical overlays to be added to or removed from images or videos captured by device 100, or that enables graphical overlays to be added to or removed from particular elements (e.g., needle 102, an internal target body location, an anatomical part of the body of the patient, or the like) that are identified within images or videos captured by device 100. However, first finger-actuated control 2606 and second finger-actuated control 2608 may be used to activate and/or control other functionality of device 100 in other embodiments. First finger-actuated control 2606 and second finger-actuated control 2608 may be located in respective positions on first portion 2602 of ambient side 112 of ultrasound probe housing 104 such that they are proximal to the fingertips of the hand that the user is using to hold or move device 100 (in this case, their left hand). This enables the user to comfortably and easily activate the controls with the fingertips of the same hand that is holding or moving device 100 without having to release their grip on device 100. A finger-actuated control may also be disposed within or proximate to depression 2616 such that it may be activated with the user's thumb when resting in depression 2616. Additional finger-actuated controls with redundant or further functionality may be provided on device 100 within finger reach.

As still further shown in FIG. 26, second portion 2604 of ambient side 112 of ultrasound probe housing 104 may comprise a concave region 2610 that surrounds or partially surrounds guide channel cut-out or aperture 106. Concave region 2610 has a more open shape than concave region 1410 of the embodiment of FIG. 14, but may serve a similar purpose. For example, in some embodiments, a modular version of needle guide assembly 108 may be inserted into concave region 2610 and/or connected thereto. Such concave region 2610 may allow needle guide assembly 108 to be inserted within and/or connected to second portion 2604 of ambient side 112 of ultrasound probe housing 104 for subsequent use in performing a needle insertion. Concave region 2610 may be shaped to provide a desired range of movement of needle 102 and/or needle guide assembly 108 when used by an operator. As noted above, needle guide assembly 108 may be firmly affixed or may be a disposable unit removable upon completion of a procedure or at the convenience of the operator, and may further be sterile. In certain embodiments, concave region 2610 may be absent.

Device 100 shown in FIG. 26 also includes a surface camera 2612 that is connected to second portion 2604 of ambient side 112 of ultrasound probe housing 104 within concave region 2610 and proximate to guide channel cut-out or aperture 106. Surface camera 2612 may be situated such that it has a field of view that encompasses at least a portion of needle 102 as needle 102 passes through guide channel cut-out or aperture 106. Surface camera 2612 may be used to capture images or video of needle 102 that may be used to determine an angle of rotation of needle 102, whether needle 102 has been inserted into the body of the patient, a location of needle 102 for insertion into the body of the patient, or the like. Such images or video may also be processed instantaneously or near-instantaneously by processor 602 for real-time display by display unit 610 or an integrated display 2618. Depending upon the implementation and the size/shape of needle guide assembly 108, the connection of needle guide assembly 108 to concave region 2610 may obscure a field of view of surface camera 2612, in which case that camera may be rendered inoperable while needle guide assembly 108 is attached to concave region 2610. In alternate implementations, the connection of needle guide assembly 108 to concave region 2610 may not interfere with operation of surface camera 2612. In still other implementations, surface cameras may also be located in other locations on ultrasound probe housing 104 such as in other locations on first portion 2602 or second portion 2604 of ambient side 112 of ultrasound probe housing 104 or within guide channel cut-out or aperture 106, or may be located elsewhere, such as on needle guide assembly 108.

Device 100 shown in FIG. 26 also includes integrated display 2618. As shown in FIG. 24, integrated display 2618 is located on second portion 2604 of ambient side 112 of ultrasound probe housing 104 such that it is in a convenient sightline to the operator of device 100 during use thereof. In particular, because integrated display 2618 is located proximal to guide channel cut-out or aperture 106 on ambient side 112 of ultrasound probe housing 104, an operator of device 100 can easily view such integrated display 2618 when performing a needle insertion without having to look away from needle 102, needle guide assembly 108 (if present), or guide channel cut-out or aperture 106. Integrated display 2618 may be implemented as an LCD display, an LED display, an OLED display, a TFT display, or any other type of display that is suitable for visually presenting information. As noted above, integrated display 2618 can be used to display a variety of information, such as ultrasound images or video generated based on data from ultrasound probes 105, images or video captured by surface cameras affixed to ultrasound probe housing 104, or any other information directly or indirectly related to device 100. Integrated display 2618 can also be used to display information about the patient, a procedure, or the like.

It is to be understood that each of the embodiments of device 100 shown in FIGS. 14, 15, 16A-16D, 17A-17D, 18, 19 and 22-26 may include or may be adapted to include any of the various features described above with respect to FIGS. 1, 2, 3A, 3B, 4A, 4B, 5-7, 8A, 8B, 9A, 9B, 9C, 9D, 10A, 10B, 11A, 11B, 12A, 12B, 13A and 13B. For example, and without limitation, each of the embodiments of device 100 shown in FIGS. 14, 15, 16, 17A-17D, 18, 19 and 22-26 may include a mixed array of angled and perpendicular probes 105 and/or a mixed array of probes 105 at varying distances from body side 114 of ultrasound probe housing 114 as discussed above in reference to FIG. 3B, and/or any of the various adhesion or attachment features discussed above with respect to FIG. 10A, 10B, 11A, 11B, 12A, 12B, 13A, or 13B.

While various embodiments of a device 100 that provides a path for inserting a needle inside a body of a patient have been described herein, persons skilled in the relevant art(s) will readily appreciate that such embodiments may be adapted for use in inserting other medical instruments inside a body of a patient. For example, the structures and methods described herein can be readily adapted to provide a path for inserting an arthroscope inside a body of a patient as part of an arthroscopic procedure. Furthermore, the term needle is intended to represent all types of needles, including but not limited to core needles, aspiration needles and vacuum-assisted needles which may be used to perform a biopsy.

In the foregoing description, it will be readily appreciated by those skilled in the art that modifications may be made to the invention without departing from the concepts disclosed herein. Such modifications are to be considered as included in the following claims, unless the claims by their language expressly state otherwise.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. The various embodiments set forth herein are described in terms of exemplary block diagrams and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment.

What is claimed is:

1. A device comprising:
an ultrasound probe housing that contains a plurality of ultrasound probes configured to generate ultrasound waves for producing images of inside a body of a patient, the ultrasound probe housing having a body side that faces toward the body of the patient and an ambient side that faces away from the body of the patient, the ambient side of the ultrasound probe housing comprising a first portion that is shaped to fit within a cupped hand of a user such that a palm of the cupped hand faces toward the body of the patient and a second portion that is directly adjacent to the first portion; and
a guide channel cut-out or aperture that extends through the ultrasound probe housing from the second portion of the ambient side to the body side, the guide channel cut-out or aperture being adapted to accommodate passage of a needle through the guide channel cut-out or aperture for insertion into the body of the patient such that the needle is in a field of view of the plurality of ultrasound probes upon insertion into the body of the patient.

2. The device of claim 1, wherein the first portion of the ambient side of the ultrasound probe housing is shaped to fit within a cupped left hand of the user and wherein the second portion of the ambient side of the ultrasound probe housing is directly adjacent to the first portion such that the second portion is located to the right of the cupped left hand of the user when the cupped left hand of the user is placed over the first portion.

3. The device of claim 1, wherein the first portion of the ambient side of the ultrasound probe housing is shaped to fit within a cupped right hand of the user and wherein the second portion of the ambient side of the ultrasound probe housing is directly adjacent to the first portion such that the second portion is located to the left of the cupped right hand of the user when the cupped right hand of the user is placed over the first portion.

4. The device of claim 1, wherein the device further comprises:
  a needle guide assembly that is connected to the guide channel cut-out or aperture, the needle guide assembly being adapted to receive the needle and allow the needle to slide along the needle guide assembly for insertion into the body of the patient.

5. The device of claim 4, wherein the needle guide assembly is connected to the guide channel cut-out or aperture at a pivot point within the guide channel cut-out or aperture and wherein the needle guide assembly is rotatable about the pivot point.

6. The device of claim 4, wherein the guide channel cut-out or aperture is located in a concave region of the second portion of the ambient side of the ultrasound probe housing and wherein the needle guide assembly is connected to the guide channel cut-out or aperture by virtue of a connection to the concave region.

7. The device of claim 1, wherein a shape of the guide channel cut-out or aperture is one of:
  indented;
  elongated;
  circular;
  conical; or
  hyperboloid.

8. The device of claim 1, wherein the first portion of the ambient side of the ultrasound probe housing comprises one or more finger-actuated controls that are positioned to be proximal to a fingertip of the cupped hand of the user when placed over the first portion, wherein one of the one or more finger-actuated controls are useable to activate or control a functionality of the device.

9. The device of claim 8, wherein the functionality of the device comprises one or more of:
  image capture;
  video capture;
  image depth cycling; or
  graphic overlay application or removal.

10. The device of claim 1, wherein the second portion of the ambient side of the ultrasound probe housing comprises:
  at least one camera having a field of view that encompasses at least a portion of the needle when the needle passes through the guide channel cut-out or aperture.

11. The device of claim 1, wherein the first portion of the ambient side of the ultrasound probe housing comprises a depression adapted to fit a thumb of the cupped hand of the user when placed over the first portion.

12. The device of claim 1, wherein the body side of the ultrasound probe housing is contoured to fit on a part of the body of the patient.

13. The device of claim 12, wherein the body side of the ultrasound probe housing is curved to fit on a limb of the body of the patient.

14. The device of claim 1, wherein the ultrasound probe housing further comprises a mechanism configured to form an attachment between the at least the portion of the hand of the user and the device.

15. The device of claim 14, wherein the mechanism comprises one of:
  a full or partial hand loop connected to the ultrasound probe housing; or
  one or more partial or full finger loops connected to the first portion of the ambient side of the ultrasound probe housing.

16. The device of claim 1, wherein the ultrasound probe housing comprises one or more heat exchange elements that are configured to enable heat to dissipate from inside the device.

17. The device of claim 1, wherein a portion of the ultrasound probe housing between the first portion of the ambient side and the body side has a higher profile than a portion of the ultrasound probe housing between the second portion of the ambient side and the body side.

18. A device comprising:
  an ultrasound probe housing that contains a plurality of ultrasound probes configured to generate ultrasound waves for producing images of inside a body of a patient, the ultrasound probe housing having a body side that faces toward the body of the patient and an ambient side that faces away from the body of the patient, the ambient side of the ultrasound probe housing comprising a first portion that is shaped to fit within a cupped hand of a user such that a palm of the cupped hand faces toward the body of the patient and a second portion that is directly adjacent to the first portion;
  an indent that extends through the ultrasound probe housing from the second portion of the ambient side to the body side, the indent being adapted to accommodate passage of a needle through the indent for insertion into the body of the patient such that the needle is in the field of view of the plurality of ultrasound probes upon insertion into the body of the patient.

19. The device of claim 18, wherein the first portion of the ambient side of the ultrasound probe housing is shaped to fit within a cupped left hand of the user and wherein the second portion of the ambient side of the ultrasound probe housing is directly adjacent to the first portion such that the second portion is located to the right of the cupped left hand of the user when the cupped left hand of the user is placed over the first portion.

20. The device of claim 18, wherein the first portion of the ambient side of the ultrasound probe housing is shaped to fit within a cupped right hand of the user and wherein the second portion of the ambient side of the ultrasound probe housing is directly adjacent to the first portion such that the second portion is located to the left of the cupped right hand of the user when the cupped right hand of the user is placed over the first portion.

21. The device of claim 18, wherein the first portion of the ambient side of the ultrasound probe housing comprises one or more finger-actuated controls that are positioned to be proximal to a fingertip of the cupped hand of the user when placed over the first portion, wherein one of the one or more finger-actuated controls are useable to activate or control a functionality of the device.

22. The device of claim 21, wherein the functionality of the device comprises one or more of:

image capture;

video capture;

image depth cycling; or graphic overlay application or removal.

23. The device of claim 18, wherein the second portion of the ambient side of the ultrasound probe housing comprises:

at least one camera having a field of view that encompasses at least a portion of the needle when the needle passes through the indent.

24. The device of claim 18, wherein the first portion of the ambient side of the ultrasound probe housing comprises a depression adapted to fit a thumb of the cupped hand of the user when placed over the first portion.

25. The device of claim 18, wherein the body side of the ultrasound probe housing is contoured to fit on a part of the body of the patient.

26. The device of claim 25, wherein the body side of the ultrasound probe housing is curved to fit on a limb of the body of the patient.

27. The device of claim 18, wherein the ultrasound probe housing further comprises a mechanism configured to form an attachment between the at least the portion of the hand of the user and the device.

28. The device of claim 27, wherein the mechanism comprises one of:

a full or partial hand loop connected to the ultrasound probe housing; or one or more partial or full finger loops connected to the first portion of the ambient side of the ultrasound probe housing.

29. The device of claim 18, wherein the ultrasound probe housing comprises one or more heat exchange elements that are configured to enable heat to dissipate from inside the device.

30. The device of claim 18, wherein a portion of the ultrasound probe housing between the first portion of the ambient side and the body side has a higher profile than a portion of the ultrasound probe housing between the second portion of the ambient side and the body side.

* * * * *